US008435505B2

(12) United States Patent
Bentley et al.

(10) Patent No.: US 8,435,505 B2
(45) Date of Patent: *May 7, 2013

(54) PHARMACEUTICAL COMPOSITIONS AND METHODS FOR DELIVERING SUCH COMPOSITIONS

(75) Inventors: Michael D. Bentley, Huntsville, AL (US); Sean M. Culbertson, Gurley, AL (US); Samuel P. McManus, Huntsville, AL (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/525,068

(22) Filed: Jun. 15, 2012

(65) Prior Publication Data

US 2012/0258912 A1    Oct. 11, 2012

Related U.S. Application Data

(63) Continuation of application No. 11/454,971, filed on Jun. 16, 2006, now Pat. No. 8,252,275.

(60) Provisional application No. 60/691,516, filed on Jun. 16, 2005, provisional application No. 60/705,968, filed on Aug. 4, 2005, provisional application No. 60/751,082, filed on Dec. 16, 2005, provisional application No. 60/751,121, filed on Dec. 16, 2005, provisional application No. 60/752,825, filed on Dec. 21, 2005.

(51) Int. Cl.
*A61K 31/74* (2006.01)

(52) U.S. Cl.
USPC ..................................... 424/78.17

(58) Field of Classification Search ..................... None
See application file for complete search history.

(56) References Cited

U.S. PATENT DOCUMENTS

| | | | |
|---|---|---|---|
| 4,510,233 A | 4/1985 | Yokoyama et al. |
| 5,629,384 A | 5/1997 | Veronese et al. |
| 5,900,327 A | 5/1999 | Pei et al. |
| 5,932,462 A | 8/1999 | Harris et al. |
| 6,313,242 B1 | 11/2001 | Reddy |
| 6,362,254 B2 | 3/2002 | Harris et al. |
| 6,514,491 B1 | 2/2003 | Bentley et al. |
| 6,777,531 B2 | 8/2004 | Yasuda et al. |
| 8,252,275 B2 | 8/2012 | Bentley et al. |
| 2005/0079155 A1 | 4/2005 | Marshall |
| 2006/0171920 A1 | 8/2006 | Shechter et al. |
| 2007/0027073 A1 | 2/2007 | Rubinstein et al. |

FOREIGN PATENT DOCUMENTS

| | | |
|---|---|---|
| EP | 0 473 084 | 11/1995 |
| EP | 1 249 846 | 10/2002 |
| JP | 4-108827 | 4/1992 |
| JP | 2004-530736 | 10/2004 |

(Continued)

OTHER PUBLICATIONS

Canadian Office Action corresponding to Canadian Patent Application No. 2,611,823 dated Aug. 8, 2012.

(Continued)

*Primary Examiner* — Paul Dickinson
(74) *Attorney, Agent, or Firm* — Mark A. Wilson

(57) ABSTRACT

The present invention provides pharmaceutical compositions comprising a pharmaceutically acceptable excipient and a conjugate having a degradable linkage. The conjugates include at least one of each the following: an aromatic moiety comprising an ionizable hydrogen atom, a spacer moiety, and a water-soluble polymer. Methods for delivering such compositions are also provided.

21 Claims, 12 Drawing Sheets

FOREIGN PATENT DOCUMENTS

| | | |
|---|---|---|
| JP | 2004-532289 | 10/2004 |
| WO | WO 00/44785 | 8/2000 |
| WO | WO 02/36067 | 5/2002 |
| WO | WO 2004/089280 | 10/2004 |
| WO | WO 2004/108070 | 12/2004 |
| WO | WO 2005/014049 | 2/2005 |
| WO | WO 2005/016240 | 2/2005 |
| WO | WO 2007/019331 | 2/2007 |

OTHER PUBLICATIONS

Colombian Official Action corresponding to Colombian Patent Application No. 08003741 dated Jul. 30, 2012.
Andrew, et al., "The Nitration of 3-Methoxyfluoranthene", J. Chem. Soc. (C) Org., pp. 1761-1764, (1968).
Barker, et al., "3: 6-Disubstituted Fluorenes. Part II. The Preparation of 3:6-Diaminofluorene from Fluorene, and the Attempted Internuclear Cyclisation of Derivatives of 4:4-Diaminodiphenylmethane", J. Chem. Soc., pp. 870-873, (1954).
Blackburn, et al., "Fluorene-1-carboxylic Acid", Acta Cryst., C52, pp. 907-909, (1996).
Bodanszky, et al., "Derivatives of S-9-fluorenylmethyl-L-Cysteine", Int. J. Peptide Protein Res., vol. 20, pp. 434-437, (1982).
Bordwell, et al., "Steric Inhibition of Synergistic Radical Stabilizing Effects", J. Org. Chem., pp. 58-63, (1990).
Eisenbeis, et al., "A Practical Large Scale Synthesis of 9-(Hydroxymethyl)-Fluorene-4-Carboxylic Acid (HOFmCO2H)", Synthetic Communications, vol. 31, No. 22, pp. 3533-3536, (2001).
Gershonov, et al., "New Concept for Long-Acting Insulin: Spontaneous Conversion of an Inactive Modified Insulin to the Active Hormone in Circulation: 9-Fluorenylmethoxycarbonyl Derivative of Insulin", Diabetes, vol. 48, pp. 1437-1442, (Jul. 1999).
Gershonov, et al., "A Novel Approach for a Water-Soluble Long-Acting Insulin Prodrug: Design, Preparation, and Analysis of [(2-Sulfo)-9-fluorenylmethoxycarbonyl]3-Insulin", J. Med. Chem., vol. 43, pp. 2530-2537, (2000).
Greenwald, "Drug delivery systems: anticancer prodrugs and their polymeric conjugates", Exp. Opin. Ther. Patents, vol. 7, No. 6, pp. 601-609, (1997).
Harris, et al., "Effect of Pegylation on Pharmaceuticals", Nature Reviews/Drug Discovery, vol. 2, pp. 214-221, (Mar. 2003).
Kajigaeshi, et al., "Syntheses and Reactions of 1, 8-Disubstituted Fluorene Derivatives", Nippon Kagaku Kaishi (The Chemical Society of Japan), vol. 12, pp. 2052-2058, (1989). (English abstract attached).
Liu, et al., "A novel Fmoc-based anchorage for the synthesis of protected peptides on solid phase", Int. J. Peptide Protein Res., vol. 35, pp. 95-98, (1990).
Lottner, et al., "Hematoporphyrin-Derived Soluble Porphyrin-Platinum Conjugates with Combined Cytotoxic and Phototoxic Antitumor Activity", J. Med. Chem., pp. 2064-2078, (2002).
Ouchi, et al., "Design of Antitumor Agent-Terminated Poly(Ethylene Glycol) Conjugate as Macromolecular Prodrug", Polymer Preprints, vol. 38, No. 1, pp. 582-583, (1997).
Ouchi, et al., "Synthesis and Antitumor Activity of Poly(Ethylene Glycol)s Linked to 5-Fluorouracil via a Urethane or Urea Bond", Drug Design and Discovery, vol. 9, pp. 93-105, (1992).
Peleg-Shulman, et al., "Reversible PEGylation: A Novel Technology to Release Native Interferon α2 over a Prolonged Time Period", J. Med. Chem., vol. 47, pp. 4897-4904, (2004).
Shechter, et al., "Prolonging the half-life of human interferon-α2 in circulation: Design, preparation and analysis of (2-sulfo-9-fluorenylmethoxycarbonyl)7-interferon-α2", PNAS, vol. 98, No. 3, pp. 1212-1217, (Jan. 30, 2001).
Shechter, et al., "Reversible PEGylation of peptide YY3-36 prolongs its inhibition of food intake in mice", FEBS Letters, vol. 579, pp. 2439-2444, (2005).
Sims, et al., "A Method for the Estimation of Polyethylene Glycol in Plasma Protein Fractions", Analytical Biochemistry, vol. 107, pp. 60-63, (1980).
Suzuki, et al., "Replacement and Elimination of Bromine in Bromonitrofluorenones. The Preparation of 2,3- and 1,2,3-Substituted Fluorenes and Fluorenones", J. Org. Chem., vol. 26, pp. 2236-2239, (Jul. 1961).
Tsubery, et al., "Prolonging the Action of Protein and Peptide Drugs by a Novel Approach of Reversible Polyethylene Glycol Modification", The Journal of Biological Chemistry, vol. 279, No. 37, Issue of Sep. 10, 2004, pp. 38118-38124.
Weisburger, et al., "A New Route to 3- and 2,6-Substituted Fluorenes", J. Org. Chem., vol. 23, pp. 1193-1998, (Aug. 1958).
Weisburger, et al., "Synthesis of N-(8-Hydroxy-2-fluorenyl)acetamide", J. Org. Chem., vol. 20, pp. 1386-1387, (Dec. 1956).
Zalipsky, "Synthesis of an End-Group Functionalized Polyethylene Glycol-Lipid Conjugate for Preparation of Polymer-Grafted Liposomes", Bioconjugate Chem., vol. 4, pp. 296-299, (1993).
Zier, et al., "Polyethylene Glycol Bound Benzyl- and Fluorenyl Derivatives as Solubilizing Side-Chain Protecting Groups in Peptide Synthesis", Tetrahedron Letters, vol. 35, No. 7, pp. 1039-1042, (1994).
Zier, "Polyethylene glycol derivatives as protecting groups of amino acids, soluble and implementation strategies in the convergent synthesis of peptide", These De Doctorat, Universite de Lausanne, 142, pp., (1992). English Translation not available.
PCT International Search Report corresponding to PCT Application No. PCT/US2006/023504, filed Jun. 16, 2006, mailing date Oct. 8, 2007.
PCT Written Opinion of the International Searching Authority corresponding to PCT Application No. PCT/US2006/023504, filed Jun. 16, 2006, mailing date Jan. 3, 2008.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
NOF Corporation, PEG Derivatives, Phospholipid and Drug Delivery Materials for Pharmaceuticals, 46 pages, Catalogue 2003—1$^{st}$, (Jan. 2003).
NOF Corporation, PEG Derivatives, Phospholipid and Drug Delivery Materials for Pharmaceuticals, 27 pages, Catalogue 2003—2$^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
POLYPURE Products, PEG amines; PEG acids and amino acids; PEG thiols and disulfides; BIOTINS, 5 pages, (Apr. 2004).
POLYPURE Products, PEG amines; PEG acids and amino acids; PEG thiols and disulfides; BIOTINS, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).

Australian Examiner's First Report corresponding to Australian Patent Application No. 2006259225 dated May 17, 2011.

Chinese First Office Action corresponding to Chinese Patent Application No. 200680029849.5 dated Mar. 23, 2010.

European Communication corresponding to European Patent Application No. 06 773 353.5 dated Sep. 10, 2008.

European Communication corresponding to European Patent Application No. 06 773 353.5 dated Sep. 30, 2009.

European Communication corresponding to European Patent Application No. 06 773 353.5 dated Jan. 11, 2011.

European Search Report corresponding to European Patent Application No. 10184832.3-1216/2279758 dated Feb. 10, 2012.

Israel Office Action corresponding to Israel Patent Application No. 188012 dated Jun. 2010.

Israel Further Substantive Examination Report corresponding to Israel Patent Application No. 188012 dated May 19, 2011.

Indian First Examination Report corresponding to Indian Patent Application No. 28/DELNP/2008 dated Jun. 13, 2011.

Japanese Notice of Reasons for Rejection corresponding to Japanese Patent Application No. 2008-517149 mailed on Dec. 21, 2011.

Chinese Notification of the Second Office Action corresponding to Chinese Patent Application No. 200680029849.5 date of notification Jun. 20, 2012.

European Communication Extended Search Report corresponding to European Patent Application No. 10184832.3-1216 dated Feb. 10, 2012.

Israel further substantive Examination Report corresponding to Israeli Patent Application No. 188012 dated Jul. 15, 2012.

Mexican Official Letter corresponding to Mexico Patent Application No. MX/a/2007/016314 dated Dec. 22, 2011.

PHARMACEUTICAL COMPOSITIONS AND METHODS FOR DELIVERING SUCH COMPOSITIONS

CROSS-REFERENCE TO RELATED APPLICATIONS

This application is a continuation of U.S. patent application Ser. No. 11/454,971, filed Jun. 16, 2006, now U.S. Pat. No. 8,252,275, which claims the benefit of priority to the following provisional patent applications: U.S. Provisional Patent Application Ser. No. 60/691,516, filed Jun. 16, 2005; U.S. Provisional Patent Application Ser. No. 60/705,968, filed Aug. 4, 2005; U.S. Provisional Patent Application Ser. No. 60/751,082, filed Dec. 16, 2005; U.S. Provisional Patent Application Ser. No. 60/751,121, filed Dec. 16, 2005; and U.S. Provisional Patent Application Ser. No. 60/752,825, filed Dec. 21, 2005, the disclosures of which are incorporated herein by reference in their entireties.

BACKGROUND OF THE INVENTION

The present invention relates generally to polymeric reagents useful in providing a conjugate having a degradable linkage between a polymer and another moiety. In addition, the invention relates to, among other things, conjugates of the polymeric reagents, methods for synthesizing the polymeric reagents and methods for conjugating the polymeric reagents to active agents and other moieties.

BACKGROUND OF THE INVENTION

Scientists and clinicians face a number of challenges in their attempts to develop active agents into forms suited for delivery to a patient. Active agents that are polypeptides, for example, are often delivered via injection rather than orally. In this way, the polypeptide is introduced into the systemic circulation without exposure to the proteolytic environment of the stomach. Injection of polypeptides, however, has several drawbacks. For example, many polypeptides have a relatively short half-life, thereby necessitating repeated injections, which are often inconvenient and painful. Moreover, some polypeptides can elicit one or more immune responses with the consequence that the patient's immune system attempts to destroy or otherwise neutralize the immunogenic polypeptide. Of course, once the polypeptide has been destroyed or otherwise neutralized, the polypeptide cannot exert its intended pharmacodynamic activity. Thus, delivery of active agents such as polypeptides is often problematic even when these agents are administered by injection.

Some success has been achieved in addressing the problems of delivering active agents via injection. For example, conjugating the active agent to a water-soluble polymer has resulted in polymer-active agent conjugates having reduced immunogenicity and antigenicity. In addition, these polymer-active agent conjugates often have greatly increased half-lives compared to their unconjugated counterparts as a result of decreased clearance through the kidney and/or decreased enzymatic degradation in the systemic circulation. As a result of having a greater half-life, the polymer-active agent conjugate requires less frequent dosing, which in turn reduces the overall number of painful injections and inconvenient visits with a health care professional. Moreover, active agents that were only marginally soluble demonstrate a significant increase in water solubility when conjugated to a water-soluble polymer.

Due to its documented safety as well as its approval by the FDA for both topical and internal use, polyethylene glycol has been conjugated to active agents. When an active agent is conjugated to a polymer of polyethylene glycol or "PEG," the conjugated active agent is conventionally referred to as "PEGylated." The commercial success of PEGylated active agents such as PEGASYS® PEGylated interferon alpha-2a (Hoffmann-La Roche, Nutley, N.J.), PEG-INTRON® PEGylated interferon alpha-2b (Schering Corp., Kennilworth, N.J.), and NEULASTA™ PEG-filgrastim (Amgen Inc., Thousand Oaks, Calif.) demonstrates that administration of a conjugated form of an active agent can have significant advantages over the unconjugated counterpart. Small molecules such as distearoylphosphatidylethanolamine (Zalipsky (1993) *Bioconjug. Chem.* 4(4):296-299) and fluorouracil (Ouchi et al. (1992) *Drug Des. Discov.* 9(1):93-105) have also been PEGylated. Harris et al. have provided a review of the effects of PEGylation on pharmaceuticals. Harris et al. (2003) *Nat. Rev. Drug Discov.* 2(3):214-221.

Despite these successes, conjugation of a polymer to an active agent to result in a commercially relevant drug is often challenging. For example, conjugation can result in the polymer being attached at or near a site on the active agent that is necessary for pharmacologic activity (e.g., at or near a binding site). Such conjugates may therefore have unacceptably low activity due to, for example, the steric effects introduced by the polymer. Attempts to remedy conjugates having unacceptably low activity can be frustrated when the active agent has few or no other sites suited for attachment to a polymer. Thus, additional PEGylation alternatives have been desired.

One suggested approach for solving this and other problems is "reversible PEGylation" wherein the native active agent (or a moiety having increased activity compared to the PEGylated active agent) is released. For example, U.S. Patent Application Publication No. 2005/0079155 describes conjugates using reversible linkages. As described in this publication, reversible linkages can be effected through the use of an enzyme substrate moiety. It has been pointed out, however, that approaches relying on enzymatic activity are dependent on the availability of enzymes. See Peleg-Schulman (2004) *J. Med. Chem.* 47:4897-4904. Thus, additional approaches that do not rely on enzymatic processes for degradation have been described as being desirable.

One such approach for reversible PEGylation describes a polymeric reagent comprising a fluorene moiety upon which a branched polymer is attached using maleimide chemistry. Id. See Peleg-Schulman (2004) *J. Med. Chem.* 47:4897-4904 and WO 2004/089280. The synthetic approach used to form the described polymeric reagent is complex, requiring many steps. Consequently, alternative polymeric reagents that do not require such complex synthetic schemes are needed.

Another reversible conjugation approach is described in U.S. Pat. No. 6,514,491. The structures described in this patent include those wherein a water soluble, non-peptidic polymer is attached to an aromatic group via a single attachment point. Although providing degradable linkages within the conjugate, there is a need to provide still further polymeric reagents that can form degradable linkages with a conjugate.

Thus, further polymeric reagents useful in providing conjugates having a degradable linkage between a polymer and another moiety remains needed. In addition, there remains a need to provide a range of polymeric reagents useful in providing conjugates having a range of release rates. Thus, the present invention seeks to solve these and other needs in the art.

SUMMARY OF THE INVENTION

In one or more embodiments of the invention, a polymeric reagent of the following formula is provided:

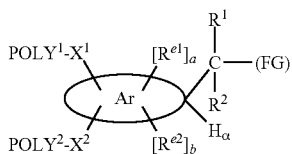

(Formula I)

wherein:
POLY$^1$ is a first water-soluble polymer;
POLY$^2$ is a second water-soluble polymer;
X$^1$ is a first spacer moiety;
X$^2$ is a second spacer moiety;

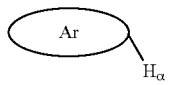

is an aromatic-containing moiety bearing an ionizable hydrogen atom, H$_\alpha$;
R$^1$ is H or an organic radical;
R$^2$ is H or an organic radical;
(a) is either zero or one;
(b) is either zero or one;
R$^{e1}$, when present, is a first electron altering group;
R$^{e2}$, when present, is a second electron altering group; and
(FG) is a functional group capable of reacting with an amino group of an active agent to form a degradable linkage, such as a carbamate linkage.

In one or more embodiments of the present invention, a polymeric reagent of the following formula is provided:

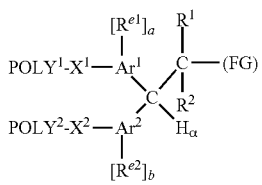

(Formula II)

wherein:
POLY$^1$ is a first water-soluble polymer;
POLY$^2$ is a second water-soluble polymer;
X$^1$ is a first spacer moiety;
X$^2$ is a second spacer moiety;
Ar$^1$ is a first aromatic moiety;
Ar$^2$ is a second aromatic moiety;
H$_\alpha$ is an ionizable hydrogen atom;
R$^1$ is H or an organic radical;
R$^2$ is H or an organic radical;
(a) is either zero or one;
(b) is either zero or one;
R$^{e1}$, when present, is a first electron altering group;
R$^{e2}$, when present, is a second electron altering group; and
(FG) is a functional group capable of reacting with an amino group of an active agent to form a degradable linkage, such as a carbamate linkage.

In one or more embodiments of the present invention, a polymeric reagent of the following formula is provided:

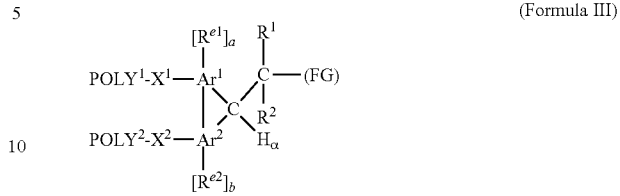

(Formula III)

wherein:
POLY$^1$ is a first water-soluble polymer;
POLY$^2$ is a second water-soluble polymer;
X$^1$ is a first spacer moiety;
X$^2$ is a second spacer moiety;
Ar$^1$ is a first aromatic moiety;
Ar$^2$ is a second aromatic moiety;
H$_\alpha$ is an ionizable hydrogen atom;
R$^1$ is H or an organic radical;
R$^2$ is H or an organic radical;
(a) is either zero or one;
(b) is either zero or one;
R$^{e1}$, when present, is a first electron altering group;
R$^{e2}$, when present, is a second electron altering group; and
(FG) is a functional group capable of reacting with an amino group of an active agent to form a degradable linkage, such as a carbamate linkage.

In one or more embodiments of the present invention, a polymeric reagent of the following formula is provided:

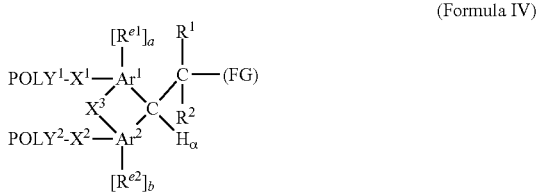

(Formula IV)

wherein:
POLY$^1$ is a first water-soluble polymer;
POLY$^2$ is a second water-soluble polymer;
X$^1$ is a first spacer moiety;
X$^2$ is a second spacer moiety;
X$^3$ is a third spacer moiety;
Ar$^1$ is a first aromatic moiety;
Ar$^2$ is a second aromatic moiety;
H$_\alpha$ is an ionizable hydrogen atom;
R$^1$ is H or an organic radical;
R$^2$ is H or an organic radical;
(a) is either zero or one;
(b) is either zero or one;
R$^{e1}$, when present, is a first electron altering group;
R$^{e2}$, when present, is a second electron altering group; and
(FG) is a functional group capable of reacting with an amino group of an active agent to form a degradable linkage, such as a carbamate linkage.

In one or more embodiments of the present invention, a polymeric reagent of the following formula is provided:

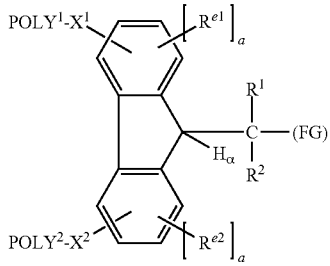

(Formula V)

wherein:
POLY¹ is a first water-soluble polymer;
POLY² is a second water-soluble polymer;
X¹ is a first spacer moiety;
X² is a second spacer moiety;
$H_\alpha$ is an ionizable hydrogen atom;
$R^1$ is H or an organic radical;
$R^2$ is H or an organic radical;
(a) is either zero or one;
(b) is either zero or one;
$R^{e1}$, when present, is a first electron altering group;
$R^{e2}$, when present, is a second electron altering group; and
(FG) is a functional group capable of reacting with an amino group of an active agent to form a degradable linkage, such as a carbamate linkage.

In one or more embodiments of the invention, a polymeric reagent of the following formula is provided:

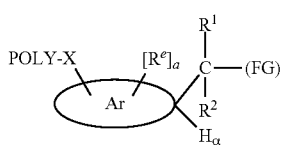

(Formula VI)

wherein:
POLY is a water-soluble polymer;
X is a spacer moiety that does not include a

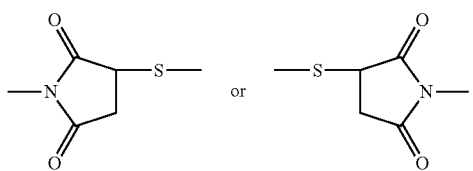

moiety;

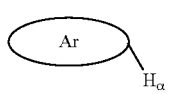

is an aromatic moiety bearing an ionizable hydrogen atom, $H_\alpha$;

$R^1$ is H or an organic radical;
$R^2$ is H or an organic radical;
(a) is either zero or one;
$R^e$, when present, is an electron altering group; and
(FG) is a functional group capable of reacting with an amino group of an active agent to form a degradable linkage, such as a carbamate linkage.

In one or more embodiments of the invention, a conjugate of the following formula is provided:

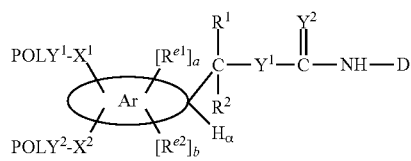

(Formula I-C)

wherein:
POLY¹ is a first water-soluble polymer;
POLY² is a second water-soluble polymer;
X¹ is a first spacer moiety;
X² is a second spacer moiety;

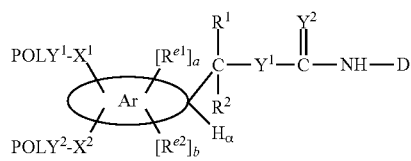

is an aromatic-containing moiety bearing an ionizable hydrogen atom, $H_\alpha$;
$R^1$ is H or an organic radical;
$R^2$ is H or an organic radical;
(a) is either zero or one;
(b) is either zero or one;
$R^{e1}$, when present, is a first electron altering group;
$R^{e2}$, when present, is a second electron altering group;
$Y^1$ is O or S;
$Y^2$ is O or S; and
D is a residue of a biologically active agent.

In one or more embodiments of the present invention, a conjugate of the following formula is provided:

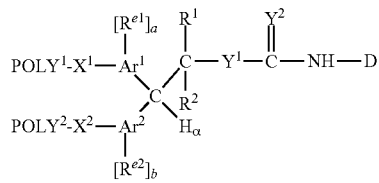

(Formula II-C)

wherein:
POLY¹ is a first water-soluble polymer;
POLY² is a second water-soluble polymer;
X¹ is a first spacer moiety;
X² is a second spacer moiety;
$Ar^1$ is a first aromatic moiety;
$Ar^2$ is a second aromatic moiety;
$H_\alpha$ is an ionizable hydrogen atom;
$R^1$ is H or an organic radical;
$R^2$ is H or an organic radical;
(a) is either zero or one;
(b) is either zero or one;
$R^{e1}$, when present, is a first electron altering group;
$R^{e2}$, when present, is a second electron altering group;

$Y^1$ is O or S;
$Y^2$ is O or S; and
D is a residue of a biologically active agent.

In one or more embodiments of the present invention, a conjugate of the following formula is provided:

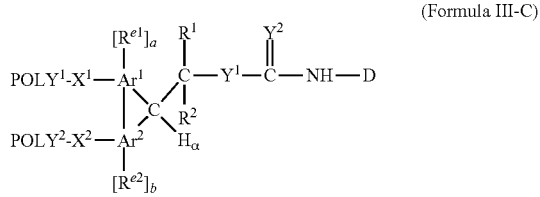
(Formula III-C)

wherein:
POLY$^1$ is a first water-soluble polymer;
POLY$^2$ is a second water-soluble polymer;
$X^1$ is a first spacer moiety;
$X^2$ is a second spacer moiety;
Ar$^1$ is a first aromatic moiety;
Ar$^2$ is a second aromatic moiety;
$H_\alpha$ is an ionizable hydrogen atom;
$R^1$ is H or an organic radical;
$R^2$ is H or an organic radical;
(a) is either zero or one;
(b) is either zero or one;
$R^{e1}$, when present, is a first electron altering group;
$R^{e2}$, when present, is a second electron altering group;
$Y^1$ is O or S;
$Y^2$ is O or S; and
D is a residue of a biologically active agent.

In one or more embodiments of the present invention, a conjugate is provided comprising the structure:

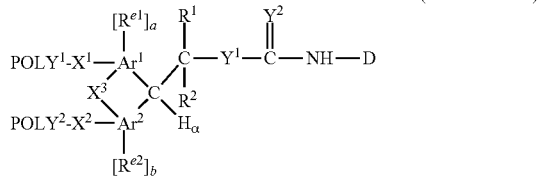
(Formula IV-C)

wherein:
POLY$^1$ is a first water-soluble polymer;
POLY$^2$ is a second water-soluble polymer;
$X^1$ is a first spacer moiety;
$X^2$ is a second spacer moiety;
$X^3$ is a third spacer moiety;
Ar$^1$ is a first aromatic moiety;
Ar$^2$ is a second aromatic moiety;
$H_\alpha$ is an ionizable hydrogen atom;
$R^1$ is H or an organic radical;
$R^2$ is H or an organic radical;
(a) is either zero or one;
(b) is either zero or one;
$R^{e1}$, when present, is a first electron altering group;
$R^{e2}$, when present, is a second electron altering group;
$Y^1$ is O or S;
$Y^2$ is O or S; and
D is a residue of a biologically active agent.

In one or more embodiments of the present invention, a conjugate is provided comprising the structure:

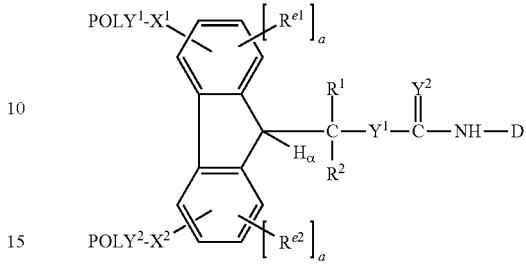
(Formula V-C)

POLY$^1$ is a first water-soluble polymer;
POLY$^2$ is a second water-soluble polymer;
$X^1$ is a first spacer moiety;
$X^2$ is a second spacer moiety;
$H_\alpha$ is an ionizable hydrogen atom;
$R^1$ is H or an organic radical;
$R^2$ is H or an organic radical;
(a) is either zero or one;
(b) is either zero or one;
$R^{e1}$, when present, is a first electron altering group;
$R^{e2}$, when present, is a second electron altering group;
$Y^1$ is O or S;
$Y^2$ is O or S; and
D is a residue of a biologically active agent.

In one or more embodiments of the invention, a conjugate is provided comprising the following structure:

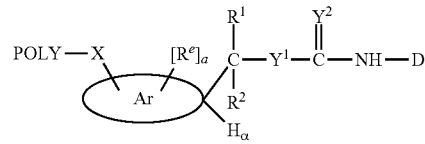
(Formula VI-C)

wherein:
POLY is a water-soluble polymer;
X is a spacer moiety that does not include a

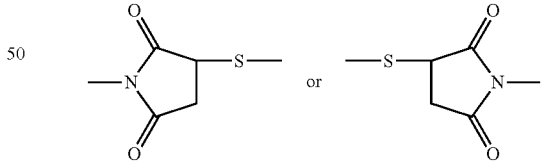

moiety;

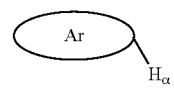

is an aromatic moiety bearing an ionizable hydrogen atom, $H_\alpha$;
$R^1$ is H or an organic radical;
$R^2$ is H or an organic radical;
(a) is either zero or one;
$R^e$, when present, is an electron altering group;

$Y^1$ is O or S;
$Y^2$ is O or S; and
D is a residue of a biologically active agent.

In one or more embodiments of the invention, a method for preparing a polymeric reagent is provided, the method comprising:

(a) providing an aromatic moiety bearing a first attachment site, a second attachment site, optional third attachment site, and optional additional attachment sites;

(b) reacting a functional group reagent with the first attachment site to result in the first attachment site bearing a functional group capable of reacting with an amino group of an active agent and result in a releaseable linkage, such as a carbamate linkage;

(c) reacting a water-soluble polymer bearing a reactive group with the second attachment site and, when present, the optional third attachment site to result in (i) the second attachment site bearing a water-soluble polymer through a spacer moiety, wherein the spacer moiety does not include a

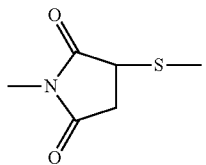

moiety, and (ii) the optional third attachment site, when present, bearing a second water-soluble polymer through a spacer moiety, wherein the spacer moiety does not include a not include a

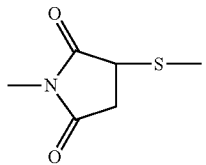

moiety.

In one or more embodiments of the invention, a polymeric reagent prepared in accordance with the described methods for preparing polymeric reagents is provided.

In one or more embodiments of the invention, methods for preparing conjugates are provided.

In one or more embodiments of the invention, conjugates prepared using the novel polymeric reagents described herein are provided.

In one or more embodiments of the invention, pharmaceutical preparations comprising the conjugates are provided.

In one or more embodiments of the invention, methods for administering the conjugates are provided.

DETAILED DESCRIPTION OF THE INVENTION

Figure 1:
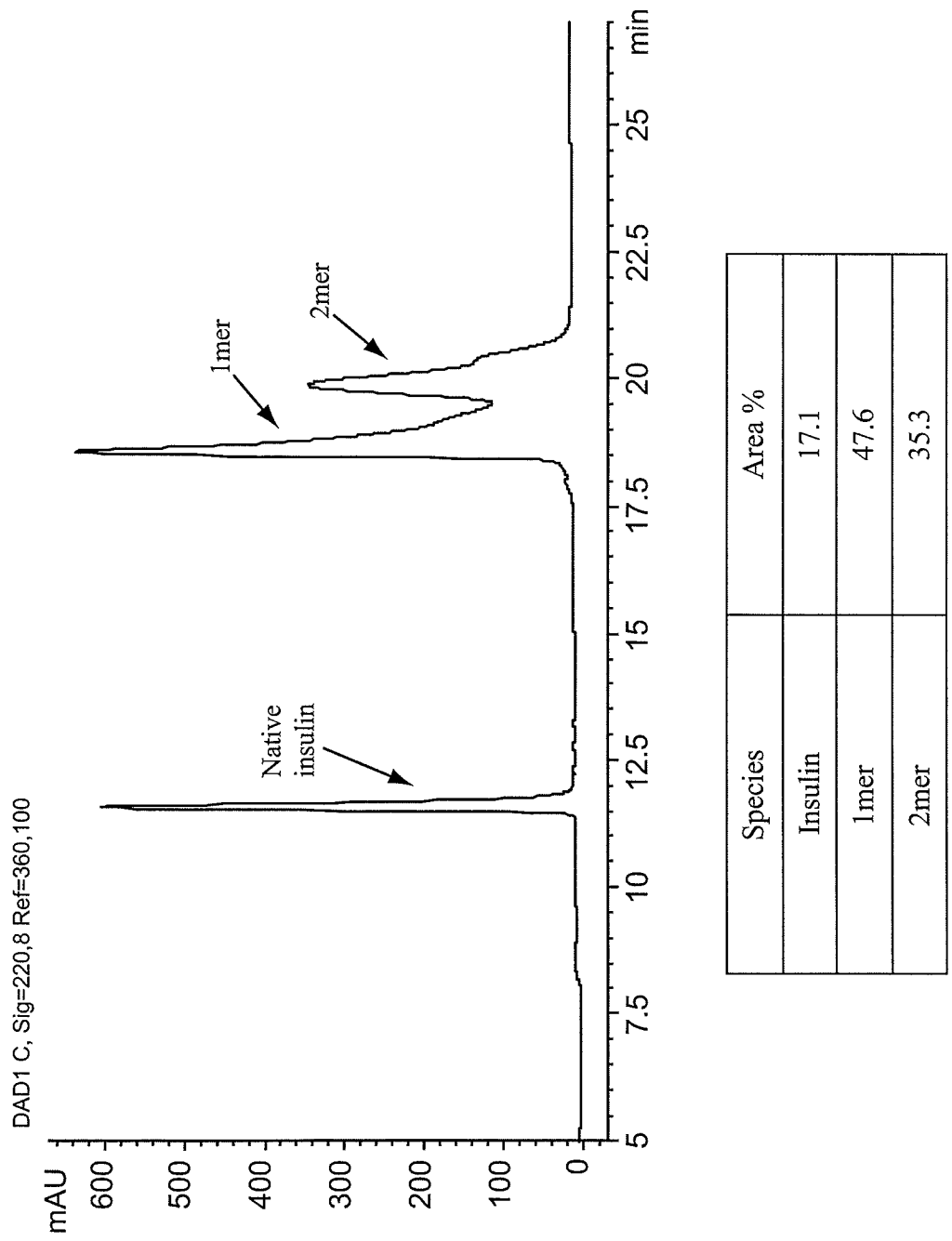
FIG. 1 is an HPLC chromatogram of the reaction mixture of insulin and the polymeric reagent prepared as described in Example 2.

Before describing the present invention in detail, it is to be understood that this invention is not limited to the particular polymers, synthetic techniques, active agents, and the like, as such may vary.

It must be noted that, as used in this specification and the claims, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

In describing and claiming the present invention, the following terminology will be used in accordance with the definitions described below.

"PEG," "polyethylene glycol" and "poly(ethylene glycol)" as used herein, are meant to encompass any water-soluble poly(ethylene oxide). Typically, PEGs for use in accordance with the invention comprise the following structure "—O(CH$_2$CH$_2$O)$_m$—" where (m) is 2 to 4000. As used herein, PEG also includes "—CH$_2$CH$_2$—O(CH$_2$CH$_2$O)$_m$—CH$_2$CH$_2$—" and "—(CH$_2$CH$_2$O)$_m$—," depending upon whether or not the terminal oxygens have been displaced. When the PEG further comprises a spacer moiety (to be described in greater detail below), the atoms comprising the spacer moiety, when covalently attached to a water-soluble polymer segment, do not result in the formation of an oxygen-oxygen bond (i.e., an "—O—O—" or peroxide linkage). Throughout the specification and claims, it should be remembered that the term "PEG" includes structures having various terminal or "end capping" groups and so forth. The term "PEG" also means a polymer that contains a majority, that is to say, greater than 50%, of —CH$_2$CH$_2$O— monomeric subunits. With respect to specific forms, the PEG can take any number of a variety of molecular weights, as well as structures or geometries such as "branched," "linear," "forked," "multifunctional," and the like, to be described in greater detail below.

The terms "end-capped" or "terminally capped" are interchangeably used herein to refer to a terminal or endpoint of a polymer having an end-capping moiety. Typically, although not necessarily, the end-capping moiety comprises a hydroxy or C$_{1-20}$ alkoxy group. Thus, examples of end-capping moieties include alkoxy (e.g., methoxy, ethoxy and benzyloxy), as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled to can be determined by using a suitable detector. Such labels include, without limitation, fluorescers, chemiluminescers, moieties used in enzyme labeling, colorimetric (e.g., dyes), metal ions, radioactive moieties, and the like. Suitable detectors include photometers, films, spectrometers, and the like.

"Non-naturally occurring" with respect to a polymer or water-soluble polymer means a polymer that in its entirety is not found in nature. A non-naturally occurring polymer or water-soluble polymer may, however, contain one or more subunits or portions of a subunit that are naturally occurring, so long as the overall polymer structure is not found in nature.

The term "water-soluble polymer" is any polymer that is soluble in water at room temperature. Typically, a water-soluble polymer will transmit at least about 75%, more preferably at least about 95% of light, transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is still more preferred, however, that the water-soluble polymer is about 95% (by weight) soluble in water and most preferred that the water-soluble polymer is completely soluble in water.

Molecular weight in the context of a water-soluble polymer of the invention, such as PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques. Other methods for measuring molecular weight values can also be used, such as the use of end-group analysis or the measurement of colligative properties (e.g., freezing-pint depression, boiling-point elevation, or osmotic pressure) to determine number average molecular weight or the use of light scattering techniques, ultracentrifugation or viscometry to determine weight average molecular weight. The polymers of the invention are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

As used herein, the term "carboxylic acid" is a moiety having a

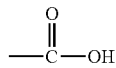

functional group [also represented as a "—COOH" or —C(O)OH], as well as moieties that are derivatives of a carboxylic acid, such derivatives including, for example, protected carboxylic acids. Thus, unless the context clearly dictates otherwise, the term carboxylic acid includes not only the acid form, but corresponding esters and protected forms as well. With regard to protecting groups suited for a carboxylic acid and any other functional group described herein, reference is made to Greene et al., "PROTECTIVE GROUPS IN ORGANIC SYNTHESIS" 3$^{rd}$ Edition, John Wiley and Sons, Inc., New York, 1999.

The term "reactive" or "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "nonreactive" or "inert" group).

The terms "protected" or "protecting group" or "protective group" refer to the presence of a moiety (i.e., the protecting group) that prevents or blocks reaction of a particular chemically reactive functional group in a molecule under certain reaction conditions. The protecting group will vary depending upon the type of chemically reactive functional group being protected as well as the reaction conditions to be employed and the presence of additional reactive or protecting groups in the molecule, if any. Protecting groups known in the art can be found in Greene et al., supra.

As used herein, the term "functional group" or any synonym thereof is meant to encompass protected forms thereof.

The terms "spacer" or "spacer moiety" are used herein to refer to an atom or a collection of atoms optionally used to link one moiety to another, such as a water-soluble polymer segment to an aromatic-containing moiety. The spacer moieties of the invention may be hydrolytically stable or may include one or more physiologically hydrolyzable or enzymatically degradable linkages.

An "organic radical" as used includes, for example, alkyl, substituted alkyl, alkenyl, substituted alkenyl, alkynyl, substituted alkynyl, aryl and substituted aryl.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include ethyl, propyl, butyl, pentyl, 1-methylbutyl, 1-ethylpropyl, 3-methylpentyl, and the like. As used herein, "alkyl" includes cycloalkyl when three or more carbon atoms are referenced and lower alkyl.

"Lower alkyl" refers to an alkyl group containing from 1 to 6 carbon atoms, and may be straight chain or branched, as exemplified by methyl, ethyl, n-butyl, iso-butyl, and tert-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8.

"Non-interfering substituents" are those groups that, when present in a molecule, are typically non-reactive with other functional groups contained within the molecule.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy, lower phenyl (e.g., 0-2 substituted phenyl); substituted phenyl; and the like. "Substituted aryl" is aryl having one or more non-interfering groups as a substituent. For substitutions on a phenyl ring, the substituents may be in any orientation (i.e., ortho, meta, or para).

"Alkoxy" refers to an —O—R group, wherein R is alkyl or substituted alkyl, preferably $C_1$-$C_{20}$ alkyl (e.g., methoxy, ethoxy, propyloxy, benzyl, etc.), preferably $C_1$-$C_7$ alkyl.

As used herein, "alkenyl" refers to a branched or unbranched hydrocarbon group of 1 to 15 atoms in length, containing at least one double bond, such as ethenyl, n-propenyl, isopropenyl, n-butenyl, isobutenyl, octenyl, decenyl, tetradecenyl, and the like.

The term "alkynyl" as used herein refers to a branched or unbranched hydrocarbon group of 2 to 15 atoms in length, containing at least one triple bond, ethynyl, n-butynyl, isopentynyl, octynyl, decynyl, and so forth.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl. An aromatic moiety (e.g., $Ar^1$, $Ar^2$, and so forth), means a structure containing aryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen.

"Substituted heteroaryl" is heteroaryl having one or more non-interfering groups as substituents.

"Substituted heterocycle" is a heterocycle having one or more side chains formed from non-interfering substituents.

"Electrophile" refers to an ion or atom or collection of atoms, that may be ionic, having an electrophilic center, i.e., a center that is electron seeking, capable of reacting with a nucleophile.

"Nucleophile" refers to an ion or atom or collection of atoms that may be ionic having a nucleophilic center, i.e., a center that is seeking an electrophilic center or with an electrophile.

A "physiologically cleavable" or "hydrolyzable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include, but are not limited to, carboxylate ester, phosphate ester, anhydrides, acetals, ketals, acyloxyalkyl ether, imines, ortho esters, peptides and oligonucleotides.

A "degradable linkage" includes, but is not limited to, a physiologically cleavable bond, a hydrolyzable bond, and an enzymatically degradable linkage. Thus, a "degradable linkage" is a linkage that may undergo either hydrolysis or cleavage by some other mechanism (e.g., enzyme-catalyzed, acid-catalyzed, base-catalyzed, and so forth) under physiological conditions. For example, a "degradable linkage" can involve an elimination reaction that has a base abstraction of a proton, (e.g., an ionizable hydrogen atom, $H_\alpha$), as the driving force.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes (carbamates), and the like. Generally, a hydrolytically stable linkage is one that exhibits a rate of hydrolysis of less than about 1-2% per day under physiological conditions. Hydrolysis rates of representative chemical bonds can be found in most standard chemistry textbooks. It must be pointed out that some linkages can be hydrolytically stable or hydrolyzable, depending upon (for example) adjacent and neighboring atoms and ambient conditions. One of ordinary skill in the art can determine whether a given linkage or bond is hydrolytically stable or hydrolyzable in a given context by, for example, placing a linkage-containing molecule of interest under conditions of interest and testing for evidence of hydrolysis (e.g., the presence and amount of two molecules resulting from the cleavage of a single molecule). Other approaches known to those of ordinary skill in the art for determining whether a given linkage or bond is hydrolytically stable or hydrolyzable can also be used.

The terms "active agent," "biologically active agent" and "pharmacologically active agent" are used interchangeably herein and are defined to include any agent, drug, compound, composition of matter or mixture that provides some pharmacologic, often beneficial, effect that can be demonstrated in vivo or in vitro. This includes foods, food supplements, nutrients, nutriceuticals, drugs, proteins, vaccines, antibodies, vitamins, and other beneficial agents. As used herein, these terms further include any physiologically or pharmacologically active substance that produces a localized or systemic effect in a patient.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of a polymer-active agent conjugate—typically present in a pharmaceutical preparation—that is needed to provide a desired level of active agent and/or conjugate in the bloodstream or in a target tissue. The exact amount will depend upon numerous factors, e.g., the particular active agent, the components and physical characteristics of the pharmaceutical preparation, intended patient population, patient considerations, and the like, and can readily be determined by one of ordinary skill in the art, based upon the information provided herein and available in the relevant literature.

"Multifunctional" in the context of a polymer of the invention means a polymer having 3 or more functional groups contained therein, where the functional groups may be the same or different. Multifunctional polymers of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer. A "difunctional" polymer means a polymer having two functional groups contained therein, either the same (i.e., homodifunctional) or different (i.e., heterodifunctional).

"Branched," in reference to the geometry or overall structure of a polymer, refers to polymer having 2 or more polymer "arms." A branched polymer may possess 2 polymer arms, 3 polymer arms, 4 polymer arms, 6 polymer arms, 8 polymer arms or more. One particular type of highly branched polymer is a dendritic polymer or dendrimer, which, for the purposes of the invention, is considered to possess a structure distinct from that of a branched polymer.

A "dendrimer" or dendritic polymer is a globular, size monodisperse polymer in which all bonds emerge radially from a central focal point or core with a regular branching pattern and with repeat units that each contribute a branch point. Dendrimers exhibit certain dendritic state properties such as core encapsulation, making them unique from other types of polymers.

A basic or acidic reactant described herein includes neutral, charged, and any corresponding salt forms thereof.

The term "patient," refers to a living organism suffering from or prone to a condition that can be prevented or treated by administration of a conjugate as provided herein, and includes both humans and animals.

As used herein, the term "ionizable hydrogen atom" ("$H_\alpha$") means a hydrogen atom that can be removed in the presence of a base, often a hydroxide or amine base. Typically, the "ionizable hydrogen atom" ("$H_\alpha$") will be a hydrogen atom attached to a carbon atom that, in turn, is attached to one or more aromatic moieties or another group or groups that in some way stabilize the carbanion that would form from loss of the ionizable hydrogen atom as a proton (or the transition state leading to said carbanion).

As used herein, "drug release rate" means a rate (stated as a half-life) in which half of the total amount of polymer-active agent conjugates in a system will cleave into the active agent and a polymeric residue.

"Optional" and "optionally" mean that the subsequently described circumstance may or may not occur, so that the description includes instances where the circumstance occurs and instances where it does not.

As used herein, the "halo" designator (e.g., fluoro, chloro, iodo, bromo, and so forth) is generally used when the halogen is attached to a molecule, while the suffix "ide" (e.g., fluoride, chloride, iodide, bromide, and so forth) is used when the halogen exists in its independent ionic form (e.g., such as when a leaving group leaves a molecule).

In the context of the present discussion, it should be recognized that the definition of a variable provided with respect to one structure or formula is applicable to the same variable repeated in a different structure, unless the context dictates otherwise. Thus, for example, the definition of "POLY," "spacer moiety," "$R^{e1}$" and so forth with respect to a polymeric reagent is equally applicable to a conjugate provided herein.

As previously stated, the present invention comprises (among other things) polymeric reagents useful in providing conjugates having a degradable linkage between a polymer and another moiety. Without wishing to be bound by theory, it is believed that the conjugates are believed to degrade in such as way as to minimize or eliminate entirely any residue or "tag" of the polymeric reagent used to form the conjugate. As a consequence, it is possible—upon hydrolysis of a conjugate formed from the reaction of a polymeric reagent described herein with an amine-containing active agent—to regenerate or recover the original unconjugated and unmodified form of the active agent.

As discussed herein and as evidenced by the formulae provided herein, the polymeric reagents of the invention comprise one or more water-soluble polymers (e.g., "POLY$^1$" and "POLY$^2$" as set forth in various formulae provided herein), an aromatic-containing moiety bearing an ionizable hydrogen atom, $H_\alpha$; (e.g.,

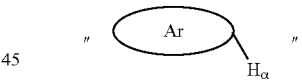

as set forth in various formulae provided herein), and a functional group capable of reacting with an amino group of an active agent to form a degradable linkage [e.g., "(FG)" as set forth in various formulae provided herein]. In addition, various components of the described polymeric reagents can be attached to the rest of the polymeric reagent through an optional spacer moiety (e.g., as "X", "$X^1$", "$X^2$" and "$X^3$" as set forth in various formulae provided herein). In addition one, two, three, four or more electron altering groups (e.g., "$R^e$", "$R^{e1}$", "$R^{e2}$", "$R^{e3}$", "$R^{e4}$" and so forth as set forth in various formulae provided herein) can be attached to the aromatic-containing moiety (in both the polymeric reagent as well as the conjugate).

Before describing exemplary polymeric reagents of the invention, embodiments of a water-soluble polymer, an aromatic moiety, a functional group capable of reacting with an amino group of an active agent to form a degradable linkage, such as a carbamate linkage, an electron altering group, and a spacer moiety will first be discussed. The following descriptions of a water-soluble polymer, an aromatic moiety, an electron altering group, and a spacer moiety are applicable not only to the polymeric reagent, but to the corresponding conjugates formed using the described polymeric reagents.

With respect to a given water-soluble polymer, each water-soluble polymer (e.g., POLY, POLY$^1$ and POLY$^2$) can comprise any polymer so long as the polymer is water-soluble and non-peptidic. Although preferably a poly(ethylene glycol), a water-soluble polymer for use herein can be, for example, other water-soluble polymers such as other poly(alkylene glycols), such as poly(propylene glycol) ("PPG"), copolymers of ethylene glycol and propylene glycol and the like, poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine), such as described in U.S. Pat. No. 5,629,384. The water soluble polymer can be a homopolymer, copolymer, terpolymer, nonrandom block polymer, and random block polymer of any of the foregoing. In addition, a water-soluble polymer can be linear, but can also be in other forms (e.g., branched, forked, and the like) as will be described in further detail below. In the context of being present within an overall structure, a water-soluble polymer has from 1 to about 300 termini.

In instances where the polymeric reagent comprises two or more water-soluble polymers, each water-soluble polymer in the overall structure can be the same or different. It is preferred, however, that all water-soluble polymers in the overall structure are of the same type. For example, it is preferred that all water-soluble polymers within a given structure are each a poly(ethylene glycol).

Although the weight average molecular weight of any individual water-soluble polymer can vary, the weight average molecular weight of any given water-soluble polymer will typically be in the following range: 100 Daltons to about 150,000 Daltons. Exemplary ranges, however, include weight-average molecular weights in the following ranges: about 880 Daltons to about 5,000 Daltons; in the range of greater than 5,000 Daltons to about 100,000 Daltons; in the range of from about 6,000 Daltons to about 90,000 Daltons; in the range of from about 10,000 Daltons to about 85,000 Daltons; in the range of greater than 10,000 Daltons to about 85,000 Daltons; in the range of from about 20,000 Daltons to about 85,000 Daltons; in the range of from about 53,000 Daltons to about 85,000 Daltons; in the range of from about 25,000 Daltons to about 120,000 Daltons; in the range of from about 29,000 Daltons to about 120,000 Daltons; in the range of from about 35,000 Daltons to about 120,000 Daltons; in the range of about 880 Daltons to about 60,000 Daltons; in the range of about 440 Daltons to about 40,000 Daltons; in the range of about 440 Daltons to about 30,000 Daltons; and in the range of from about 40,000 Daltons to about 120,000 Daltons. For any given water-soluble polymer, PEGs having a molecular weight in one or more of these ranges are preferred.

Exemplary weight-average molecular weights for the water-soluble polymer include about 100 Daltons, about 200 Daltons, about 300 Daltons, about 400 Daltons, about 440 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 16,000 Daltons, about 17,000 Daltons, about 18,000 Daltons, about 19,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched versions of the water-soluble polymer (e.g., a branched 40,000 Dalton water-soluble polymer comprised of two 20,000 Dalton polymers) having a total weight average molecular weight of any of the foregoing can also be used.

In one or more embodiments of the invention, the polymeric reagent will comprise a water-soluble polymer having a size in the range suited for the desired rate of release of the conjugate formed therefrom. For example, a conjugate having a relatively long release rate can be prepared from a polymeric reagent having a size suited for (a) extended circulation prior to degradation of the conjugate, and (b) moderately rapid in vivo clearance of the water-soluble polymer remainder upon degradation of the conjugate. Likewise, when the conjugate has a relatively fast release rate, then the polymeric reagent would typically have a lower molecular weight.

When a PEG is used as the water-soluble polymer in the polymeric reagent, the PEG typically comprises a number of (OCH$_2$CH$_2$) monomers [or (CH$_2$CH$_2$O) monomers, depending on how the PEG is defined]. As used throughout the description, the number of repeating units is identified by the subscript "n" in "(OCH$_2$CH$_2$)." Thus, the value of (n) typically falls within one or more of the following ranges: from 2 to about 3400, from about 4 to about 1500, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer.

Each water-soluble polymer is typically biocompatible and non-immunogenic. With respect to biocompatibility, a substance is considered biocompatible if the beneficial effects associated with use of the substance alone or with another substance (e.g., an active agent) in connection with living tissues (e.g., administration to a patient) outweighs any deleterious effects as evaluated by a clinician, e.g., a physician. With respect to non-immunogenicity, a substance is considered non-immunogenic if use of the substance alone or with another substance in connection with living tissues does not produce an immune response (e.g., the formation of antibodies) or, if an immune response is produced, that such a response is not deemed clinically significant or important as evaluated by a clinician. It is particularly preferred that the water-soluble polymers, described herein as well as conjugates of active agents and the polymers are biocompatible and non-immunogenic.

In one form useful, free or nonbound PEG is a linear polymer terminated at each end with hydroxyl groups:

wherein (m') typically ranges from zero to about 4,000, preferably from about 20 to about 1,000.

The above polymer, alpha-,omega-dihydroxylpoly(ethylene glycol), can be represented in brief form as HO-PEG-OH where it is understood that the -PEG- symbol can represent the following structural unit:

—CH$_2$CH$_2$O—(CH$_2$CH$_2$O)$_{m'}$—CH$_2$CH$_2$— where (m') is as defined as above.

Another type of free or nonbound PEG useful in the present invention is methoxy-PEG-OH, or mPEG in brief, in which one terminus is the relatively inert methoxy group, while the other terminus is a hydroxyl group. The structure of mPEG is given below.

CH$_3$O—CH$_2$CH$_2$O—(CH$_2$CH$_2$O)$_{m'}$—CH$_2$CH$_2$— where (m') is as described above.

Multi-armed or branched PEG molecules, such as those described in U.S. Pat. No. 5,932,462, can also be used as the PEG polymer. For example, PEG can have the structure:

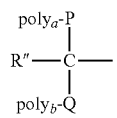

wherein:
poly$_a$ and poly$_b$ are PEG backbones (either the same or different), such as methoxy poly(ethylene glycol);
R" is a nonreactive moiety, such as H, methyl or a PEG backbone; and
P and Q are nonreactive linkages. In a preferred embodiment, the branched PEG polymer is methoxy poly(ethylene glycol) disubstituted lysine.

In addition, the PEG can comprise a forked PEG. An example of a free or nonbound forked PEG is represented by the following formula:

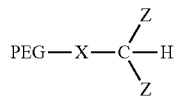

wherein: X is a spacer moiety and each Z is an activated terminal group linked to CH by a chain of atoms of defined length. The chain of atoms linking the Z functional groups to the branching carbon atom serve as a tethering group and may comprise, for example, alkyl chains, ether chains, ester chains, amide chains and combinations thereof. U.S. Pat. No. 6,362,254, discloses various forked PEG structures capable of use in the present invention.

The PEG polymer may comprise a pendant PEG molecule having reactive groups, such as carboxyl, covalently attached along the length of the PEG rather than at the end of the PEG chain. The pendant reactive groups can be attached to the PEG directly or through a spacer moiety, such as an alkylene group.

In addition to the above-described forms of PEG, each water-soluble polymer in the polymeric reagent can also be prepared with one or more weak or degradable linkages in the polymer, including any of the above described polymers. For example, PEG can be prepared with ester linkages in the polymer that are subject to hydrolysis. As shown below, this hydrolysis results in cleavage of the polymer into fragments of lower molecular weight:

-PEG-CO$_2$-PEG-+H$_2$O→-PEG-CO$_2$H+HO-PEG-

Other hydrolytically degradable linkages, useful as a degradable linkage within a polymer backbone, include carbonate linkages; imine linkages resulting, for example, from reaction of an amine and an aldehyde (see, e.g., Ouchi et al. (1997) *Polymer Preprints* 38(1):582-3); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; ortho ester linkages that are, for example, formed by reaction between a formate and an alcohol; amide linkages formed by an amine group, e.g., at an end of a polymer such as PEG, and a carboxyl group of another PEG chain; urethane linkages formed from reaction of, e.g., a PEG with a terminal isocyanate group and a PEG alcohol; peptide linkages formed by an amine group, e.g., at an end of a polymer such as PEG, and a carboxyl group of a peptide; and oligonucleotide linkages formed by, for example, a phosphoramidite group, e.g., at the end of a polymer, and a 5' hydroxyl group of an oligonucleotide.

It is understood by those of ordinary skill in the art that the term poly(ethylene glycol) or PEG represents or includes all the above forms of PEG.

Those of ordinary skill in the art will recognize that the foregoing discussion concerning substantially water-soluble polymers is by no means exhaustive and is merely illustrative, and that all polymeric materials having the qualities described above are contemplated. As used herein, the term "water-soluble polymer" refers both to a molecule as well as the residue of water-soluble polymer that has been attached to another moiety.

Each water-soluble polymer is attached (either directly or through a spacer moiety comprised of one or more atoms) to an aromatic-containing moiety bearing an ionizable hydrogen atom. Thus, the aromatic-containing moiety serves as a point of attachment for one or more water-soluble polymers.

Without wishing to be bound by theory, it is believed to be advantageous to have the aromatic-containing moiety serve as a point of attachment for one or more water-soluble polymers. Specifically, by having each water-soluble polymer attached (either directly or through a spacer moiety) to the aromatic-containing moiety, the often toxic effects associated with aromatic species may be reduced through a steric or blocking effect provided by the water-soluble polymer. This steric or blocking effect can reduce or eliminate potentially damaging metabolic processes that potentially occur when administering some aromatic substances. Thus, the presently described polymeric reagents having two or more water-soluble polymers can provide conjugates that are believed to have reduced toxicity. Such an advantage is believed to differentiate over other polymeric reagents (and corresponding conjugates) wherein, for example, a single branched water-soluble polymer is attached to an aromatic-containing moiety.

Although most any aromatic-containing moiety bearing an ionizable hydrogen atom can be used, the aromatic-containing moiety must provide a site or sites for attachment of various components. In addition, it must be recognized that the aromatic-containing moiety does not itself have to be completely aromatic. The aromatic-containing moiety can, for example, contain one or more separate aromatic moieties optionally linked to each other directly or through a spacer moiety comprising one or more atoms.

In some instances the aromatic-moiety bearing an ionizable hydrogen atom will take the form of one of the following structures:

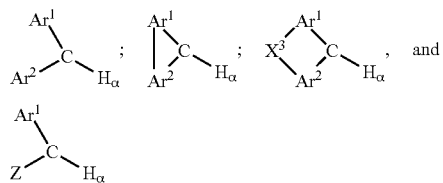

wherein: $Ar^1$ is a first aromatic moiety, $Ar^2$ is a second aromatic moiety, $X^3$ is a spacer moiety, and Z is an electron altering group, relative to H. Such electron altering groups are explained in further detail below. Preferred Z groups include, but are not limited to, —$CF_3$, —$CH_2CF_3$, —$CH_2C_6F_5$, —CN, —$NO_2$, —S(O)R, —S(O)Aryl, —$S(O_2)$R, —$S(O_2)$Aryl, —$S(O_2)$OR, —$S(O_2)$OAryl, —$S(O_2)$NHR, —$S(O_2)$NHAryl, —C(O)R, —C(O)Aryl, —C(O)OR, —C(O)NHR, and the like, wherein R is H or an organic radical.

Exemplary aromatic moieties (which can be further substituted with one or more electron altering groups as will be further explained herein) include the following (where, in each case, the ionizable hydrogen atom of interest is a hydrogen attached to an aliphatic carbon adjacent to one or more of the aromatic rings, i.e. it is benzylic or benzylic like):

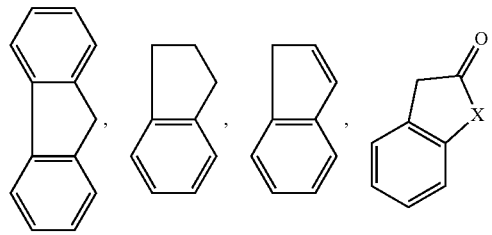

(wherein X is O, SH, NH, NR where R is an organic radical)

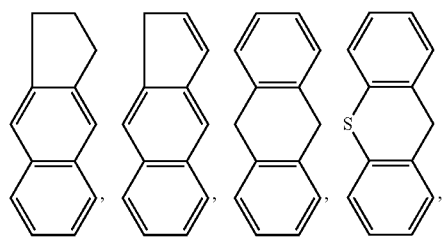

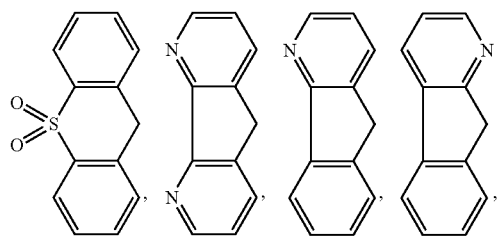

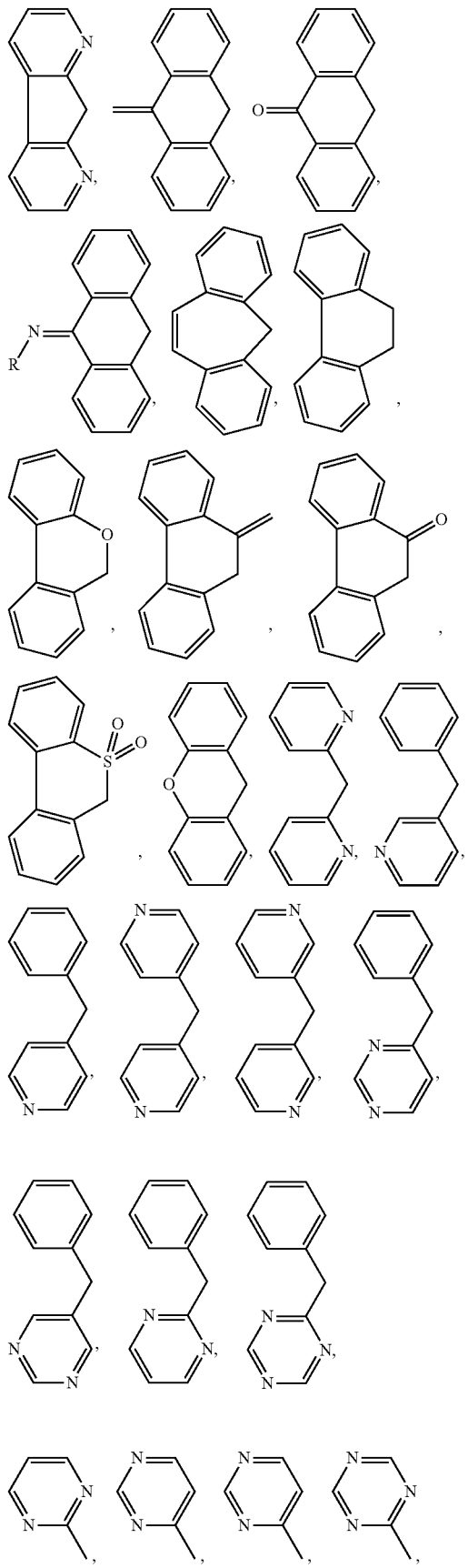

-continued

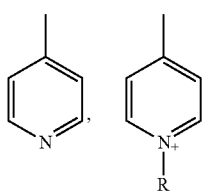

wherein R is an organic radical, preferably alkyl),

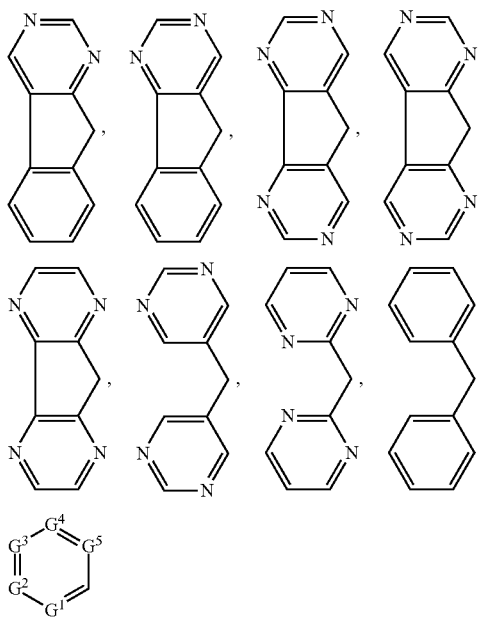

wherein each of $G^1$, $G^2$, $G^3$, $G^4$, and $G^5$ is independently N, C—H or substituted carbon with the proviso that where any of $G^1$, $G^2$, $G^3$, $G^4$, and $G^5$ of G is N, the adjacent atom must be C—H or a substituted carbon. Preferred aromatice moieties include

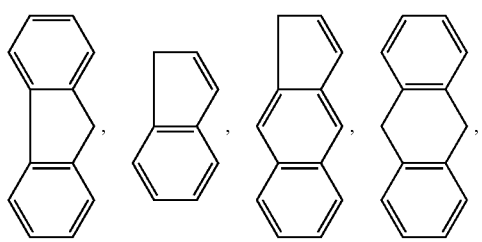

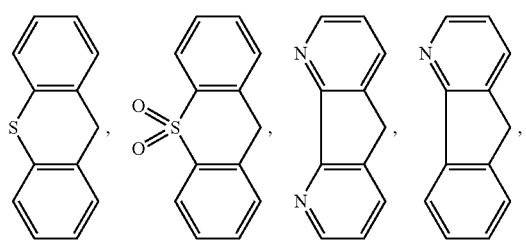

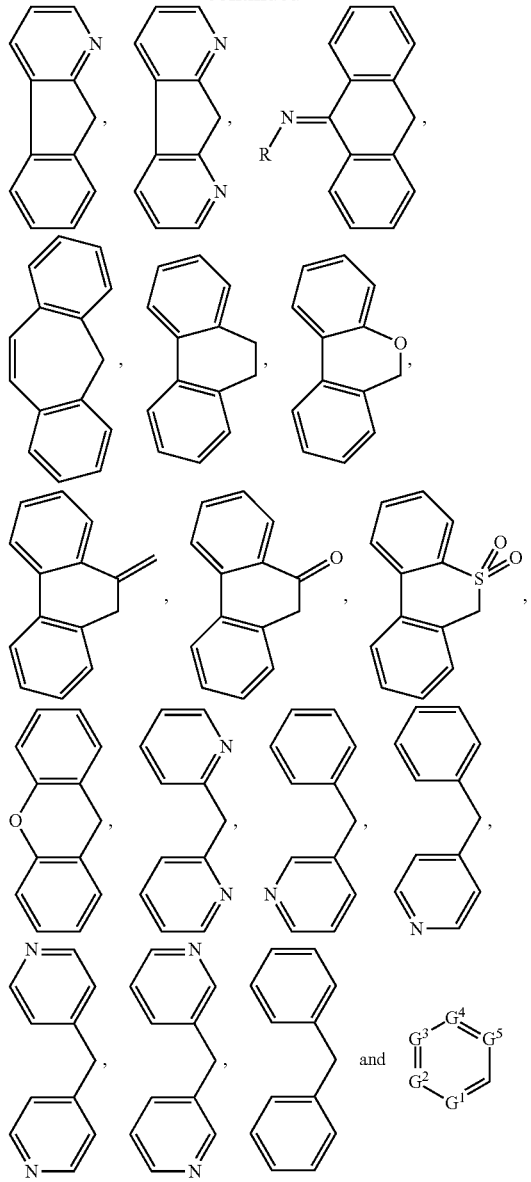

wherein each of $G^1$, $G^2$, $G^3$, $G^4$, and $G^5$ is independently N, C—H or substituted carbon with the proviso that where any of $G^1$, $G^2$, $G^3$, $G^4$, and $G^5$ of G is N, the adjacent atom must be C—H or a substituted carbon.

In one or more embodiments, the aromatic-containing moiety bearing an ionizable hydrogen atom optionally includes one or more electron altering groups ("$R^e$", "$R^{e1}$", "$R^{e2}$", and so forth). An electron altering group is a group that is either electron donating (and therefore referred to as an "electron donating group"), or electron withdrawing (and therefore referred to as an "electron withdrawing group"). When attached to the aromatic-containing moiety bearing an ionizable hydrogen atom, an electron donating group is a group having the ability to position electrons away from itself and closer to or within the aromatic-containing moiety. When attached to the aromatic-containing moiety bearing an ionizable hydrogen atom, an electron withdrawing group is a group having the ability to position electrons toward itself and away from the aromatic-containing moiety. Hydrogen is used as the standard for comparison in the determination of whether a given group positions electrons away or toward itself.

While not wishing to be bound by theory, electron altering groups—by changing the position of electrons (i.e., the "electron density") of the aromatic-containing moiety bearing an ionizable hydrogen atom—influence the ease by which the ionizable hydrogen atom ionizes. Thus, it is believed that electron withdrawing groups increase the acidity of the ionizable hydrogen atom while electron donating groups decrease the acidity of the ionizable hydrogen atom. Electron donating and withdrawing groups affecting the acidity of the ionizable hydrogen atom include groups contained within the spacer moieties (e.g., $X^1$, $X^2$, $X^3$ and so forth) serving to link various constituents of the structures provided herein.

Exemplary electron withdrawing groups include halo (e.g., bromo, fluoro, chloro, and iodo), nitro, carboxy, ester, formyl, keto, azo, amidocarbonyl, amidosulfonyl, carboxamido, sulfonoxy, sulfonamide, ureido, and aryl. Exemplary electron donating groups include hydroxyl, lower alkoxy (e.g., methoxy, ethoxy and the like), lower alkyl (such as methyl, ethyl, and the like), amino, lower alkylamino, di-lower alkylamino, aryloxy (such as phenoxy and the like), arylalkoxy (such as phenoxy and the like), aminoaryls (such as p-dimethylaminophenyl and the like), mercapto, and alkylthio.

In one or more embodiments, the aromatic-containing moiety may include (in addition to one or more water-soluble polymers) one, two three, four, or more electron altering groups. Exemplary instances where the aromatic-containing moiety includes two electron altering groups are shown in the following structures below:

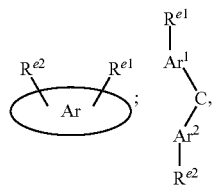

wherein

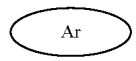

is an aromatic-containing moiety, $Ar^1$ is a first aromatic moiety, $Ar^2$ is a second aromatic moiety, $R^{e1}$ is an electron altering group, and $R^{e2}$ is an electron altering group, while the ionizable hydrogen atom (i.e., $H_\alpha$), the one or more water-soluble polymers, and any other constituents that may be present are not shown. When each of $R^{e1}$ and $R^{e2}$ is different, (a) $R^{e1}$ and $R^{e2}$ can be different electron withdrawing groups, (b) $R^{e1}$ and $R^{e2}$ can be different electron donating groups, (c) or $R^{e1}$ and $R^{e2}$ can be such that one is an electron withdrawing group and the other is an electron donating group. In many circumstances, however, each of $R^{e1}$ and $R^{e2}$ will be the same.

Typically, but not necessarily, placement of an electron altering group on the aromatic-containing moiety bearing an ionizable hydrogen atom is often determined by the preferred entry point of electron altering groups added through aromatic electrophilic or nucleophilic substitution processes. For example, with a fluorene ring, typical positions for addition of electron altering groups by electrophilic aromatic substitution are the "2" and "7" positions. If these positions are occupied by a spacer moiety (which is attached to a water-soluble polymer) other positions on the fluorene ring will be substituted based on factors such as (a) the directing ability of the spacer moiety (e.g., $X^1$ and $X^2$), and (b) steric influences. Often, however, the "4" and "5" positions of a fluorene ring represent the more likely sites for attachment when the "2" and "7" positions are unavailable and especially when the alpha carbon, i.e., the 9-position in fluorene (i.e., the carbon bearing an ionizable hydrogen atom, $H_\alpha$), is substituted. For illustration, the positions in the fluorene ring are identified on the following structure:

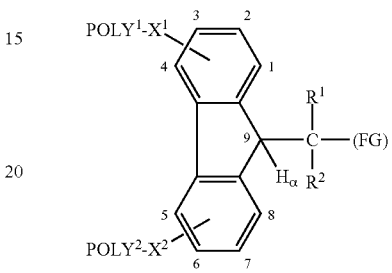

wherein, each of $POLY^1$, $POLY^2$, $X^1$, $X^2$, $R^1$, $R^2$, $H_\alpha$ and (FG) is as defined with respect to Formula I, infra. Although exemplary positions of electron altering groups and other groups have been referred to with respect to a fluorene ring, the present discussion of positional location of electron altering groups is applicable to other aromatic systems as well. One of ordinary skill in the art can determine the positional locations in other ring systems.

As previously indicated, electron altering groups can influence the acidity of the ionizable hydrogen atom of the aromatic-containing moiety in different ways depending on the nature of the particular electron altering group. For example, due to the proximity of electron altering groups at positions "1" and "8" to the ionizable hydrogen atom in the fluoroene ring shown above, electron altering groups at these positions would have the greatest influence through bond (inductive) effects. When the $POLY^1$-$X^1$— and $POLY^2$-$X^2$— are attached at the 2 and 7 positions, however, addition of an electron altering group at the 4 or 5 positions is more likely, for the reasons mentioned above (i.e., directing effects of the spacer moieties and steric effects). Electron altering groups that interact with the ring through resonance effects, such as amido, carboxy, nitro, and alkoxy groups, can provide the resonance effect at a significant distance from the alpha hydrogen. As a consequence, their placement relatively close to the ionizable hydrogen atom may be less important. From another perspective, it may be advantageous to leave relatively close positions (e.g., the "1" and "4" positions) unsubstituted as the ionizable hydrogen atom that will ultimately become removed will likely be retarded by steric effects of electron altering groups at these positions. Again, although exemplary positions of electron altering groups and other groups have been referred to with respect to a fluorene ring, the present discussion of positional location is applicable to other ring systems as well; one of ordinary skill in the art can determine the corresponding positional locations in other ring systems.

To better understand the release reaction of a conjugate formed with a polymeric reagent of the invention (and to also demonstrate effect of electron altering groups on that process) and without any intent of being bound by theory, a proposed mechanism of the release process is provided. A schematic of the proposed mechanism is shown below utilizing a fluorene moiety as the aromatic-containing moiety. In the schematic, an exemplary conjugate of the invention is shown wherein a carbamate linkage connects the residue of the active agent ("Drug") to the rest of the molecule. The variables "POLY$^1$," "POLY$^2$," "X$^1$," "X$^2$," "R$^1$" and "R$^2$" are as previously defined.

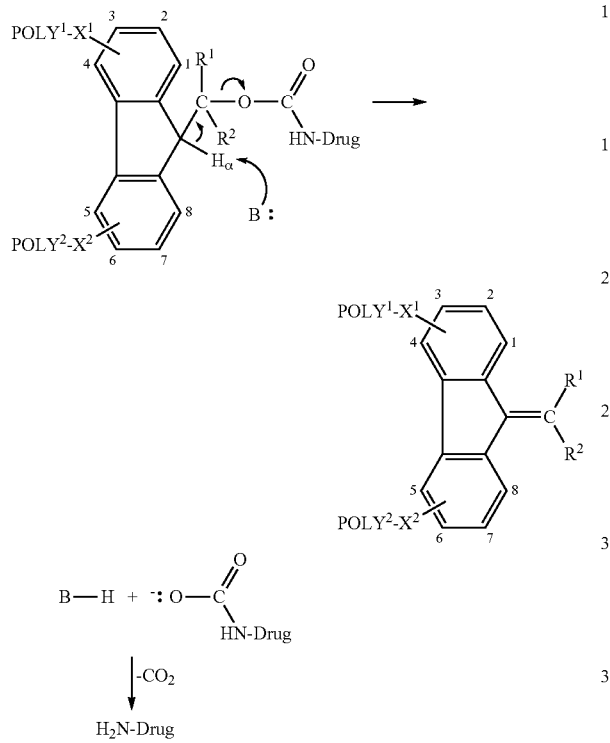

The release process is typically initiated by the attack of a basic molecule, ion, or species that has the capacity to accept a proton in a transfer process ("B:" as shown in the schematic). In vivo, this may be any one of several kinds of ionic species or a protein, which has several basic atoms. Elimination occurs to form a substituted fulvene moiety (or corresponding structure when a non-fluorene structure is employed), thereby releasing the active agent or "drug" species, which may initially be attached to a carboxy group, which is rapidly lost under physiological conditions.

The release process can be concerted or stepwise. Regardless of the exact nature of the proton removal step, either a carbanion is formed as an intermediate or a transition state having carbanionic character is involved. Thus, electron donating groups attached to the aromatic rings, which retard the formation of carbanions, will retard the carbanion-formation process, thereby decreasing the release rate. Conversely, electron withdrawing groups, which facilitate the formation of carbanionic species and stabilize carbanionic transition states, will accelerate the carbanion formation process, thereby increasing the release rate.

Advantageously, by including one or more electron altering groups to the aromatic-containing moiety, it is possible to more closely provide the desired rate of the release of the active agent. By including one or more electron withdrawing groups on the aromatic-containing moiety, release is believed to increase, while the presence of one or more electron donating group is believed to decrease the rate of release. Thus, it is believed that the presence of one or more electron altering groups can provide relative stability or instability of a charged intermediate or transition state that may be involved in the release reaction. Accordingly, by including one or more such electron altering groups on the aromatic-containing moiety, it is possible to better customize a desired rate of release of the original active agent that was conjugated to a polymeric reagent of the invention.

It is possible to determine what effect such an electron altering group will have on the drug release rate of the conjugate by preparing a polymeric reagent having the proposed electron altering group, preparing a conjugate using this polymeric reagent, testing the conjugate for drug release rate over time, and comparing the drug release rate to a conjugate prepared with a control polymeric reagent.

To determine relative release rates of a conjugate in vitro, a conjugate can be prepared and studied. See Example 5, infra. The preparation of a glycine conjugate is illustrated in the scheme below (where m-PEGO and OPEG-m each are defined as —O—CH$_2$CH$_2$—(OCH$_2$CH$_2$)$_n$—OCH$_3$, wherein each n is from 4 to 1500).

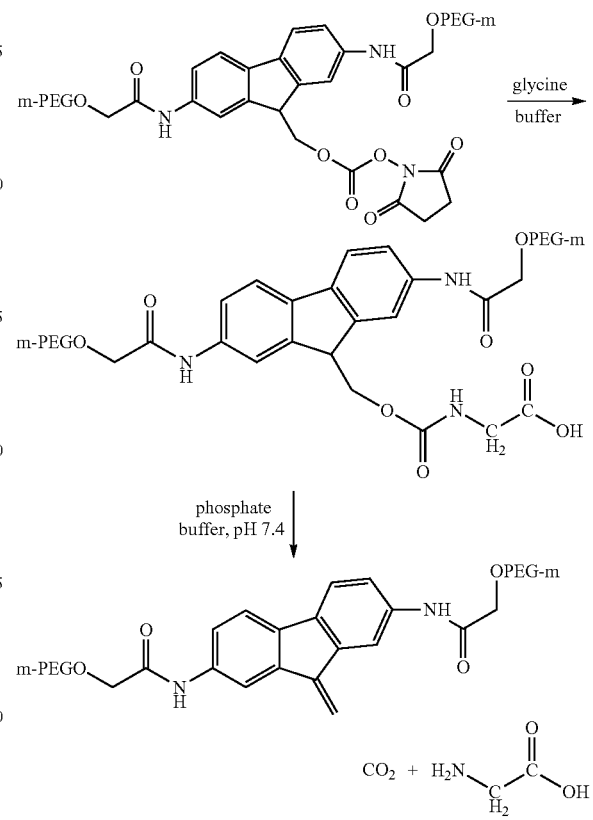

The release rate of this conjugate was studied under simulated in vivo conditions by observing the reaction in a buffered medium at a near-neutral pH. By following the appearance of the fulvene-containing moiety over time, one may calculate a half-life for the reaction resulting in release. This release rate can be qualitatively compared to the release rates of other glycine conjugates that differ by the number and/or type of electron altering groups. In doing so, one can determine the release rate for any given species.

The functional group of the polymeric reagents described herein is a functional group capable of reacting with an amino group of an active agent to form a degradable linkage, such as a carbamate linkage. The invention is not limited with respect to specific functional group so long as the functional group is capable of reacting with an amino group of an active agent to form a degradable linkage, such as a carbamate linkage. Exemplary functional groups capable of reacting with an amino group of an active agent include those functional groups selected from the group consisting of active carbonates such as N-succinimidyl, 1-benzotriazolyl, imidazole, carbonate halides (such as carbonate chloride and carbonate bromide), phenolates (such as p-nitrophenolate) and so forth. Also, as a special case, if the active agent is available with the active amine group converted into an isocyantate or isothiocyanate group, then the functional group of the polymeric reagent can be hydroxyl as the reaction of these components provide a degradable carbamate linkage.

A spacer moiety (e.g., "X", "$X^1$", "$X^2$", "$X^3$", and so forth) is any atom or series of atoms connecting one part of a molecule to another. For purposes of the present disclosure, however, a series of atoms is not a spacer moiety when the series of atoms is immediately adjacent to a polymer and the series of atoms is but another monomer such that the proposed spacer moiety would represent a mere extension of the polymer chain. For example, given the partial structure "POLY-X-," and POLY is defined as "$CH_3O(CH_2CH_2O)_m$—" wherein (m) is 2 to 4000 and X is defined as a spacer moiety, the spacer moiety cannot be defined as "—$CH_2CH_2O$—" since such a definition would merely represent an extension of the polymer. In such a case, however, an acceptable spacer moiety could be defined as "—$CH_2CH_2$—"

Exemplary spacer moieties include, but are not limited to, —C(O)—, —S($O_2$)—, —S(O)—, —NH—S($O_2$)—, —S($O_2$)—NH—, —CH=CH—, —O—CH=CH—, —C(O)—NH—, —NH—C(O)—NH—, —O—C(O)—NH—, —C(S)—, —$CH_2$—, —$CH_2$—$CH_2$—, —$CH_2$—$CH_2$—$CH_2$—, —$CH_2$—$CH_2$—$CH_2$—$CH_2$—, —O—$CH_2$—, —$CH_2$—O—, —O—$CH_2$—$CH_2$—, —$CH_2$—O—$CH_2$—, —$CH_2$—$CH_2$—O—, —O—$CH_2$—$CH_2$—$CH_2$—, —$CH_2$—O—$CH_2$—$CH_2$—, —$CH_2$—$CH_2$—O—$CH_2$—, —$CH_2$—$CH_2$—$CH_2$—O—, —O—$CH_2$—$CH_2$—$CH_2$—$CH_2$—, —$CH_2$—O—$CH_2$—$CH_2$—$CH_2$—, —$CH_2$—$CH_2$—O—$CH_2$—$CH_2$—, —$CH_2$—$CH_2$—$CH_2$—O—$CH_2$—, —$CH_2$—$CH_2$—$CH_2$—$CH_2$—O—, —S—$CH_2$—, —$CH_2$—S—, —S—$CH_2$—$CH_2$—, —$CH_2$—S—$CH_2$—, —$CH_2$—$CH_2$—S—, —S—$CH_2$—$CH_2$—$CH_2$—, —$CH_2$—S—$CH_2$—$CH_2$—, —$CH_2$—$CH_2$—S—$CH_2$—, —$CH_2$—$CH_2$—$CH_2$—S—, —S—$CH_2$—$CH_2$—$CH_2$—$CH_2$—, —$CH_2$—S—$CH_2$—$CH_2$—$CH_2$—, —$CH_2$—$CH_2$—S—$CH_2$—$CH_2$—, —$CH_2$—$CH_2$—$CH_2$—S—$CH_2$—, —$CH_2$—$CH_2$—$CH_2$—$CH_2$—S—, —C(O)—NH—$CH_2$—, —C(O)—NH—$CH_2$—$CH_2$—, —$CH_2$—C(O)—NH—$CH_2$—, —$CH_2$—$CH_2$—C(O)—NH—, —C(O)—NH—$CH_2$—$CH_2$—$CH_2$—, —$CH_2$—C(O)—NH—$CH_2$—$CH_2$—, —$CH_2$—$CH_2$—C(O)—NH—$CH_2$—, —$CH_2$—$CH_2$—$CH_2$—C(O)—NH—, —C(O)—NH—$CH_2$—$CH_2$—$CH_2$—$CH_2$—, —$CH_2$—C(O)—NH—$CH_2$—$CH_2$—$CH_2$—, —$CH_2$—$CH_2$—C(O)—NH—$CH_2$—$CH_2$—, —$CH_2$—$CH_2$—$CH_2$—C(O)—NH—$CH_2$—, —$CH_2$—$CH_2$—$CH_2$—$CH_2$—C(O)—NH—, —$CH_2$—$CH_2$—$CH_2$—$CH_2$—C(O)—NH—, —$CH_2$—$CH_2$—$CH_2$—$CH_2$—C(O)—NH—, —NH—C(O)—$CH_2$—C(O)—NH—, —NH—C(O)—$CH_2$—$CH_2$—C(O)—NH—, —NH—C(O)—$CH_2$—$CH_2$—$CH_2$—C(O)—NH—, —NH—C(O)—$CH_2$—$CH_2$—$CH_2$—$CH_2$—C(O)—NH—, —NH—C(O)—CH=CH—C(O)—NH—, —C(O)—O—$CH_2$—, —$CH_2$—C(O)—O—$CH_2$—, —C(O)—O—$CH_2$—, —$CH_2$—$CH_2$—C(O)—O—$CH_2$—, —C(O)—O—$CH_2$—$CH_2$—, —NH—C(O)—$CH_2$—, —$CH_2$—NH—C(O)—$CH_2$—, —$CH_2$—$CH_2$—NH—C(O)—$CH_2$—, —NH—C(O)—$CH_2$—$CH_2$—, —$CH_2$—NH—C(O)—$CH_2$—$CH_2$—, —$CH_2$—$CH_2$—NH—C(O)—$CH_2$—$CH_2$—, —NH—C(O)—$CH_2$—$CH_2$—$CH_2$—, —$CH_2$—$CH_2$—NH—C(O)—$CH_2$—$CH_2$—, —C(O)—NH—$CH_2$—, —C(O)—NH—$CH_2$—$CH_2$—, —O—C(O)—NH—$CH_2$—, —O—C(O)—NH—$CH_2$—$CH_2$—, —NH—$CH_2$—$CH_2$—, —NH—$CH_2$—, —NH—$CH_2$—$CH_2$—, —$CH_2$—NH—$CH_2$—, —$CH_2$—$CH_2$—NH—$CH_2$—, —C(O)—$CH_2$—, —C(O)—$CH_2$—$CH_2$—, —$CH_2$—C(O)—$CH_2$—, —$CH_2$—$CH_2$—C(O)—$CH_2$—, —$CH_2$—$CH_2$—C(O)—$CH_2$—$CH_2$—, —$CH_2$—$CH_2$—C(O)—$CH_2$—$CH_2$—, —$CH_2$—$CH_2$—C(O)—NH—$CH_2$—$CH_2$—NH—, —$CH_2$—$CH_2$—$CH_2$—C(O)—NH—$CH_2$—$CH_2$—NH—C(O)—, —$CH_2$—$CH_2$—$CH_2$—C(O)—NH—$CH_2$—$CH_2$—NH—C(O)—, —$CH_2$—$CH_2$—$CH_2$—C(O)—NH—$CH_2$—$CH_2$—C(O)—, —$CH_2$—$CH_2$—$CH_2$—C(O)—, —O—$CH_2$—, —O—C(O)—NH—$CH_2$—$CH_2$—, —O—C(O)—NH—$CH_2$—$CH_2$—, —NH—$CH_2$—$CH_2$—, —NH—$CH_2$—, —NH—$CH_2$—$CH_2$—NH—, —$CH_2$—$CH_2$—NH—$CH_2$—, —$CH_2$—$CH_2$—NH—, —$CH_2$—$CH_2$—NH—$CH_2$—, —$CH_2$—$CH_2$—$CH_2$—C(O)—$CH_2$—$CH_2$—, —$CH_2$—$CH_2$—$CH_2$—C(O)—$CH_2$—$CH_2$—, —$CH_2$—$CH_2$—C(O)—$CH_2$—$CH_2$—, —$CH_2$—$CH_2$—C(O)—$CH_2$—$CH_2$—, —$CH_2$—$CH_2$—C(O)—, —O—C(O)—NH—[$CH_2$]$_h$—(OCH2CH2)$_j$—, —NH—C(O)—O—[$CH_2$]$_h$—(O$CH_2CH_2$)$_j$—, bivalent cycloalkyl group, —O—, —S—, an amino acid, —N($R^6$)—, and combinations of two or more of any of the foregoing, wherein $R^6$ is H or an organic radical selected from the group consisting of alkyl, substituted alkyl, alkenyl, substituted alkenyl, alkynyl, substituted alkynyl, aryl and substituted aryl, (h) is zero to six, and (j) is zero to 20. Other specific spacer moieties have the following structures: —C(O)—NH—($CH_2$)$_{1-6}$—NH—C(O)—, —NH—C(O)—NH—($CH_2$)$_{1-6}$—NH—C(O)—, and —O—C(O)—NH—($CH_2$)$_{1-6}$—NH—C(O)—, wherein the subscript values following each methylene indicate the number of methylenes contained in the structure, e.g., ($CH_2$)$_{1-6}$ means that the structure can contain 1, 2, 3, 4, 5 or 6 methylenes. Additionally, any of the above spacer moieties may further include an ethylene oxide oligomer chain comprising 1 to 20 ethylene oxide monomer units [i.e., —($CH_2CH_2O$)$_{1-20}$]. That is, the ethylene oxide oligomer chain can occur before or after the spacer moiety, and optionally in between any two atoms of a spacer moiety comprised of two or more atoms. Also, the oligomer chain would not be considered part of the spacer moiety if the oligomer is adjacent to a polymer segment and merely represent an extension of the polymer segment. Finally, it is noted that some spacer moieties include an atom or group of atoms that also function as an electron altering group; in such a cases, the inclusion of one or more additional "discrete" (i.e., not a part of a spacer moiety) electron altering groups may not be desired or necessary.

Preferred spacer moieties for X and $X^1$ include those selected from the group consisting of —C(O)—NH—$CH_2$—$CH_2$—, —$CH_2$—$CH_2$—NH—C(O)—, —C(O)—NH—$CH_2$—$CH_2$—$CH_2$—, —$CH_2$—$CH_2$—$CH_2$—NH—C(O)—, —C(O)—NH—$CH_2$—$CH_2$—$CH_2$—$CH_2$—, —$CH_2$—$CH_2$—$CH_2$—$CH_2$—NH—C(O)—, —$CH_2$—$CH_2$—$CH_2$—NH—C(O)—, —C(O)—NH—, —NH—C(O)—, —C(O)—NH—$CH_2$—$CH_2$—$CH_2$—$CH_2$—$CH_2$—$CH_2$—NH—C(O)—, —NH—C(O)—$CH_2$—$CH_2$—, —$CH_2$—$CH_2$—C(O)—NH—, —NH—C(O)—$CH_2$—$CH_2$—$CH_2$—, —$CH_2$—$CH_2$—$CH_2$—C(O)—NH—, —NH—C(O)—$CH_2$—$CH_2$—$CH_2$—$CH_2$—, —$CH_2$—$CH_2$—$CH_2$—$CH_2$—C(O)—NH—, —NH—C(O)—$CH_2$—$CH_2$—$CH_2$—$CH_2$—$CH_2$—, —$CH_2$—$CH_2$—$CH_2$—$CH_2$—$CH_2$—C(O)—NH—, —NH—C(O)—$CH_2$—$CH_2$—C(O)—, —C(O)—$CH_2$—$CH_2$—C(O)—NH—, —NH—C(O)—$CH_2$—$CH_2$—$CH_2$—C(O)—, —C(O)—$CH_2$—$CH_2$—$CH_2$—C(O)—NH—, —NH—C(O)—$CH_2$—$CH_2$—$CH_2$—$CH_2$—C(O)—, —C(O)—$CH_2$—$CH_2$—$CH_2$—$CH_2$—C(O)—NH—, —NH—C(O)—$CH_2$—$CH_2$—$CH_2$—$CH_2$—$CH_2$—C(O)—, —C(O)—$CH_2$—$CH_2$—$CH_2$—$CH_2$—$CH_2$—C(O)—NH—, —C(O)—$CH_2$—$CH_2$—, —$CH_2$—$CH_2$—C(O)—, —C(O)—$CH_2$—$CH_2$—$CH_2$—, —$CH_2$—$CH_2$—$CH_2$—C(O)—, —C(O)—$CH_2$—$CH_2$—$CH_2$—$CH_2$—, —$CH_2$—$CH_2$—$CH_2$—$CH_2$—C(O)—, —$CH_2$—$CH_2$—$CH_2$—, —$CH_2$—$CH_2$—$CH_2$—$CH_2$—$CH_2$—

C(O)—, —NH—CH$_2$—CH$_2$—(OCH$_2$CH$_2$)$_{1-3}$—NH—C(O)—, —C(O)—NH—(CH$_2$CH$_2$O)$_{1-3}$—CH$_2$—CH$_2$—NH—, —C(O)—NH—CH$_2$—CH$_2$—(OCH$_2$CH$_2$)$_{1-3}$—NH—C(O)—, —C(O)—NH—(CH$_2$CH$_2$O)$_{1-3}$—CH$_2$—CH$_2$—NH—C(O)—, —NH—C(O)—CH$_2$—, —CH$_2$—C(O)—NH—, —NH—C(O)—CH$_2$—O—, —O—CH$_2$—C(O)—NH—, —CH$_2$—CH$_2$—NH—C(O)—CH$_2$—CH$_2$—, —NH—C(O)—CH$_2$—CH$_2$—CH$_2$—C(O)—NH—CH$_2$—CH$_2$—, —O—CH$_2$—CH$_2$—NH—C(O)—CH$_2$—CH$_2$—CH$_2$—C(O)—NH—, —NH—C(O)—CH$_2$—CH$_2$—CH$_2$—C(O)—NH—CH$_2$—CH$_2$—O—, —C(O)—NH—CH$_2$—CH$_2$—, —CH$_2$—CH$_2$—NH—C(O)—, —C(O)—NH—CH$_2$—CH$_2$—O—, and —O—CH$_2$—CH$_2$—NH—C(O)—. Preferred spacer moieties for X$^2$ include those selected from the group consisting of —C(O)—NH—CH$_2$—CH$_2$—, —CH$_2$—CH$_2$—NH—C(O)—, —C(O)—NH—CH$_2$—CH$_2$—CH$_2$—, —CH$_2$—CH$_2$—CH$_2$—NH—C(O)—, —C(O)—NH—CH$_2$—CH$_2$—CH$_2$—CH$_2$—, —CH$_2$—CH$_2$—CH$_2$—CH$_2$—NH—C(O)—, —C(O)—NH—, —NH—C(O)—, —C(O)—NH—CH$_2$—CH$_2$—CH$_2$—CH$_2$—, —CH$_2$—CH$_2$—CH$_2$—CH$_2$—NH—C(O)—, —NH—C(O)—CH$_2$—CH$_2$—, —NH—C(O)—CH$_2$—CH$_2$—CH$_2$—, —CH$_2$—CH$_2$—C(O)—NH—, —NH—C(O)—CH$_2$—CH$_2$—, —CH$_2$—CH$_2$—CH$_2$—C(O)—NH—, —NH—C(O)—CH$_2$—CH$_2$—CH$_2$—CH$_2$—, —CH$_2$—CH$_2$—CH$_2$—C(O)—NH—, —NH—C(O)—CH$_2$—CH$_2$—CH$_2$—CH$_2$—, —CH$_2$—C(O)—NH—, —NH—C(O)—CH$_2$—CH$_2$—C(O)—, —C(O)—CH$_2$—CH$_2$—C(O)—NH—, —NH—C(O)—CH$_2$—CH$_2$—CH$_2$—C(O)—, —C(O)—CH$_2$—CH$_2$—CH$_2$—CH$_2$—C(O)—NH—, —NH—C(O)—CH$_2$—CH$_2$—CH$_2$—CH$_2$—C(O)—, —C(O)—CH$_2$—CH$_2$—CH$_2$—CH$_2$—C(O)—NH—, —NH—C(O)—CH$_2$—CH$_2$—, —C(O)—CH$_2$—CH$_2$—CH$_2$—CH$_2$—C(O)—, —CH$_2$—CH$_2$—C(O)—, —C(O)—CH$_2$—CH$_2$—CH$_2$—CH$_2$—, —CH$_2$—CH$_2$—CH$_2$—CH$_2$—C(O)—, —C(O)—CH$_2$—CH$_2$—CH$_2$—CH$_2$—CH$_2$—, —CH$_2$—CH$_2$—CH$_2$—CH$_2$—C(O)—, —NH—CH$_2$—CH$_2$—(OCH$_2$CH$_2$)$_{1-3}$—NH—C(O)—, —C(O)—NH—(CH$_2$CH$_2$O)$_{1-3}$—CH$_2$—CH$_2$—NH—, —C(O)—NH—CH$_2$—CH$_2$—(OCH$_2$CH$_2$)$_{1-3}$—NH—C(O)—, —C(O)—NH—(CH$_2$CH$_2$O)$_{1-3}$—CH$_2$—CH$_2$—NH—C(O)—, —NH—C(O)—CH$_2$—, —CH$_2$—C(O)—NH—, —NH—C(O)—CH$_2$—O—, —O—CH$_2$—C(O)—NH—, —CH$_2$—CH$_2$—NH—C(O)—CH$_2$—CH$_2$—CH$_2$—C(O)—NH—, —NH—C(O)—CH$_2$—CH$_2$—CH$_2$—C(O)—NH—CH$_2$—CH$_2$—, —O—CH$_2$—CH$_2$—NH—C(O)—CH$_2$—CH$_2$—C(O)—NH—CH$_2$—CH$_2$—O—, —C(O)—NH—CH$_2$—CH$_2$—, —CH$_2$—CH$_2$—NH—C(O)—, —C(O)—NH—CH$_2$—CH$_2$—O—, and —O—CH$_2$—CH$_2$—NH—C(O)—.

Each spacer moiety, when present, in the overall structure can be the same or different than any other spacer moiety in the overall structure. With respect to X$^1$ and X$^2$, it is sometimes preferred that X$^1$ and X$^2$ are the same.

Preferred spacer moieties corresponding to X, X$^1$ and/or X$^2$ include amidocarboxy, carboxyamido, sulfonamide, ester and ureido.

In some embodiments, it is preferred that the spacer moiety (particularly X of Formulae VI and VI-C) satisfies one or more of the following: lacks sulfur atoms (e.g., lacks "—S—"); lacks phosphorous atoms; is a chain of greater than four atoms; and does not include —CO—CH$_2$—NH—CO—, —CO—CH(CH$_3$)—NH—CO— and —CO—CH$_2$—NH—CO—NH. In some embodiments, it is preferred that the spacer moiety (particularly X of Formulae VI and VI-C) is an atom or groups of atoms with the proviso that the atom or group of atoms is lacks sulfur and phosphorous atoms and is not —NH—CO—O—, —NH—CO—CH$_2$—NH$_2$—CO—NH—, —NH—CO—, —NH—CH$_2$—, —NH—CO—NH—, —NH—CS—NH—, —CO—O—, —CO—NH—, and —CH$_2$—NH—. In some embodiment the spacer moiety (particularly X of Formulae VI and VI-C) is not —R$^5$-R$^6$, wherein R$^5$ is selected from the group consisting of —NH—, —S—, —CO—, —COO—, —CH$_2$—, —SO$_2$—, —SO$_3$—, —PO$_2$— and —PO$_3$—, and R$^6$ is a bond or a radical selected from the group consisting of —CO—, —COO—, —CH$_2$—, —CH(CH$_3$)—, —CO—NH—, —CS—NH, —CO—CH$_2$—NH—CO—, —CO—CH(CH$_3$)—NH—CO—, —CO—CH$_2$—NH—CO—NH—, —CO—R$^8$— (wherein R$^8$ is a straight or branched alkylene), a maleimido-containing radical, and triazinyl-containing radical.

In some instances, a spacer moiety and/or any electron altering group may include an amide functionality bonded directly to the aromatic-containing moiety (i.e., wherein the nitrogen of the amide is covalently bonded directed to the aromatic-containing moiety). In some embodiments however, it is preferred that both the spacer moiety and/or any electron altering group does not include an amide functionality (i.e., —NH—C(O)— or —C(O)—NH—) bonded directly to the aromatic-containing moiety.

Exemplary polymeric reagents of the invention will now be discussed in further detail. It must be remembered that while stereochemistry is not specifically shown in any formulae or structures (whether for a polymeric reagent, conjugate, or any other formula or structure), the provided formulae and structures contemplate both enantiomers, as well as compositions comprising mixtures of each enantiomer in equal amounts (i.e., a racemic mixture) and unequal amounts. Thus, for example, a polymeric reagent of Formula IIc in which a single electron altering group (R$^{e1}$) is present includes both enantiomers and mixtures thereof.

An exemplary polymeric reagent of the invention has the following structure:

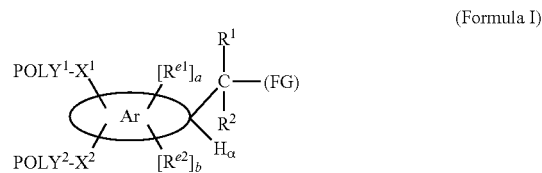

(Formula I)

wherein:
POLY$^1$ is a first water-soluble polymer;
POLY$^2$ is a second water-soluble polymer;
X$^1$ is a first spacer moiety;
X$^2$ is a second spacer moiety;

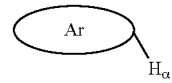

is an aromatic-containing moiety bearing an ionizable hydrogen atom, H$_\alpha$;
R$^1$ is H or an organic radical;
R$^2$ is H or an organic radical;
(a) is either zero or one;
(b) is either zero or one;
R$^{e1}$, when present, is a first electron altering group;
R$^{e2}$, when present, is a second electron altering group; and
(FG) is a functional group capable of reacting with an amino group of an active agent to form a degradable linkage.

When the polymeric reagent corresponding to Formula I has no discrete electron altering groups [i.e., when (a) and (b) are both zero with regard to Formula I], a polymeric reagent of the following formula results:

(Formula Ia)

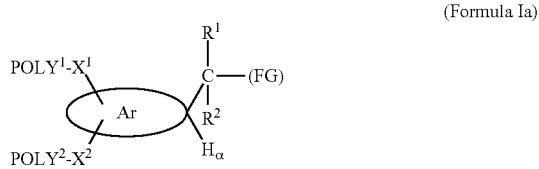

wherein each of POLY$^1$, POLY$^2$, X$^1$, X$^2$, R$^1$, R$^2$,

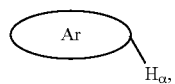

and (FG) is as previously defined with respect to Formula I.

When the polymeric reagent corresponding to Formula I has a single discrete electron altering group [e.g., when (a) is one and (b) is zero with regard to Formula I], a polymeric reagent of the following formula results:

(Formula Ic)

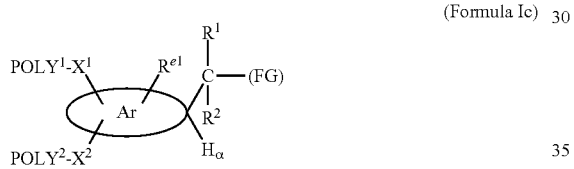

wherein each of POLY$^1$, POLY$^2$, X$^1$, X$^2$, R$^1$, R$^2$,

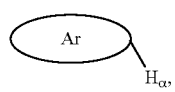

(FG), and R$^{e1}$ is as previously defined with respect to Formula I.

When the polymeric reagent corresponding to Formula I has two discrete electron altering groups [i.e., when (a) and (b) are both one with regard to Formula I], a polymeric reagent of the following formula results:

(Formula Ib)

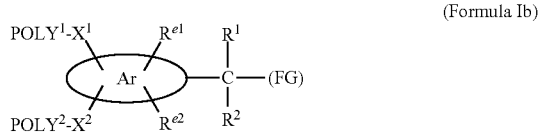

wherein each of POLY$^1$, POLY$^2$, X$^1$, X$^2$, R$^1$, R$^2$,

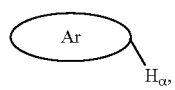

(FG), R$^{e1}$ and R$^{e2}$ is as previously defined with respect to Formula I.

In some cases, the polymeric reagent can include individual aromatic moieties that are only linked to each other through a carbon atom bearing an ionizable hydrogen atom. Such a polymeric reagent has the following formula:

(Formula II)

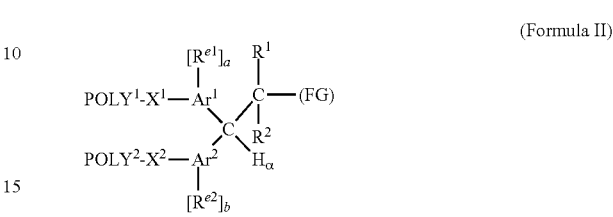

wherein:
POLY$^1$ is a first water-soluble polymer;
POLY$^2$ is a second water-soluble polymer;
X$^1$ is a first spacer moiety;
X$^2$ is a second spacer moiety;
Ar$^1$ is a first aromatic moiety;
Ar$^2$ is a second aromatic moiety;
H$_\alpha$ is an ionizable hydrogen atom;
R$^1$ is H or an organic radical;
R$^2$ is H or an organic radical;
(a) is either zero or one;
(b) is either zero or one;
R$^{e1}$, when present, is a first electron altering group;
R$^{e2}$, when present, is a second electron altering group; and
(FG) is a functional group capable of reacting with an amino group of an active agent to form a degradable linkage, such as a carbamate linkage.

When the polymeric reagent corresponding to Formula II has no discrete electron altering groups [i.e., when (a) and (b) are both zero with regard to Formula II], a polymeric reagent of the following formula results:

(Formula IIa)

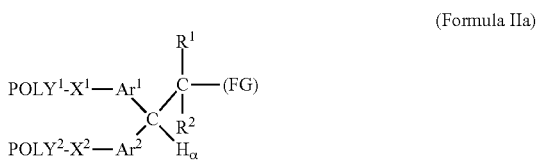

wherein each of POLY$^1$, POLY$^2$, X$^1$, X$^2$, R$^1$, R$^2$, Ar$^1$, Ar$^2$, and (FG) is as previously defined with respect to Formula II.

When the polymeric reagent corresponding to Formula II has a single discrete electron altering group [e.g., when (a) is one and (b) is zero with regard to Formula II], a polymeric reagent of the following formula results:

(Formula IIc)

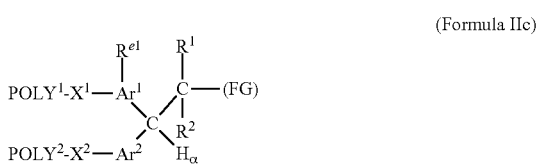

wherein each of POLY$^1$, POLY$^2$, X$^1$, X$^2$, Ar$^1$, Ar$^2$, H$_\alpha$, R$^1$, R$^2$, R$^{e1}$, and (FG) is as previously defined with respect to Formula II.

When the polymeric reagent corresponding to Formula II has two discrete electron altering groups [i.e., when (a) and (b) are both one with regard to Formula II], a polymeric reagent of the following formula results:

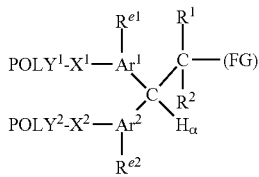
(Formula IIb)

wherein each of POLY$^1$, POLY$^2$, X$^1$, X$^2$, Ar$^1$, Ar$^2$, H$_\alpha$, R$^1$, R$^2$, R$^{e1}$, and R$^{e2}$ is as previously defined with respect to Formula II.

In still other cases, the polymeric reagent can include individual aromatic moieties that are linked to each other both through a carbon atom bearing an ionizable hydrogen atom as well as another direct bond. Such a polymeric reagent has the following formula:

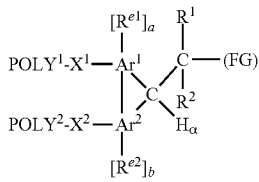
(Formula III)

wherein:
POLY$^1$ is a first water-soluble polymer;
POLY$^2$ is a second water-soluble polymer;
X$^1$ is a first spacer moiety;
X$^2$ is a second spacer moiety;
Ar$^1$ is a first aromatic moiety;
Ar$^2$ is a second aromatic moiety;
H$_\alpha$ is an ionizable hydrogen atom;
R$^1$ is H or an organic radical;
R$^2$ is H or an organic radical;
(a) is either zero or one;
(b) is either zero or one;
R$^{e1}$, when present, is a first electron altering group;
R$^{e2}$, when present, is a second electron altering group; and
(FG) is a functional group capable of reacting with an amino group of an active agent to form a degradable linkage, such as a carbamate linkage.

When the polymeric reagent corresponding to Formula III has no discrete electron altering groups [i.e., when (a) and (b) are both zero with regard to Formula III], a polymeric reagent of the following formula results:

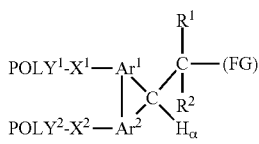
(Formula IIIa)

wherein each of POLY$^1$, POLY$^2$, X$^1$, X$^2$, R$^1$, R$^2$, Ar$^1$, Ar$^2$, and (FG) is as previously defined with respect to Formula III.

When the polymeric reagent corresponding to Formula III has a single discrete electron altering group [e.g., when (a) is one and (b) is zero with regard to Formula III], a polymeric reagent of the following formula results:

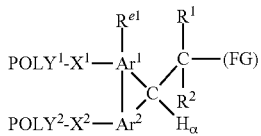
(Formula IIIc)

wherein each of POLY$^1$, POLY$^2$, X$^1$, X$^2$, R$^1$, R$^2$, Ar$^1$, Ar$^2$, R$^{e1}$, and (FG) is as previously defined with respect to Formula III.

When the polymeric reagent corresponding to Formula III has two discrete electron altering groups [i.e., when (a) and (b) are both one with regard to Formula III], a polymeric reagent of the following formula results:

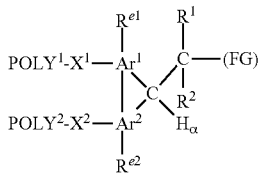
(Formula IIIb)

wherein each of POLY$^1$, POLY$^2$, X$^1$, X$^2$, R$^1$, R$^2$, Ar$^1$, Ar$^2$, R$^{e1}$, R$^{e2}$, and (FG) is as previously defined with respect to Formula III.

In still other cases, the polymeric reagent can include individual aromatic moieties that are linked to each other both through a carbon atom bearing an ionizable hydrogen atom as well as a spacer moiety of one or more atoms. Such a polymeric reagent has the following formula:

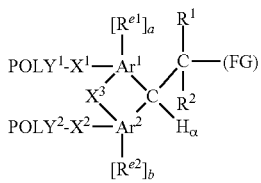
(Formula IV)

wherein:
POLY$^1$ is a first water-soluble polymer;
POLY$^2$ is a second water-soluble polymer;
X$^1$ is a first spacer moiety;
X$^2$ is a second spacer moiety;
X$^3$ is a third spacer moiety;
Ar$^1$ is a first aromatic moiety;
Ar$^2$ is a second aromatic moiety;
H$_\alpha$ is an ionizable hydrogen atom;
R$^1$ is H or an organic radical;
R$^2$ is H or an organic radical;
(a) is either zero or one;
(b) is either zero or one;
R$^{e1}$, when present, is a first electron altering group;
R$^{e2}$, when present, is a second electron altering group; and
(FG) is a functional group capable of reacting with an amino group of an active agent to form a degradable linkage, such as a carbamate linkage.

When the polymeric reagent corresponding to Formula IV has no discrete electron altering groups [i.e., when (a) and (b) are both zero with regard to Formula IV], a polymeric reagent of the following formula results:

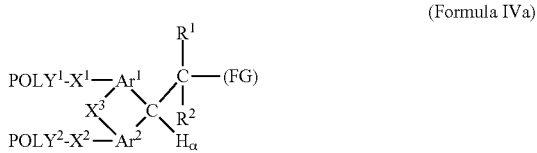

(Formula IVa)

wherein each of POLY$^1$, POLY$^2$, X$^1$, X$^2$, X$^3$, R$^1$, R$^2$, Ar$^1$, Ar$^2$, and (FG) is as previously defined with respect to Formula IV.

When the polymeric reagent corresponding to Formula IV has a single discrete electron altering group [e.g., when (a) is one and (b) is zero with regard to Formula IV], a polymeric reagent of the following formula results:

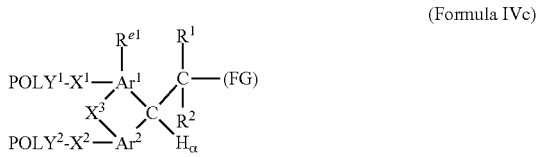

(Formula IVc)

wherein each of POLY$^1$, POLY$^2$, X$^1$, X$^2$, X$^3$, R$^1$, R$^2$, Ar$^1$, Ar$^2$, R$^{e1}$ and (FG) is as previously defined with respect to Formula IV.

When the polymeric reagent corresponding to Formula IV has two discrete electron altering groups [i.e., when (a) and (b) are both one with regard to Formula IV], a polymeric reagent of the following formula results:

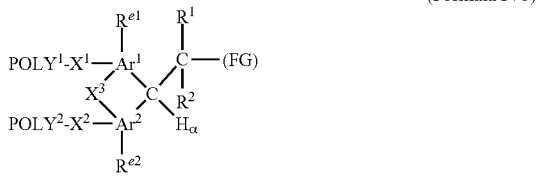

(Formula IVb)

wherein each of POLY$^1$, POLY$^2$, X$^1$, X$^2$, X$^3$, Ar$^1$, Ar$^2$, H$_\alpha$, R$^1$, R$^2$, R$^{e1}$, R$^{e2}$ and (FG) is as previously defined with respect to Formula IV.

A preferred polymeric reagent comprises the following structure:

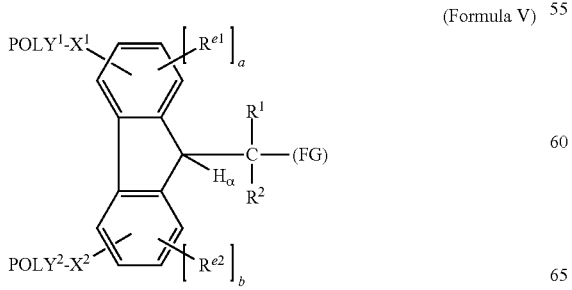

(Formula V)

wherein:

POLY$^1$ is a first water-soluble polymer;
POLY$^2$ is a second water-soluble polymer;
X$^1$ is a first spacer moiety;
X$^2$ is a second spacer moiety;
H$_\alpha$ is an ionizable hydrogen atom;
R$^1$ is H or an organic radical;
R$^2$ is H or an organic radical;
(a) is either zero or one;
(b) is either zero or one;
R$^{e1}$, when present, is a first electron altering group;
R$^{e2}$, when present, is a second electron altering group; and
(FG) is a functional group capable of reacting with an amino group of an active agent to form a degradable linkage.

When the polymeric reagent corresponding to Formula V has no discrete electron altering groups [i.e., when (a) and (b) are both zero with regard to Formula V], a polymeric reagent of the following formula results:

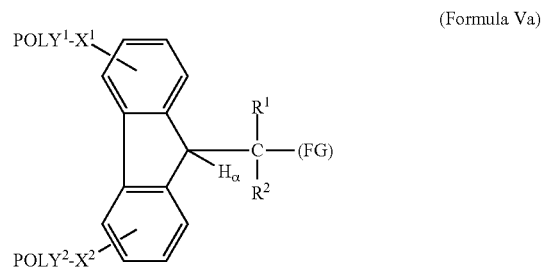

(Formula Va)

wherein each of POLY$^1$, POLY$^2$, X$^1$, X$^2$, H$_\alpha$, R$^1$, R$^2$ and (FG) is as previously defined with respect to Formula V.

When the polymeric reagent corresponding to Formula V has a single discrete electron altering group [e.g., when (a) is one and (b) is zero with regard to Formula V], a polymeric reagent of the following formula results:

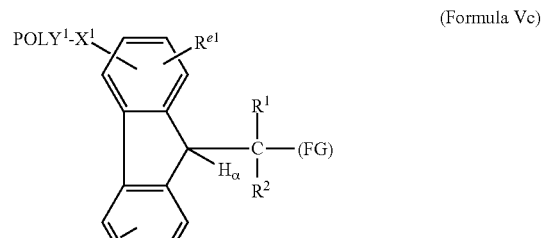

(Formula Vc)

wherein each of POLY$^1$, POLY$^2$, X$^1$, X$^2$, H$_\alpha$, R$^1$, R$^2$, R$^{e1}$ and (FG) is as previously defined with respect to Formula V.

When the polymeric reagent corresponding to Formula V has two discrete electron altering groups [i.e., when (a) and (b) are both one with regard to Formula V], a polymeric reagent of the following formula results:

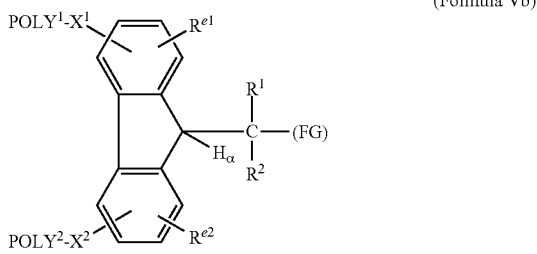
(Formula Vb)

wherein each of $POLY^1$, $POLY^2$, $X^1$, $X^2$, $R^1$, $R^2$, $H_\alpha$, $R^{e1}$, $R^{e2}$, and (FG) is as previously defined with respect to Formula V Still another preferred polymeric reagent is of the following structure:

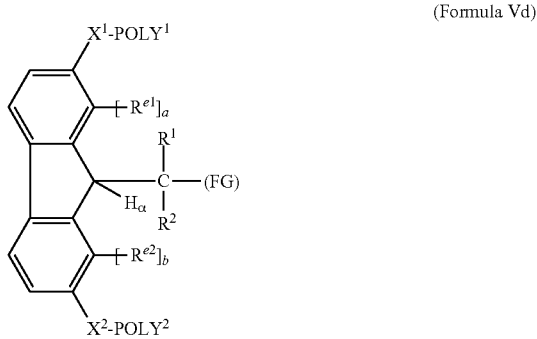
(Formula Vd)

wherein each of $POLY^1$, $POLY^2$, $X^1$, $X^2$, $R^1$, $R^2$, $H_\alpha$, $R^{e1}$, $R^{e2}$, (a), (b) and (FG) is as previously defined with respect to Formula V, with the proviso that $R^{e1}$ is H when (a) is zero and $R^{e2}$ is H when (b) is zero.

Still another preferred polymeric reagent is of the following structure:

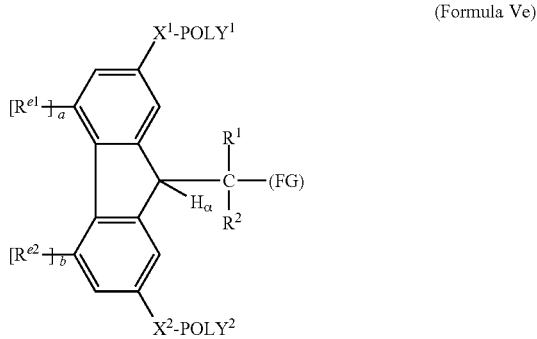
(Formula Ve)

wherein each of $POLY^1$, $POLY^2$, $X^1$, $X^2$, $R^1$, $R^2$, $H_\alpha$, $R^{e1}$, $R^{e2}$ and (FG) is as previously defined with respect to Formula V, with the proviso that $R^{e1}$ is H when (a) is zero and $R^{e2}$ is H when (b) is zero.

Still another preferred polymeric reagent is of the following structure:

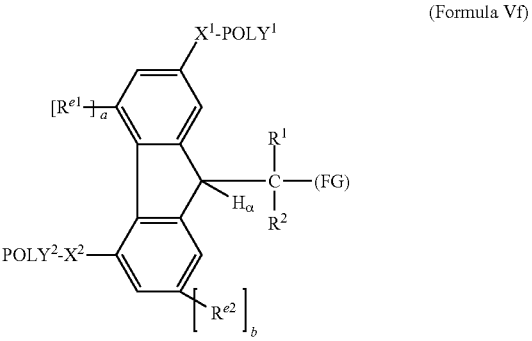
(Formula Vf)

wherein each of $POLY^1$, $POLY^2$, $X^1$, $X^2$, $R^1$, $R^2$, $H_\alpha$, $R^{e1}$, $R^{e2}$ and (FG) is as previously defined with respect to Formula V, with the proviso that $R^{e1}$ is H when (a) is zero and $R^{e2}$ is H when (b) is zero.

Still another preferred polymeric reagent is of the following structure:

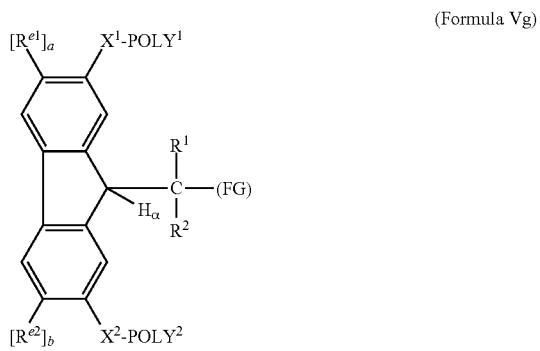
(Formula Vg)

wherein each of $POLY^1$, $POLY^2$, $X^1$, $X^2$, $R^1$, $R^2$, $H_\alpha$, $R^{e1}$, $R^{e2}$, (a), (b) and (FG) is as previously defined with respect to Formula V, with the proviso that $R^{e1}$ is H when (a) is zero and $R^{e2}$ is H when (b) is zero.

Typically, each of $POLY^1$ and $POLY^2$ in each the polymeric reagents of Formulae I, Ia, Ic, Ib, II, IIa, IIc, IIb, III, IIIa, IIIc, IIIb, IV, IVa, IVc, IVb, V, Va, Vb, Vc, Vd, Ve, Vf and Vg are the same. It is possible, however, to have polymeric reagents wherein each of $POLY^1$ and $POLY^2$ is different. In addition, each of $POLY^1$ and $POLY^2$ will be typically (although not necessarily) a poly(alkylene oxide) such as a poly(ethylene glycol). Further, for a given poly(ethylene glycol), each poly(ethylene glycol) can be terminally capped with an end-capping moiety selected from the group consisting of hydroxyl, alkoxy, substituted alkoxy, alkenoxy, substituted alkenoxy, alkynoxy, substituted alkynoxy, aryloxy and substituted aryloxy. Preferred terminal capping groups, however, include methoxy. Exemplary weight average molecular weights for each poly(ethylene glycol) that serves as a $POLY^1$ and $POLY^2$ in Formulae I, Ia, Ic, Ib, II, IIa, IIc, IIb, III, IIIa, IIIc, IIIb, IV, IVa, IVc, IVb, V, Va, Vb, Vc, Vd, Ve, Vf and Vg include one or more of the following: in the range of from about 120 Daltons to about 6,000 Daltons; in the range of from about 6,000 Daltons to about 100,000 Daltons; in the range of from about 10,000 Daltons to about 85,000 Daltons; and in the range of from about 20,000 Daltons to about 85,000

Daltons. Exemplary architectures for a given poly(ethylene glycol) that serves as a POLY$^1$ and POLY$^2$ in Formulae I, Ia, Ic, Ib, II, IIa, IIc, IIb, III, IIIa, IIIc, IIIb, IV, IVa, IVc, IVb, V, Va, Vb, Vc, Vd, Ve, Vf and Vg include linear and branched. Exemplary first an second spacer moieties for each of Formulae I, Ia, Ic, Ib, II, IIa, IIc, IIb, III, IIIa, IIIc, IIIb, IV, IVa, IVc, IVb, V, Va, Vb, Vc, Vd, Ve, Vf and Vg include X$^1$ and X$^2$ spacer moieties independently selected from the group consisting of —NH—C(O)—CH$_2$—, —CH$_2$—C(O)—NH—, —NH—C(O)—CH$_2$—O—, —O—CH$_2$—C(O)—NH—, —CH$_2$—CH$_2$—NH—C(O)—CH$_2$—CH$_2$—CH$_2$—C(O)—NH—, —NH—C(O)—CH$_2$—CH$_2$—CH$_2$—C(O)—NH—CH$_2$—CH$_2$—, —O—CH$_2$—CH$_2$—NH—C(O)—CH$_2$—CH$_2$—C(O)—NH—, —NH—C(O)—CH$_2$—CH$_2$—CH$_2$—C(O)—NH—CH$_2$—CH$_2$—O—, —C(O)—NH—CH$_2$—CH$_2$—, —CH$_2$—CH$_2$—NH—C(O)—, —C(O)—NH—CH$_2$—CH$_2$—O—, and —O—CH$_2$—CH$_2$—NH—C(O)—. It is also preferred, with respect to Formulae I, Ia, Ic, Ib, II, IIa, IIc, IIb, III, IIIa, IIIc, IIIb, IV, IVa, IVc, IVb, V, Va, Vb, Vc, Vd, Ve, Vf and Vg that each of R$^1$ and R$^2$ is H, although lower alkyl (such as methyl and ethyl) is also contemplated. In addition, with respect to any electron altering groups present in any of Formulae I, Ic, Ib, II, IIc, IIb, III, IIIc, IIIb, IV, IVc, IVb, V, Vb, Vc, Vd, Ve, Vf and Vg each electron altering group is preferably halo, lower alkyl, aryl, substituted aryl, substituted arylakyl, alkoxy, aryloxy, alkylthio, arylthio, CF$_3$, —CH$_2$CF$_3$, —CH$_2$C$_6$F$_5$, —CN, —NO$_2$, —S(O)R, —S(O)Ar, —S(O$_2$)R, —S(O$_2$)Ar, —S(O$_2$)OR, —S(O$_2$)OAr, —S(O$_2$)NHR, —S(O$_2$)NHAr, —C(O)R, —C(O)Ar, —C(O)OR, —C(O)NHR, and the like, wherein Ar is aryl and R is H or an organic radical.

Another exemplary polymeric reagent has the following formula:

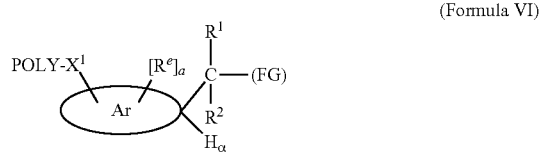

(Formula VI)

wherein:

POLY is a water-soluble polymer;

X is a spacer moiety that does not include a

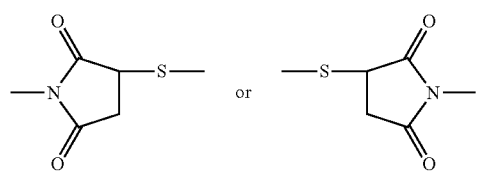

moiety;

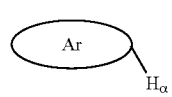

is an aromatic moiety bearing an ionizable hydrogen atom, H$_\alpha$;

R$^1$ is H or an organic radical;

R$^2$ is H or an organic radical;

R$^e$ is an electron altering group;

(a) is either zero or one; and (FG) is a functional group capable of reacting with an amino group of an active agent to form a degradable linkage.

Another exemplary polymeric reagent comprises the following structure:

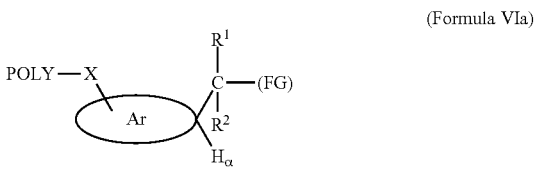

(Formula VIa)

wherein each of POLY, X, R$^1$, R$^2$, (a) and (FG) is as previously defined with respect to Formula VI.

The polymeric reagents corresponding to Formulae VI and VIa will typically (although not necessarily) have POLY be a poly(alkylene oxide) such as a poly(ethylene glycol). Further, the poly(ethylene glycol) can be terminally capped with an end-capping moiety selected from the group consisting of hydroxyl, alkoxy, substituted alkoxy, alkenoxy, substituted alkenoxy, alkynoxy, substituted alkynoxy, aryloxy and substituted aryloxy. Preferred terminal capping groups, however, include methoxy. Exemplary weight average molecular weights for a poly(ethylene glycol) that serves as a POLY in Formulae VI and VIa include one or more of the following: in the range of from about 120 Daltons to about 6,000 Daltons; in the range of from about 6,000 Daltons to about 100,000 Daltons; in the range of from about 10,000 Daltons to about 85,000 Daltons; and in the range of from about 20,000 Daltons to about 85,000 Daltons. Exemplary architectures for a poly(ethylene glycol) that serves as a POLY in Formulae VI and VIa include linear and branched. Exemplary second spacer moieties for Formulae VI and VIa include spacer moieties selected from the group consisting of —NH—C(O)—CH$_2$—, —CH$_2$—C(O)—NH—, —NH—C(O)—CH$_2$—O—, —O—CH$_2$—C(O)—NH—, —CH$_2$—CH$_2$—NH—C(O)—CH$_2$—CH$_2$—CH$_2$—C(O)—NH—, —NH—C(O)—CH$_2$—CH$_2$—CH$_2$—C(O)—NH—CH$_2$—CH$_2$—, —O—CH$_2$—CH$_2$—NH—C(O)—CH$_2$—CH$_2$—CH$_2$—C(O)—NH—, —NH—C(O)—CH$_2$—CH$_2$—CH$_2$—C(O)—NH—CH$_2$—CH$_2$—O—, —C(O)—NH—CH$_2$—CH$_2$—, —CH$_2$—CH$_2$—NH—C(O)—, —C(O)—NH—CH$_2$—CH$_2$—O—, and —O—CH$_2$—CH$_2$—NH—C(O)—. With respect to Formulae VI and VIa, each of R$^1$ and R$^2$ is preferably H although lower alkyl (such as methyl and ethyl) is also contemplated. With respect to Formula VIa, it is preferred that R$^e$ is halo, lower alkyl, aryl, substituted aryl, substituted arylakyl, alkoxy, aryloxy, alkylthio, arylthio, CF$_3$, —CH$_2$CF$_3$, —CH$_2$C$_6$F$_5$, —CN, —NO$_2$, —S(O)R, —S(O)Ar, —S(O$_2$)R, —S(O$_2$)Ar, —S(O$_2$)OR, —S(O$_2$)OAr, —S(O$_2$)NHR, —S(O$_2$)NHAr, —C(O)R, —C(O)Ar, —C(O)OR, —C(O)NHR, and the like, wherein Ar is aryl and R is H or an organic radical.

In some embodiments, it is preferred that the aromatic moiety for Formula VI (and the corresponding conjugate represented by Formula VI-C) is not one of the following:
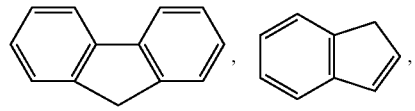 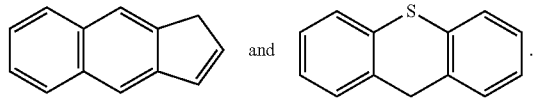
Examples of polymeric reagents of the invention include the following:
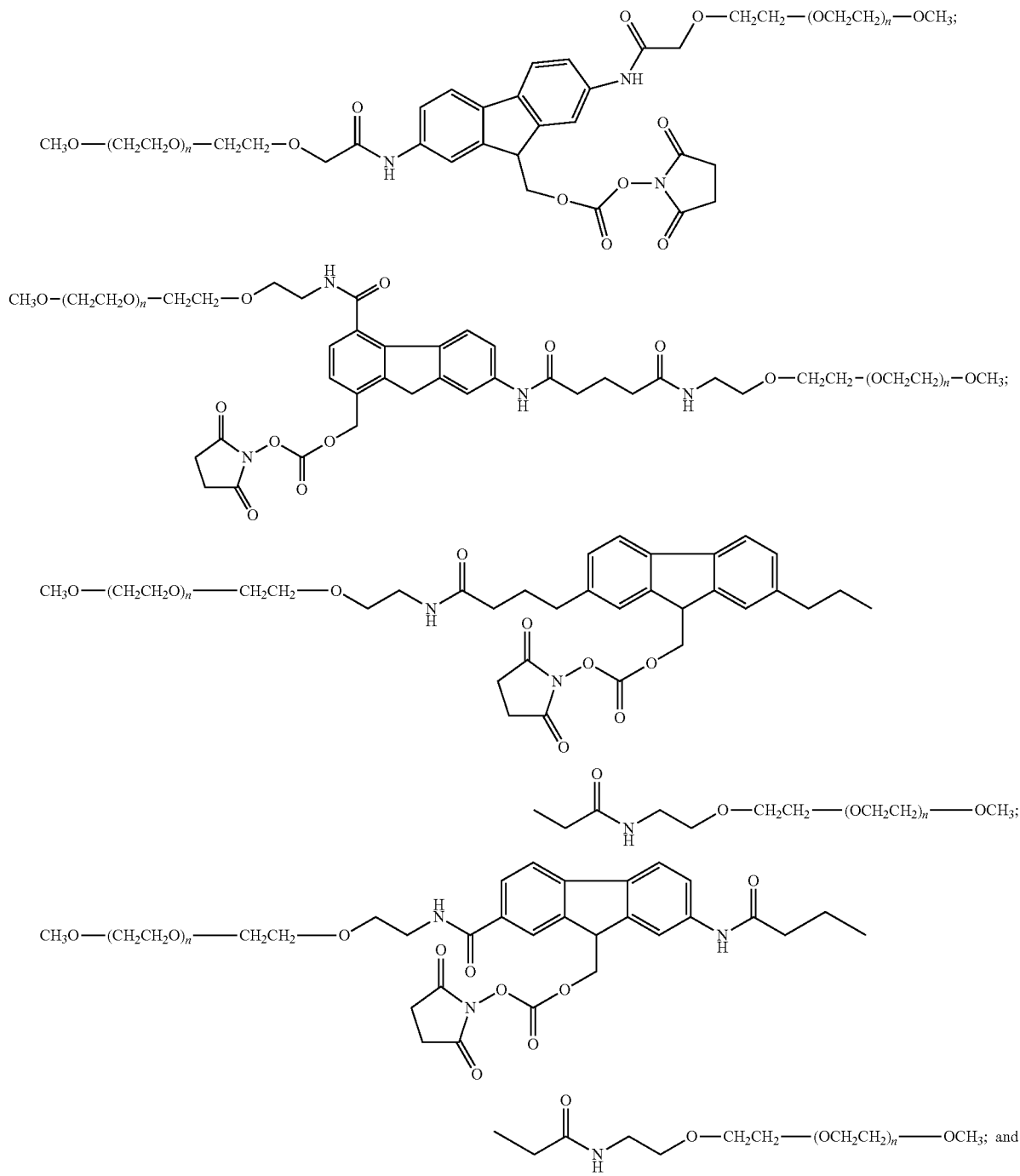

-continued

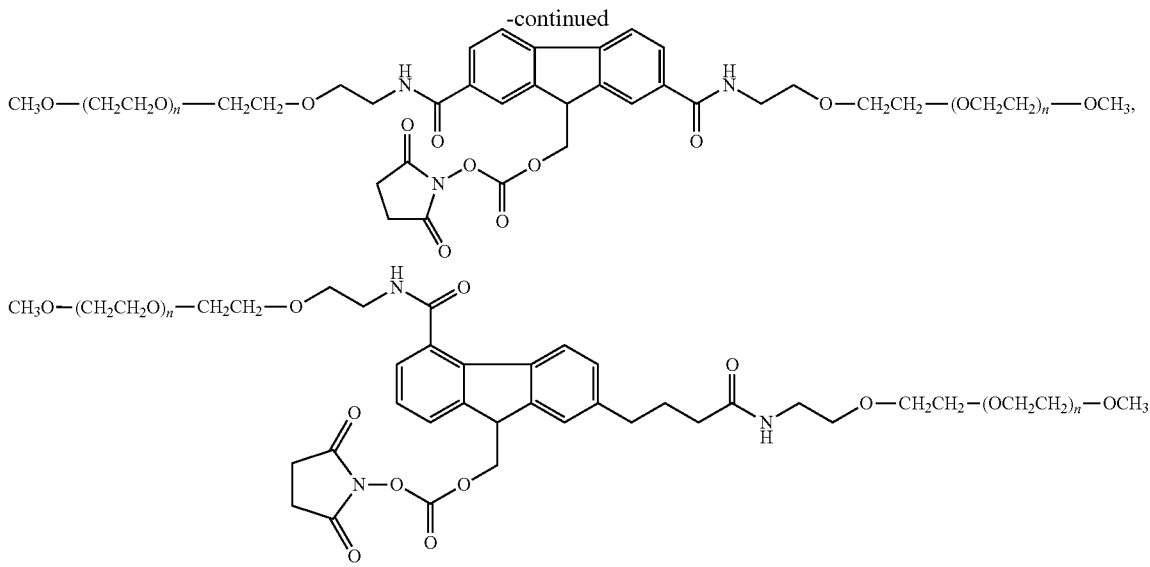

wherein each (n) is from 4 to 1500.

The polymeric reagents of the invention can be prepared in any number of ways. Consequently, the polymers provided herein are not limited to the specific technique or approach used in their preparation. Exemplary approaches for preparing the presently described polymer reagents, however, will be discussed in detail below In one method for preparing a polymeric reagent, the method comprises: (a) providing an aromatic-containing moiety bearing a first attachment site, a second attachment site and an optional third attachment site; (b) reacting a functional group reagent with the first attachment site to result in the first attachment site bearing a functional group capable of reacting with an amino group of an active agent and result in a degradable linkage, such as a carbamate; and (c) reacting a water-soluble polymer bearing a reactive group with the second attachment site and, when present, the optional third attachment site to result in (i) the second attachment site bearing a water-soluble polymer through a spacer moiety, wherein the spacer moiety does not include a

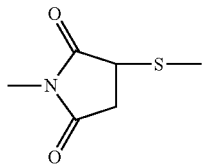

moiety, and (ii) the optional third attachment site, when present, bearing a second water-soluble polymer through a spacer moiety, wherein the spacer moiety does not include a not include a

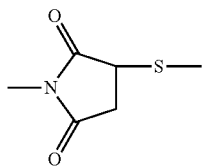

moiety. In some instances, (b) is performed before step (c) while in other instances, (c) is performed before step (b).

Thus, in this method for preparing a polymeric reagent, a required step is (a) providing an aromatic-containing moiety bearing a first attachment site, a second attachment site and an optional third attachment site. In the context of a synthetic preparation, it is understood that "providing" a material means to obtain the material (by, for example, synthesizing it or obtaining it commercially). An exemplary aromatic-containing moiety, for illustrative purposes, is 9-hydroxymethyl-2,7-diaminofluorene, as shown below.

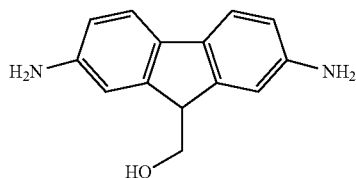

This aromatic-containing moiety, 9-hydroxymethyl-2,7-diaminofluorene, is an example of an aromatic-containing moiety having three attachment sites: a hydroxyl group at the 9 position and amino groups at each of the 2 and 7 positions. The aromatic-containing moiety can be provided in a base or salt form. With respect to 9-hydroxymethyl-2,7-diaminofluorene, it is possible to use the dihydrochloride form.

Having provided the aromatic-containing moiety, another step in the method broadly includes the step of reacting a water-soluble polymer bearing a reactive group with the attachment site(s) on the aromatic-containing moiety. Here, any art-known approach for attaching a water-soluble polymer to one or more attachment sites on the aromatic-containing moiety can be used and the method is not limited to the specific approach. For example, an amine reactive PEG (such as an N-succinimidyl ester-terminated mPEG, formed, for example, from the reaction of N hydroxysuccinimide and $CH_3O-CH_2CH_2-(OCH_2CH_2)-OCH_2CH_2-OCH_2COOH$ with dicyclohexyl carbodiimide (DCC) or diisopropyl carbodiimide (DIC) as condensing agent and optionally in the presence of a base) can be reacted with amine bearing aromatic-containing moiety such as 9-hydroxymethyl-2,7-diaminofluorene.

In some instances, reaction of the water-soluble polymer bearing a reactive group with the aromatic-containing moiety will result in all possible attachment sites having water-soluble polymer attached thereto. In such circumstances it is necessary to remove at least one water-soluble polymer so that an attachment site is made available for reaction with a functional group reagent. Thus, for example, reaction of the N-succinimidyl ester-terminated mPEG discussed in the previous paragraph with 9-hydroxymethyl-2,7-diaminofluorene results in a mixture comprising (a) a species bearing two water-soluble polymers, one at each of the two amine sites, and (b) a species bearing three water-soluble polymers, one at each of the two amine sites, and one at the hydroxyl site. Here, it is possible to remove and collect higher molecular weight species by using size-exclusion chromatography. In addition it is possible to treat the mixture to high pH [treating, for example, the mixture to lithium hydroxide (LiOH), sodium hydroxide (NaOH), potassium hydroxide (KOH)], followed by ion-exchange chromatography (IEC). In either case, the result is a composition containing mostly 9-hydroxymethyl-2,7-diaminofluorene bearing two water-soluble polymers, one at each of the two amine sites. A third hydroxyl site is thereby available for reaction with a functional group reagent.

The final step is reacting a reactive site of the aromatic-containing moiety with a functional group reagent. A preferred approach is to react the hydroxyl-containing 9-hydroxymethyl-2,7-diaminofluorene bearing two water-soluble polymers, one at each of the two amine sites with triphosgene followed by treatment with N-hydroxysuccinimide. In this way, a functional group capable of reacting with an amino group of an active agent to form a degradable linkage, such as a carbamate linkage (in this case, an "activated carbonate") is formed on the hydroxyl-containing reactive site.

The steps of the method take place in an appropriate solvent. One of ordinary skill in the art can determine whether any specific solvent is appropriate for any given reaction. Typically, however, the solvent is preferably a nonpolar solvent or a polar aprotic solvent. Nonlimiting examples of nonpolar solvents include benzene, xylene, dioxane, tetrahydrofuran (THF), t-butyl alcohol and toluene. Particularly preferred nonpolar solvents include toluene, xylene, dioxane, tetrahydrofuran, and t-butyl alcohol. Exemplary polar aprotic solvents include, but are not limited to, DMSO (dimethyl sulfoxide), HMPA (hexamethylphosphoramide), DMF (dimethylformamide), DMA (dimethylacetamide), NMP (N-methylpyrrolidinone).

An alternative approach starts with fluorene diamine, a readily available starting material. A schematic of the reaction (showing the synthetic steps sufficient to provide a conjugate) is shown below.

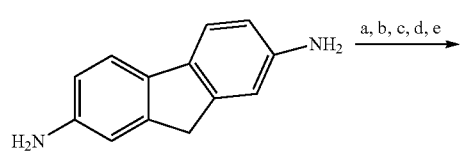

-continued

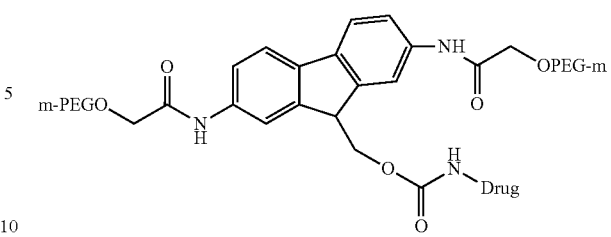

a = amine protection;
b = formylation, reduction, deprotection;
c = optional chromatography;
d = mPEG—CM, DCC, HOBT;
e = DSC, Drug-NH$_2$ In this approach, carboxylmethyl-terminated PEG ("PEG-CM" available from Nektar Therapeutics) can be reacted with the fluorene diamine to provide an intermediate that can subsequently be used to form a conjugate with an active agent ("Drug-NH$_2$"). The fluorene diamine has two amido groups attached to the aromatic nucleus and hence has a mild effect (relative to the hydrogens these groups replaced) on the acidity (i.e., pKa value) of the ionizable hydrogen atom (i.e., H$_\alpha$). Thus, the release rate of drug is moderate to slow.

Likewise, in another approach based on an amine reagent such as the commercially available mPEG propionic acid ester, "mPEG-SPA," the synthesis is slightly different but the net result on the drug release rate is minimal. A schematic of this approach (showing the synthetic steps sufficient to provide a conjugate) is shown below.

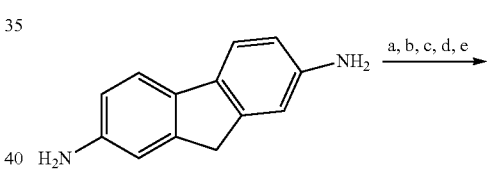

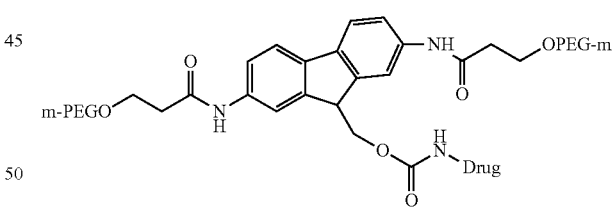

a = amine protection;
b = formylation, reduction, deprotection;
c = optional chromatography;
d = mPEG—SPA, base;
e = DSC, Drug-NH$_2$ The difference in drug release rate is minimal because the aromatic ring substituents resulting from reaction with mPEG-CM and mPEG-SPA are similar.

One can modify the synthetic method significantly by augmenting the amine group by reaction with a reagent like succinic anhydride or glutaric anhydride to give a terminal carboxylic acid. A schematic (showing the synthetic steps sufficient to provide a conjugate) of this approach is shown below.

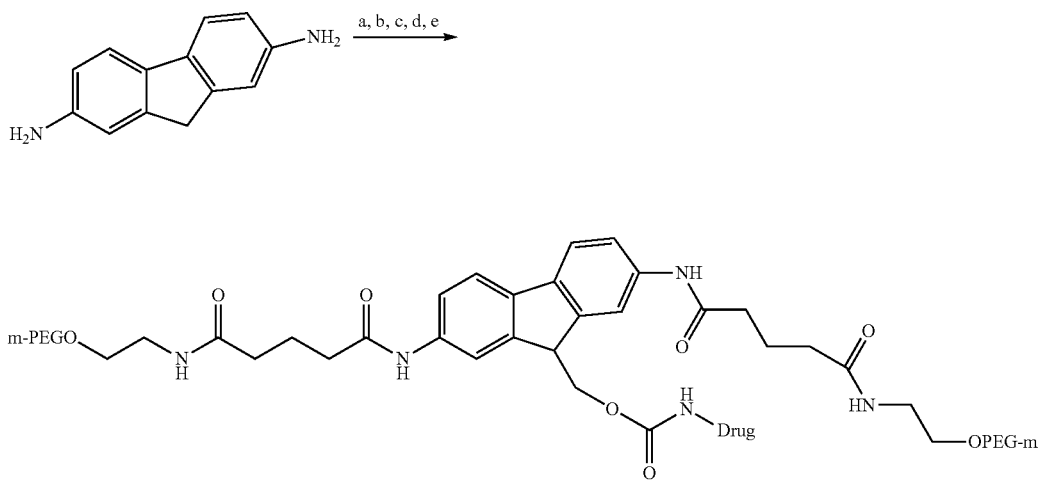

a = amine protection;
b = formylation, reduction, deprotection;
c = glutaric anhydride;
d = mPEG amine, DCC, HOBT;
e = DSC, Drug-NH$_2$ In this approach, the result allows for the use of a PEG amine as the PEGylating reagent as opposed to a PEG carboxylic acid or active ester. Thus, it is possible to achieve yet another method for synthesis of the reagent but the net result on the release rate of the drug is not substantially changed, as the aromatic ring substituent remains an amido group.

A significant change in drug release rate can be made to occur if one or more of the aromatic ring of the three reagents above, at some stage in the synthesis, is augmented by further substitution. For example, one may bring about ring substitution with, for example, a sulfonic acid group or a nitro group. Either of these groups, being strongly electron withdrawing, would have a significant effect on the acidity (pKa value) of the ionizable hydrogen atom (H$_\alpha$).

Another example to demonstrate the ability to influence the drug release rate in the final reagent-drug conjugate is illustrated below.

Here, the starting fluorene derivative contains a carboxylic acid group. This readily available raw material can be subjected to reaction conditions that allow introduction of an amino group in the remote aromatic ring. Then, using chemistry similar to that in the examples above, it is possible to provide a reagent that has an amido group on one aromatic ring and a carboxamide group on the other ring. This combination of ring substituents is net electron withdrawing compared to those examples above that have two amido groups and hence the effect on the acidity (pKa value) of the ionizable hydrogen atom (H$_\alpha$) is such that the drug release rate is enhanced.

A more significant enhancement to the drug release rate can be achieved by using a different type of amide linkage. It is possible to prepare sulfonamides using the series of reactions illustrated below (showing the synthetic steps sufficient to provide a conjugate).

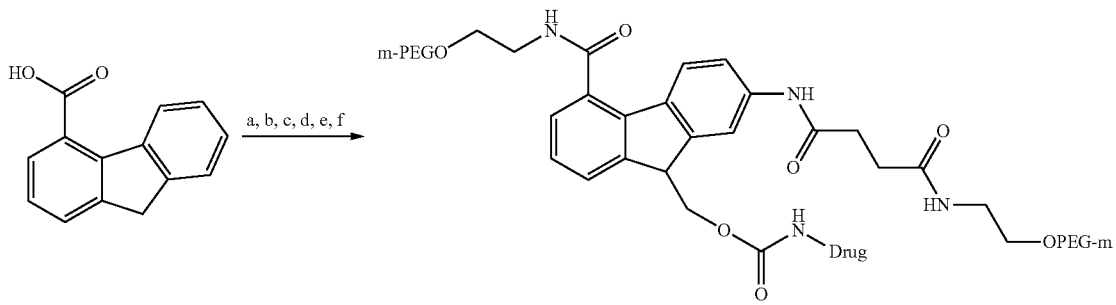

a = nitration, nitro group reduction;
b = amine protection;
c = formylation, reduction, deprotection;
d = glutaric anhydride;
e = mPEG amine, DCC, HOBT;
f = DSC, Drug-NH$_2$

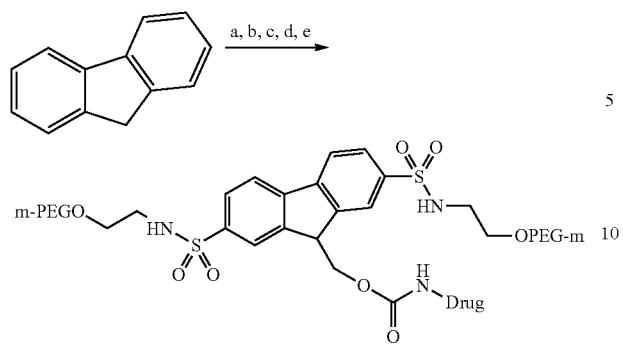

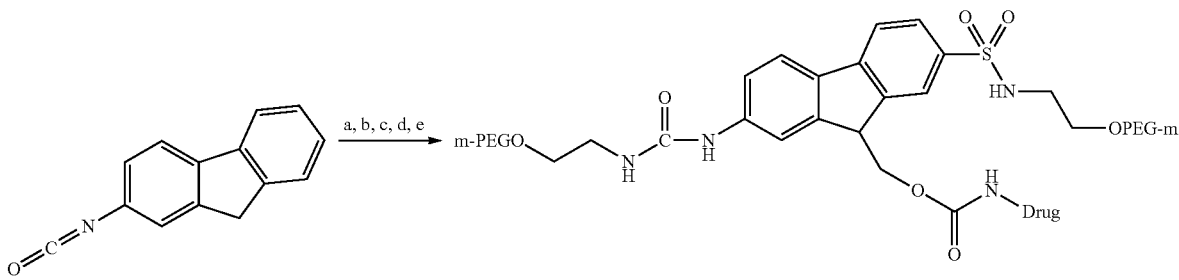

a = mPEG amine, catalyst;
b = formulation, reduction, hydroxyl group protection;
c = ClSO₃H, hydrolysis, chromatography;
d = thionyl chloride then mPEG amine, hydroxyl group deprotection;
e = DSC, Drug-NH₂

-continued a = Formulation, reduction, hydroxy group protection;
b = ClSO₃H, hydrolysis, chromatography;
c = thionyl chloride then mPEGNH₂;
d = hydroxyl group deprotection;
e = DSC, Drug-NH₂

The sulfonyl groups attached to each ring, being highly electronegative groups, affect the acidity (pKa value) of the ionizable hydrogen atom ($H_\alpha$). Hence, the drug release rates of these conjugates would be relatively fast.

In another example, a drug conjugate with an intermediate release rate is illustrated (showing the synthetic steps sufficient to provide a conjugate).

In this case, using the commercially available isocyanate raw material, a ureido group and sulfonamido group are attached to the aromatic nuclei. The ureido group, like the amido group above, has a mild effect but the sulfonamido group has a strong effect. The net result is that conjugates prepared from this reagent would have a release rate in between that of the bis sulfonamido just discussed and the other conjugates discussed earlier.

One advantage that some synthetic routes have over others is the optional use of ion exchange chromatography to purify the reagent at an intermediate stage. Because there may be several impurities formed along the way, this may be a quite significant advantage to a method.

An example is shown below of the insertion via chemical reaction of an electron withdrawing sulfonic acid group at an intermediate stage in the preparation of the glutaric anhydride modified diaminofluorene, from a synthesis illustrated above "m-PEG" and "PEG-m" represent methoxy poly(ethylene glycol).

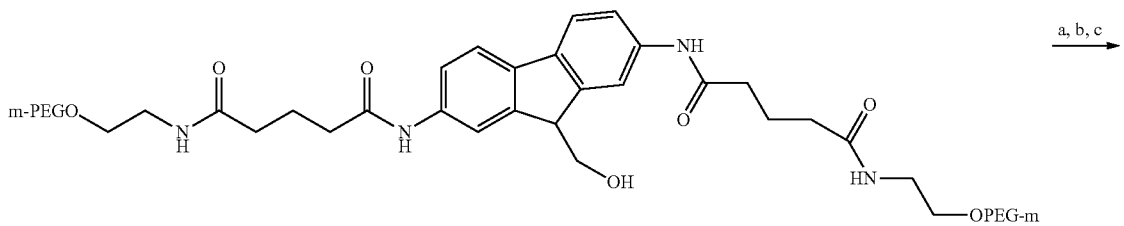

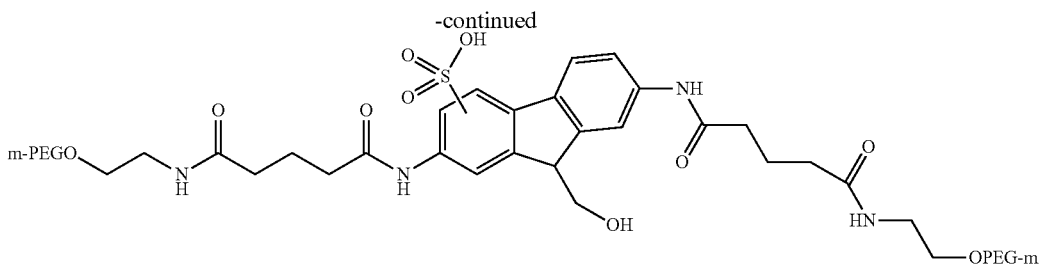

-continued a = hydroxyl group protection;
b = ClSO₃H, hydrolysis, optional chromatography;
c = hydroxyl group deprotection In this case, it is possible to block the hydroxyl group to prevent formation of the sulfate ester and then carry out an electrophilic aromatic sulfonation process using chlorosulfonic acid. A mixture of mono- and disulfonation products may result. This mixture, if it forms, may be readily purified to provide either form in a rather pure state. Also, since that synthesis did not have an optional chromatography step already in place, this provides an opportunity to remove neutral impurities that may have been carried along from earlier steps.

An example of using a sulfonyl group both to enhance the acidity of the alpha hydrogen and as a site for addition of the polymer chain is shown in the schematic below. In this case the aromatic moiety contains a single pyridine ring in the commercially available alcohol, which serves as the starting point for making the polymeric reagent. The presence of the nitrogen in the aromatic ring makes this ring more electron withdrawing, compared to a phenyl ring, and thus the acidity of the alpha hydrogen is increased. However, the acidity of the alpha hydrogen can be further increased to make it relatively more removable. Attachment of a sulfonyl group increases the acidity of the hydrogen. The steps required to add the sulfonyl group are provided in the schematic below [wherein diBTC is di(1-benzotriazolyl)carbonate and BTC is a benzotriazolyl radical].

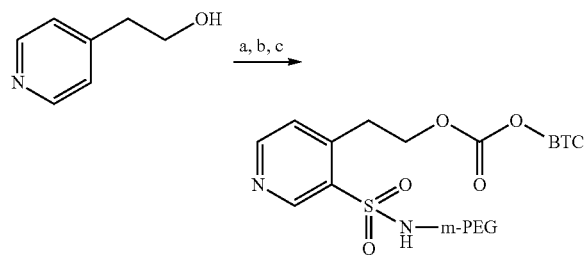

a = ClSO₃H, then, hydrolysis, purification by ion exchange chromatography;
b = thonyl chloride, then mPEG—NH₂ (20 kD), then removal of ionic impurities using ion exchange chromatography;
c = diBTC The approach shown above demonstrates the addition of an electronic altering group (on a single ringed aromatic moiety and for a polymeric reagent containing a single water-soluble polymer. While two water-soluble polymers are preferred in some embodiments, other embodiments will prefer incorporation of a single water-soluble polymer (e.g., when the total size of the polymeric reagent is desired to be relatively small).

Other electron altering groups may be added in a similar fashion. For example, aromatic nitration by combining nitric acid in the presence of sulfuric acid results in a nitro group (i.e., —NO₂) being attached to the aromatic system. In addition, halogenation methods such as combining the aromatic system with a halogen in the present of a metal catalyst (such as iron) results in a halo group being attached to the aromatic system. With regard to halogenation methods wherein a metal ion is present, it is preferred (for reasons explained herein) to first carry out the step of adding the halo group to the aromatic system and subsequently remove any metal ions and then attach one or more water-soluble polymers to the aromatic system. Further, alkylation and acylation methods such as a Friedel-Crafts reaction can be used to add an electron altering alkyl or acyl group (respectively) to the aromatic system by adding an alkyl halide (e.g., isobutyl chloride) or acyl halide (e.g., propionyl chloride) to the aromatic system in the presence of a metal catalyst (such as aluminum). Again, because a metal catalyst is typically required to carry out such reactions, it is preferred to first carry out the step of adding the alkyl group to the aromatic system and subsequently remove any metal ions and then attach one or more water-soluble polymers to the aromatic system.

During preparation and handling of the polymeric reagents (as well the preparation and handling of the corresponding conjugates), it is preferred to prevent the introduction of metal ions. For example, because metal ions are well known to be coordinated by PEGs, the avoidance of metal ions is preferred. In addition, metal ions are known to catalyze PEG chain oxidation. In particular, when PEG is attached to an electron rich aromatic system, the presence of a metal ion coordinated to the PEG chain may provide a route for electron transfer from the aromatic nucleus to the PEG-metal ion complex and facilitate PEG chain cleavage. Thus, the invention includes methods and compositions wherein metal ions are substantially absent.

These and other approaches for preparing the polymeric reagents described herein can be used.

Once prepared, the polymeric reagents can be isolated. Known methods can be used to isolate the polymeric reagent, but it is particularly preferred to use chromatography, e.g., size exclusion chromatography. Alternately or in addition, the method includes the step of purifying the polymeric reagent once it is formed. Again, standard art-known purification methods can be used to purify the polymeric reagent.

The polymeric reagents of the invention are sensitive to moisture and oxygen and are ideally stored under an inert atmosphere, such as under argon or under nitrogen, and at low temperature. In this way, potentially degradative processes associated with, for example, atmospheric oxygen, are reduced or avoided entirely. In some cases, to avoid oxidative degradation, antioxidants, such as butylated hydroxyl toluene (BHT), can be added to the polymeric reagent prior to storage. In addition, it is preferred to minimize the amount of moisture associated with the storage conditions to reduce potentially damaging reactions associated with water, e.g. hydrolysis of the active ester. Moreover, it is preferred to keep the storage conditions dark in order to prevent certain degradative processes that involve light. Thus, preferred storage conditions include one or more of the following: storage under dry argon or another dry inert gas; storage at temperatures below about −15° C.; storage in the absence of light; and storage with a suitable amount (e.g., about 50 to about 500 parts per million) of an antioxidant such as BHT.

The above-described polymeric reagents are useful for conjugation to biologically active agents. For example, an amino group (e.g., primary amine) on an active agent will react with the functional group capable of reacting with an amino group of an active agent to form a degradable linkage, such as a carbamate linkage. Thus, the invention comprises a conjugate formed with any polymeric reagent described herein.

Exemplary conjugates include those of the following formula:

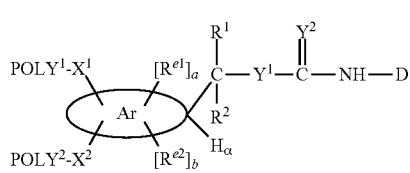

(Formula I-C)

wherein:

POLY$^1$ is a first water-soluble polymer;

POLY$^2$ is a second water-soluble polymer;

X$^1$ is a first spacer moiety;

X$^2$ is a second spacer moiety;

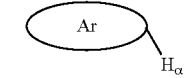

is an aromatic-containing moiety bearing an ionizable hydrogen atom, H$_\alpha$;

R$^1$ is H or an organic radical;

R$^2$ is H or an organic radical;

(a) is either zero or one;

(b) is either zero or one;

R$^{e1}$, when present, is a first electron altering group;

R$^{e2}$, when present, is a second electron altering group;

Y$^1$ is O or S;

Y$_2$ is O or S; and

D is a residue of a biologically active agent.

Conjugates corresponding to this Formula I-C can be prepared using polymeric reagents corresponding to Formula I.

When the conjugate corresponding to Formula I-C has no discrete electron altering groups [i.e., when (a) and (b) are both zero with regard to Formula I-C], a conjugate of the following formula results:

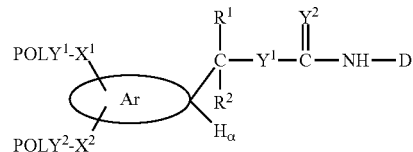

(Formula Ia-C)

wherein each of POLY$^1$, POLY$^2$, X$^1$, X$^2$, R$^1$, R$^2$,

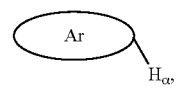

Y$^1$, Y$^2$, and D is as previously defined with respect to Formula I-C. Conjugates corresponding to this Formula Ia-C can be prepared using polymeric reagents corresponding to Formula Ia.

When the conjugate corresponding to Formula I-C has a single discrete electron altering group [e.g., when (a) is one and (b) is zero with regard to Formula I-C], a conjugate of the following formula results:

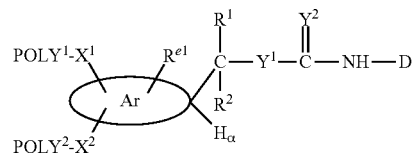

(Formula Ic-C)

wherein each of POLY$^1$, POLY$^2$, X$^1$, X$^2$, R$^1$, R$^2$,

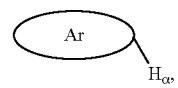

Y$^1$, Y$^2$, D, and R$^{e1}$ is as previously defined with respect to Formula I-C. Conjugates corresponding to this Formula Ic-C can be prepared using polymeric reagents corresponding to Formula Ic.

When the conjugate corresponding to Formula I-C has two discrete electron altering groups [i.e., when (a) and (b) are both one with regard to Formula I-C], a conjugate of the following formula results:

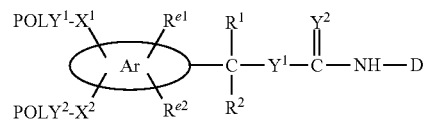

(Formula Ib-C)

wherein each of POLY$^1$, POLY$^2$, X$^1$, X$^2$, R$^1$, R$^2$,

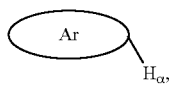

$Y^1, Y^2, D, R^{e1}$ and $R^{e2}$ is as previously defined with respect to Formula I-C. Conjugates corresponding to this Formula Ib-C can be prepared using polymeric reagents corresponding to Formula Ib.

In some cases, the conjugate can include individual aromatic moieties that are only linked to each other through a carbon atom bearing an ionizable hydrogen atom. Such a conjugate has the following formula:

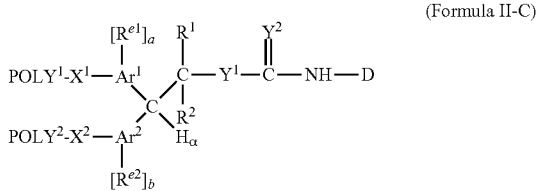

(Formula II-C)

wherein:
$POLY^1$ is a first water-soluble polymer;
$POLY^2$ is a second water-soluble polymer;
$X^1$ is a first spacer moiety;
$X^2$ is a second spacer moiety;
$Ar^1$ is a first aromatic moiety;
$Ar^2$ is a second aromatic moiety;
$H_\alpha$ is an ionizable hydrogen atom;
$R^1$ is H or an organic radical;
$R^2$ is H or an organic radical;
(a) is either zero or one;
(b) is either zero or one;
$R^{e1}$, when present, is a first electron altering group;
$R^{e2}$, when present, is a second electron altering group;
$Y^1$ is O or S;
$Y_2$ is O or S; and
D is a residue of a biologically active agent. Conjugates corresponding to this Formula II-C can be prepared using polymeric reagents corresponding to Formula II.

When the conjugate corresponding to Formula II-C has no discrete electron altering groups [i.e., when (a) and (b) are both zero with regard to Formula II-C], a conjugate of the following formula results:

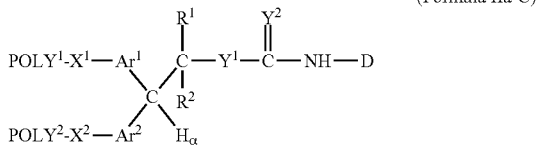

(Formula IIa-C)

wherein each of $POLY^1, POLY^2, X^1, X^2, R^1, R^2, Ar^1, Ar^2, Y^1, Y^2$ and D is as previously defined with respect to Formula II-C. Conjugates corresponding to this Formula IIa-C can be prepared using polymeric reagents corresponding to Formula IIa.

When the conjugate corresponding to Formula II has a single discrete electron altering group [e.g., when (a) is one and (b) is zero with regard to Formula II], a conjugate of the following formula results:

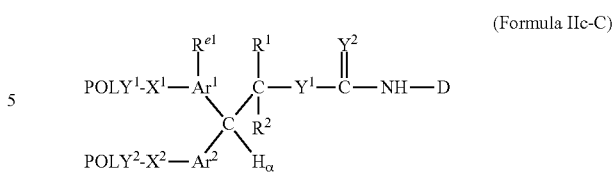

(Formula IIc-C)

wherein each of $POLY^1, POLY^2, X^1, X^2, Ar^1, Ar^2, H_\alpha, R^1, R^2, R^{e1}, Y^1, Y^2$ and D is as previously defined with respect to Formula II-C. Conjugates corresponding to this Formula IIc-C can be prepared using polymeric reagents corresponding to Formula IIc.

When the conjugate corresponding to Formula II-C has two discrete electron altering groups [i.e., when (a) and (b) are both one with regard to Formula II-C], a conjugate of the following formula results:

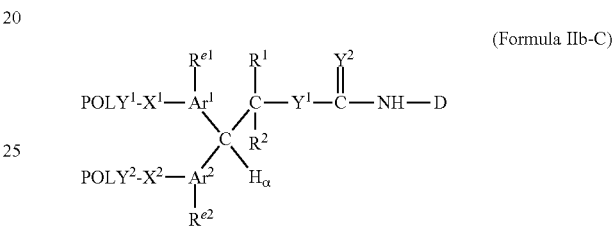

(Formula IIb-C)

wherein each of $POLY^1, POLY^2, X^1, X^2, Ar^1, Ar^2, H_\alpha, R^1, R^2, Y^1, Y^2, D, R^{e1}$ and $R^{e2}$ is as previously defined with respect to Formula II-C. Conjugates corresponding to this Formula IIb-C can be prepared using polymeric reagents corresponding to Formula III).

In still other cases, the conjugate can include individual aromatic moieties that are linked to each other both through a carbon atom bearing an ionizable hydrogen atom as well as another direct bond. Such a conjugate has the following formula:

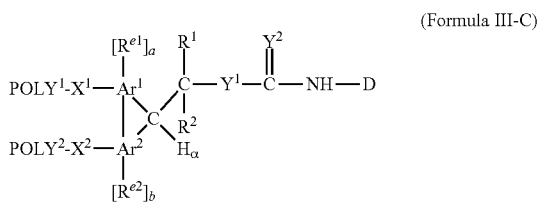

(Formula III-C)

wherein:
$POLY^1$ is a first water-soluble polymer;
$POLY^2$ is a second water-soluble polymer;
$X^1$ is a first spacer moiety;
$X^2$ is a second spacer moiety;
$Ar^1$ is a first aromatic moiety;
$Ar^2$ is a second aromatic moiety;
$H_\alpha$ is an ionizable hydrogen atom;
$R^1$ is H or an organic radical;
$R^2$ is H or an organic radical;
(a) is either zero or one;
(b) is either zero or one;
$R^{e1}$, when present, is a first electron altering group;
$R^{e2}$, when present, is a second electron altering group;
$Y^1$ is O or S;
$Y_2$ is O or S; and
D is a residue of a biologically active agent.

Conjugates corresponding to this Formula III-C can be prepared using polymeric reagents corresponding to Formula III.

When the conjugate corresponding to Formula III-C has no discrete electron altering groups [i.e., when (a) and (b) are both zero with regard to Formula III-C], a conjugate of the following formula results:

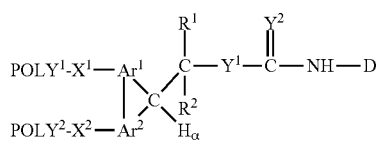
(Formula IIIa-C)

wherein each of POLY$^1$, POLY$^2$, X$^1$, X$^2$, R$^1$, R$^2$, Ar$^1$, Ar$^2$, Y$^1$, Y$^2$ and D is as previously defined with respect to Formula III-C. Conjugates corresponding to this Formula IIIc-C can be prepared using polymeric reagents corresponding to Formula IIIa.

When the conjugate corresponding to Formula III-C has a single discrete electron altering group [e.g., when (a) is one and (b) is zero with regard to Formula III-C], a conjugate of the following formula results:

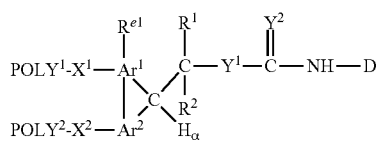
(Formula IIIc-C)

wherein each of POLY$^1$, POLY$^2$, X$^1$, X$^2$, R$^1$, R$^2$, Ar$^1$, Ar$^2$, R$^{e1}$, Y$^1$, Y$^2$ and D is as previously defined with respect to Formula III-C. Conjugates corresponding to this Formula IIIc-C can be prepared using polymeric reagents corresponding to Formula IIIc.

When the conjugate corresponding to Formula III-C has two discrete electron altering groups [i.e., when (a) and (b) are both one with regard to Formula III-C], a conjugate of the following formula results:

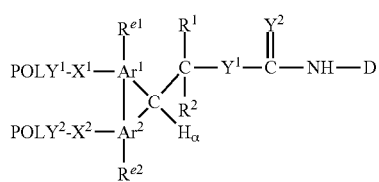
(Formula IIIb-C)

wherein each of POLY$^1$, POLY$^2$, X$^1$, X$^2$, R$^1$, R$^2$, Ar$^1$, Ar$^2$, R$^{e1}$, R$^{e2}$, Y$^1$, Y$^2$ and D is as previously defined with respect to Formula III-C. Conjugates corresponding to this Formula IIIb-C can be prepared using polymeric reagents corresponding to Formula IIIb.

In still other cases, the conjugate can include individual aromatic moieties that are linked to each other both through a carbon atom bearing an ionizable hydrogen atom as well as a spacer moiety of one or more atoms. Such a conjugate has the following formula:

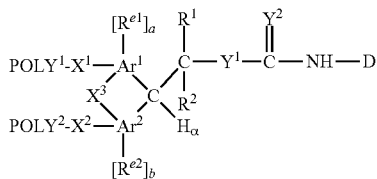
(Formula IV-C)

wherein:
POLY$^1$ is a first water-soluble polymer;
POLY$^2$ is a second water-soluble polymer;
X$^1$ is a first spacer moiety;
X$^2$ is a second spacer moiety;
X$^3$ is a third spacer moiety;
Ar$^1$ is a first aromatic moiety;
Ar$^2$ is a second aromatic moiety;
H$_\alpha$ is an ionizable hydrogen atom;
R$^1$ is H or an organic radical;
R$^2$ is H or an organic radical;
(a) is either zero or one;
(b) is either zero or one;
R$^{e1}$, when present, is a first electron altering group;
R$^{e2}$, when present, is a second electron altering group;
Y$^1$ is O or S;
Y$_2$ is O or S; and
D is a residue of a biologically active agent. Conjugates corresponding to this Formula IV-C can be prepared using polymeric reagents corresponding to Formula IV.

When the conjugate corresponding to Formula IV-C has no discrete electron altering groups [i.e., when (a) and (b) are both zero with regard to Formula IV-C], a conjugate of the following formula results:

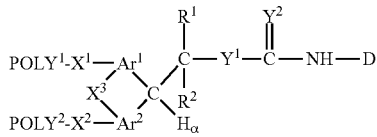
(Formula IVa-C)

wherein each of POLY$^1$, POLY$^2$, X$^1$, X$^2$, X$^3$, R$^1$, R$^2$, Ar$^1$, Ar$^2$, Y$^1$, Y$^2$ and D is as previously defined with respect to Formula IV-C. Conjugates corresponding to this Formula IVa-C can be prepared using polymeric reagents corresponding to Formula IVa.

When the conjugate corresponding to Formula IV-C has a single discrete electron altering group [e.g., when (a) is one and (b) is zero with regard to Formula IV-C], a conjugate of the following formula results:

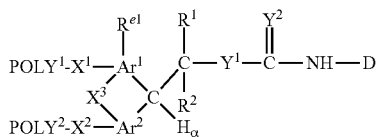
(Formula IVc-C)

wherein each of POLY$^1$, POLY$^2$, X$^1$, X$^2$, X$^3$, R$^1$, R$^2$, Ar$^1$, Ar$^2$, R$^{e1}$, Y$^1$, Y$^2$ and D is as previously defined with respect to Formula IV-C. Conjugates corresponding to this Formula IVc-C can be prepared using polymeric reagents corresponding to Formula IVc.

When the conjugate corresponding to Formula IV-C has two discrete electron altering groups [i.e., when (a) and (b) are both one with regard to Formula IV-C], a conjugate of the following formula results:

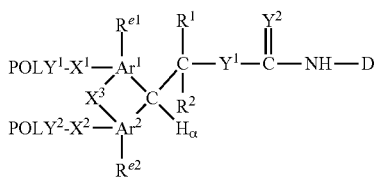

(Formula IVb-C)

wherein each of $POLY^1$, $POLY^2$, $X^1$, $X^2$, $X^3$, $Ar^1$, $Ar^2$, $H_\alpha$, $R^1$, $R^2$, $R^{e1}$, $R^{e2}$, $Y^1$, $Y^2$ and D is as previously defined with respect to Formula IV-C. Conjugates corresponding to this Formula IVb-C can be prepared using polymeric reagents corresponding to Formula IVb.

A preferred conjugate comprises the following structure:

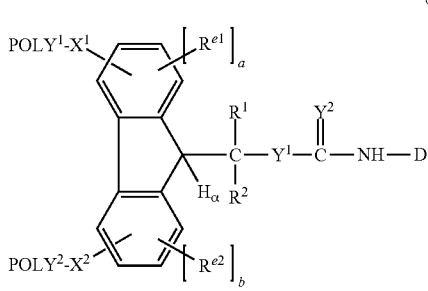

(Formula V-C)

wherein:

$POLY^1$ is a first water-soluble polymer;

$POLY^2$ is a second water-soluble polymer;

$X^1$ is a first spacer moiety;

$X^2$ is a second spacer moiety;

$H_\alpha$ is an ionizable hydrogen atom;

$R^1$ is H or an organic radical;

$R^2$ is H or an organic radical;

(a) is either zero or one;

(b) is either zero or one;

$R^{e1}$, when present, is a first electron altering group;

$R^{e2}$, when present, is a second electron altering group;

$Y^1$ is O or S;

$Y_2$ is O or S; and

D is a residue of a biologically active agent bearing an amine functional group.

Conjugates corresponding to this Formula V-C can be prepared using polymeric reagents corresponding to Formula V.

When the conjugate corresponding to Formula V-C has no discrete electron altering groups [i.e., when (a) and (b) are both zero with regard to Formula V-C], a conjugate of the following formula results:

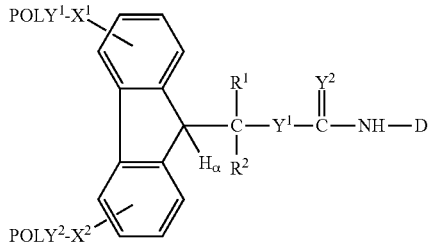

(Formula Va-C)

wherein each of $POLY^1$, $POLY^2$, $X^1$, $X^2$, $H_\alpha$, $R^1$, $R^2$, $Y^1$, $Y^2$ and D is as previously defined with respect to Formula V-C. Conjugates corresponding to this Formula Va-C can be prepared using polymeric reagents corresponding to Formula Va.

When the conjugate corresponding to Formula V-C has a single discrete electron altering group [e.g., when (a) is one and (b) is zero with regard to Formula V-C], a conjugate of the following formula results:

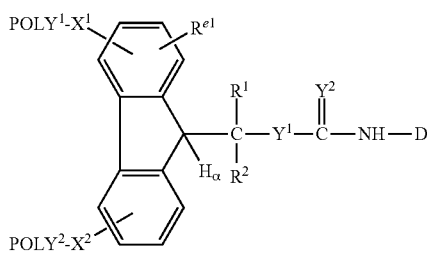

(Formula Vc-C)

wherein each of $POLY^1$, $POLY^2$, $X^1$, $X^2$, $H_\alpha$, $R^1$, $R^2$, $R^{e1}$, $Y^1$, $Y^2$ and D is as previously defined with respect to Formula V-C. Conjugates corresponding to this Formula Vc-C can be prepared using polymeric reagents corresponding to Formula Vc.

When the conjugate corresponding to Formula V-C has two discrete electron altering groups [i.e., when (a) and (b) are both one with regard to Formula V-C], a conjugate of the following formula results:

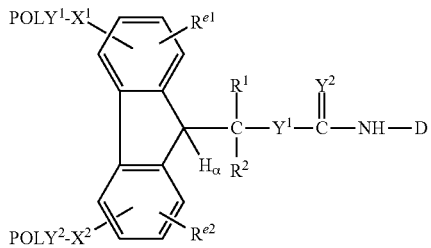

(Formula Vb-C)

wherein each of $POLY^1$, $POLY^2$, $X^1$, $X^2$, $R^1$, $R^2$, $H_\alpha$, $R^{e1}$, $R^{e2}$, $Y^1$, $Y^2$ and $R^{e2}$ and D is as previously defined with respect to Formula V-C. Conjugates corresponding to this Formula Vb-C can be prepared using polymeric reagents corresponding to Formula Vb.

Still another preferred conjugate is of the following structure:

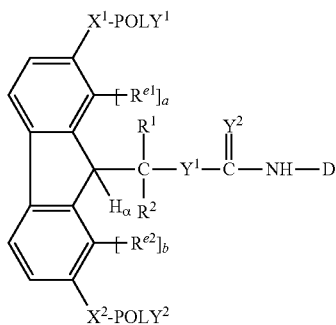

(Formula Vd-C)

wherein each of POLY$^1$, POLY$^2$, X$^1$, X$^2$, R$^1$, R$^2$, H$_\alpha$, R$^{e1}$, R$^{e2}$, (a), (b), Y$^1$, Y$^2$ and D is as previously defined with respect to Formula V-C, with the proviso that R$^{e1}$ is H when (a) is zero and R$^{e2}$ is H when (b) is zero. Conjugates corresponding to this Formula Vd-C can be prepared using polymeric reagents corresponding to Formula Vd.

Still another preferred conjugate is of the following structure:

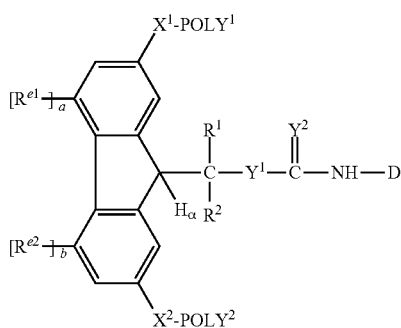

(Formula Ve-C)

wherein each of POLY$^1$, POLY$^2$, X$^1$, X$^2$, R$^1$, R$^2$, H$_\alpha$, R$^{e1}$, R$^{e2}$, Y$^1$, Y$^2$ and R$^{e2}$ and D is as previously defined with respect to Formula V-C, with the proviso that R$^{e1}$ is H when (a) is zero and R$^{e2}$ is H when (b) is zero. Conjugates corresponding to this Formula Ve-C can be prepared using polymeric reagents corresponding to Formula Ve.

Still another preferred conjugate is of the following structure:

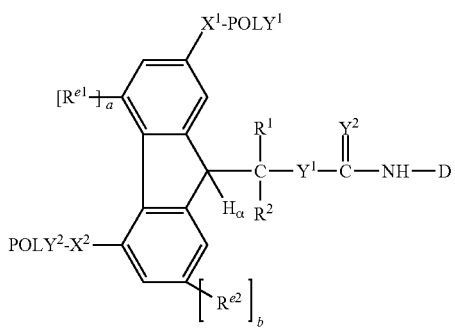

(Formula Vf-C)

wherein each of POLY$^1$, POLY$^2$, X$^1$, X$^2$, R$^1$, R$^2$, H$_\alpha$, R$^{e1}$, R$^{e2}$, Y$^1$, Y$^2$ and D is as previously defined with respect to Formula V-C, with the proviso that R$^{e1}$ is H when (a) is zero and R$^{e2}$ is H when (b) is zero. Conjugates corresponding to this Formula Vf-C can be prepared using polymeric reagents corresponding to Formula Vf.

Still another preferred conjugate is of the following structure:

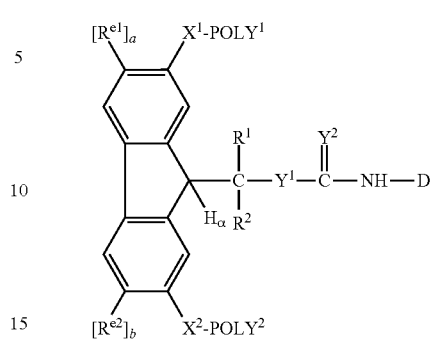

(Formula Vg-C)

wherein each of POLY$^1$, POLY$^2$, X$^1$, X$^2$, R$^1$, R$^2$, H$_\alpha$, R$^{e1}$, R$^{e2}$, Y$^1$, Y$^2$ and D is as previously defined with respect to Formula V-C, with the proviso that R$^{e1}$ is H when (a) is zero and R$^{e2}$ is H when (b) is zero. Conjugates corresponding to this Formula Vg-C can be prepared using polymeric reagents corresponding to Formula Vg.

Another exemplary conjugate of the invention has the following formula:

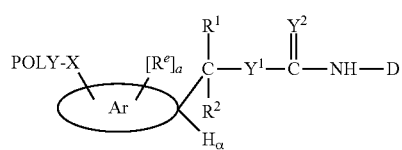

(Formula VI-C)

wherein:
POLY is a water-soluble polymer;
X is a spacer moiety that does not include a

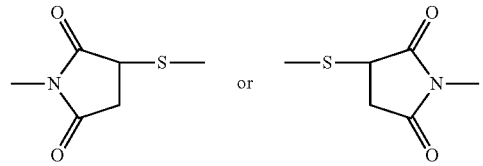

moiety;

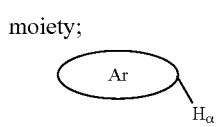

is an aromatic moiety;
R$^1$ is H or an organic radical;
R$^2$ is H or an organic radical;
R$^e$ is an electron altering group;
(a) is either zero or one; and
Y$^1$ is O or S;
Y$_2$ is O or S; and
D is a residue of a biologically active agent bearing an amine functional group.

Conjugates corresponding to this Formula VI-C can be prepared using polymeric reagents corresponding to Formula VI.

Another exemplary conjugate comprises the following structure:

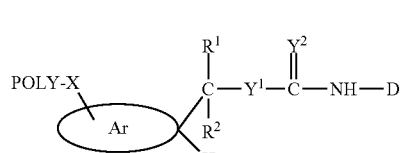

(Formula VIa-C)

wherein each of POLY, X, $R^1$, $R^2$, $Y^1$, $Y^2$ and D is as previously defined with respect to Formula VI. Conjugates corresponding to this Formula VIa-C can be prepared using polymeric reagents corresponding to Formula VIa.
Examples of conjugates of the invention include:
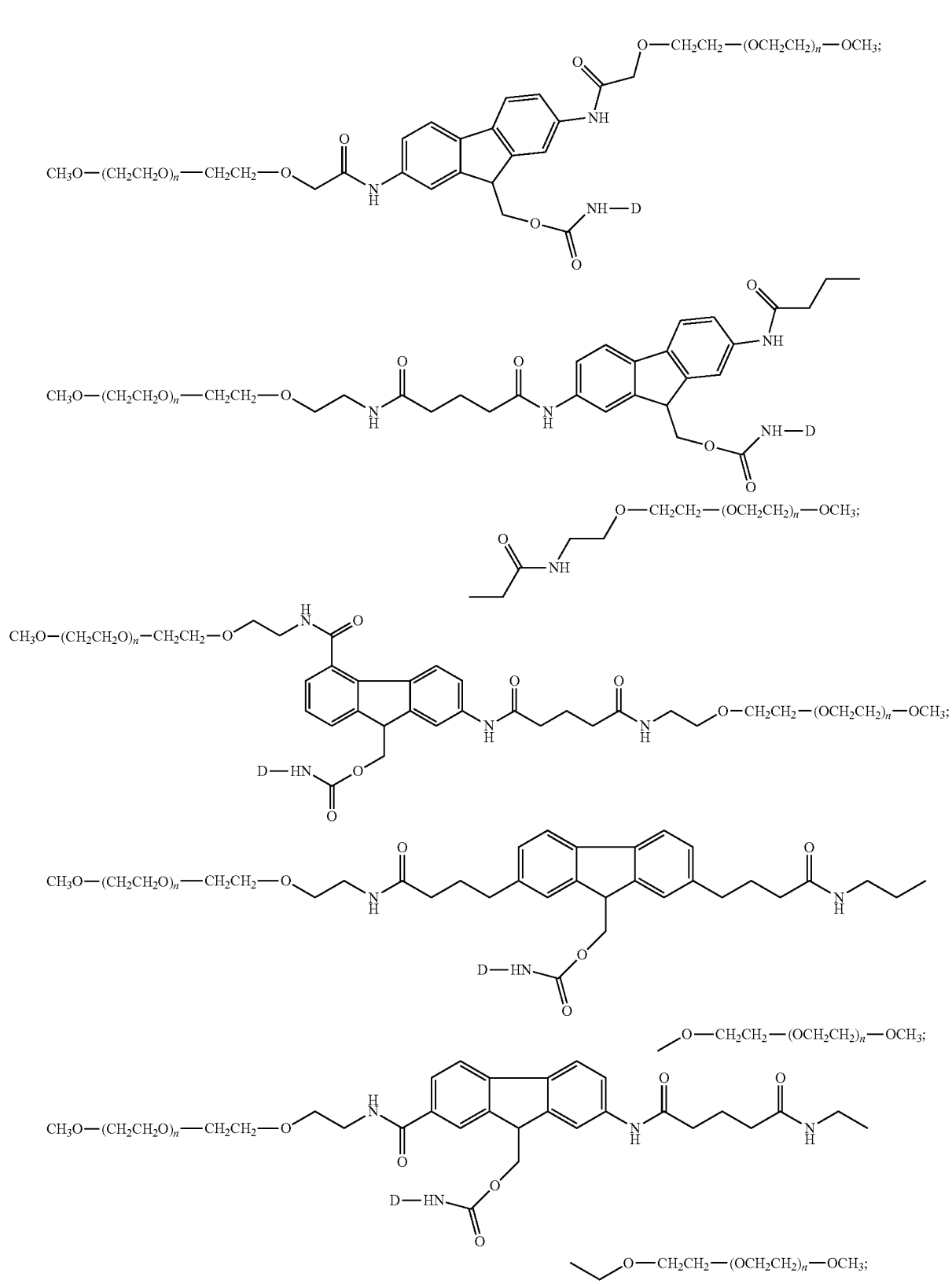

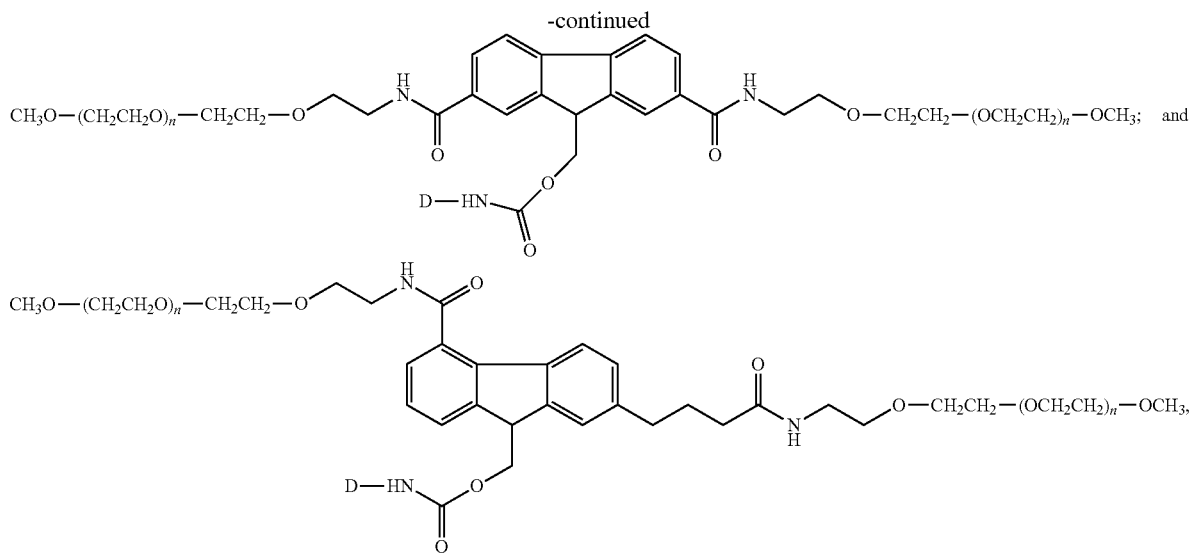

wherein each (n) is from 4 to 1500.

The biologically active agent to which a polymeric reagent as described herein can be conjugated, is an amine-containing biologically active agent. In some embodiments, the biologically active agent will be a small molecule (e.g., a biologically active agent that has a molecular weight of less than about 3,500 Daltons. In other embodiments, the biologically active agent will be a macromolecule, such as a polypeptide, having a molecular weight greater than about 3,500 Daltons. Pharmacologically active polypeptides represent a preferred type of biologically active agent. It should be understood that for purposes of the present discussion, the term "polypeptide" will be generic for oligopeptides and proteins. With regard to polypeptides, the amine to which the polymeric reagent couples to can be on the N-terminus or an amine-containing side chain of an amino acid (such as lysine) within the polypeptide.

The invention also provides for a method of preparing a conjugate comprising the step of contacting a polymeric reagent of the invention with a biologically active agent under conditions suitable to form a covalent attachment between the polymer and the biologically active agent. Typically, the polymer is added to the active agent or surface at an equimolar amount (with respect to the desired number of groups suitable for reaction with the reactive group) or at a molar excess. For example, the polymeric reagent can be added to the target active agent at a molar ratio of about 1:1 (polymeric reagent: active agent), 1.5:1, 2:1, 3:1, 4:1, 5:1, 6:1, 8:1, or 10:1. The conjugation reaction is allowed to proceed until substantially no further conjugation occurs, which can generally be determined by monitoring the progress of the reaction over time. Progress of the reaction can be monitored by withdrawing aliquots from the reaction mixture at various time points and analyzing the reaction mixture by SDS-PAGE or MALDI-TOF mass spectrometry or any other suitable analytical method. Once a plateau is reached with respect to the amount of conjugate formed or the amount of unconjugated polymer remaining, the reaction is assumed to be complete. Typically, the conjugation reaction takes anywhere from minutes to several hours (e.g., from 5 minutes to 24 hours or more). The resulting product mixture is preferably, but not necessarily purified, to separate out excess reagents, unconjugated reactants (e.g., active agent) undesired multi-conjugated species, and free or unreacted polymer. The resulting conjugates can then be further characterized using analytical methods such as MALDI, capillary electrophoresis, gel electrophoresis, and/or chromatography.

With respect to polymer-active agent conjugates, the conjugates can be purified to obtain/isolate different conjugated species. Alternatively, and more preferably for lower molecular weight (e.g., less than about 20 kiloDaltons, more preferably less than about 10 kiloDaltons) polymers, the product mixture can be purified to obtain the distribution of water-soluble polymer segments per active agent. For example, the product mixture can be purified to obtain an average of anywhere from one to five PEGs per active agent (e.g., polypeptide). The strategy for purification of the final conjugate reaction mixture will depend upon a number of factors, including, for example, the molecular weight of the polymer employed, the particular active agent, the desired dosing regimen, and the residual activity and in vivo properties of the individual conjugate(s).

If desired, conjugates having different molecular weights can be isolated using gel filtration chromatography. That is to say, gel filtration chromatography is used to fractionate differently numbered polymer-to-active agent ratios (e.g., 1-mer, 2-mer, 3-mer, and so forth, wherein "1-mer" indicates 1 polymer to active agent, "2-mer" indicates two polymers to active agent, and so on) on the basis of their differing molecular weights (where the difference corresponds essentially to the average molecular weight of the water-soluble polymer segments). For example, in an exemplary reaction where a 100 kDa protein is randomly conjugated to a polymeric reagent having a molecular weight of about 20 kDa, the resulting reaction mixture will likely contain unmodified protein (MW 100 kDa), mono-PEGylated protein (MW 120 kDa), di-PEGylated protein (MW 140 kDa), and so forth. While this approach can be used to separate PEG and other polymer conjugates having different molecular weights, this approach is generally ineffective for separating positional isomers having different polymer attachment sites within the protein. For example, gel filtration chromatography can be used to separate from each other mixtures of PEG 1-mers, 2-mers, 3-mers, and so forth, although each of the recovered PEG-mer compositions may contain PEGs attached to different reactive amino groups (e.g., lysine residues) within the active agent.

Gel filtration columns suitable for carrying out this type of separation include Superdex™ and Sephadex™ columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) optical density (OD) at 280 nm for protein content, (ii) bovine serum albumin (BSA) protein analysis, (iii) iodine testing for PEG content [Sims et al. (1980) Anal. Biochem, 107:60-63], and (iv) sodium dodecyl sulfphate polyacrylamide gel electrophoresis (SDS PAGE), followed by staining with barium iodide.

Separation of positional isomers is carried out by reverse phase chromatography using a reverse phase-high performance liquid chromatography (RP-HPLC) C18 column (Amersham Biosciences or Vydac) or by ion exchange chromatography using an ion exchange column, e.g., a Sepharose™ ion exchange column available from Amersham Biosciences. Either approach can be used to separate polymer-active agent isomers having the same molecular weight (positional isomers).

Following conjugation, and optionally additional separation steps, the conjugate mixture can be concentrated, sterile filtered, and stored at a low temperature, typically from about −20° C. to about −80° C. Alternatively, the conjugate may be lyophilized, either with or without residual buffer and stored as a lyophilized powder. In some instances, it is preferable to exchange a buffer used for conjugation, such as sodium acetate, for a volatile buffer such as ammonium carbonate or ammonium acetate, that can be readily removed during lyophilization, so that the lyophilized powder is absent residual buffer. Alternatively, a buffer exchange step may be used employing a formulation buffer, so that the lyophilized conjugate is in a form suitable for reconstitution into a formulation buffer and ultimately for administration to a mammal.

A biologically active agent for use in coupling to a polymer as presented herein may be any one or more of the following. Suitable agents can be selected from, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetic's, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

More particularly, the active agent may fall into one of a number of structural classes, including but not limited to small molecules (preferably insoluble small molecules), peptides, polypeptides, proteins, polysaccharides, steroids, nucleotides, oligonucleotides, polynucleotides, fats, electrolytes, and the like. Preferably, an active agent for coupling to a polymer as described herein possesses a native amino group, or alternatively, is modified to contain at least one reactive amino group suitable for conjugating to a polymer described herein.

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The pharmaceutical preparations encompass all types of formulations and in particular those that are suited for injection, e.g., powders that can be reconstituted as well as suspensions and solutions. The amount of the conjugate (i.e., the conjugate formed between the active agent and the polymer described herein) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients are described in "Remington: The Science & Practice of Pharmacy", 19$^{th}$ ed., Williams & Williams, (1995), the "Physician's Desk Reference", 52$^{nd}$ ed., Medical Economics, Montvale, N.J. (1998), and Kibbe, A. H., Handbook of Pharmaceutical Excipients, 3$^{rd}$ Edition, American Pharmaceutical Association, Washington, D.C., 2000.

The pharmaceutical preparations of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

As previously described, the conjugates can be administered parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The invention also provides a method for administering a conjugate as provided herein to a patient suffering from a condition that is responsive to treatment with conjugate. The method comprises administering, generally via injection, a therapeutically effective amount of the conjugate (preferably provided as part of a pharmaceutical preparation). The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

It is to be understood that while the invention has been described in conjunction with the preferred specific embodiments thereof, that the foregoing description as well as the experimental that follow are intended to illustrate and not limit the scope of the invention. Other aspects, advantages and modifications within the scope of the invention will be apparent to those skilled in the art to which the invention pertains.

All articles, books, patents, patent publications and other publications referenced herein are hereby incorporated by reference in their entireties.

EXPERIMENTAL

The practice of the invention will employ, unless otherwise indicated, conventional techniques of organic synthesis and the like, which are understood by one of ordinary skill in the art and are explained in the literature. In the following examples, efforts have been made to ensure accuracy with respect to numbers used (e.g., amounts, temperatures, and so forth), but some experimental error and deviation should be accounted for. Unless otherwise indicated, temperature is in degrees Celsius and pressure is at or near atmospheric pressure at sea level. All reagents were obtained commercially unless otherwise indicated. All generated NMR was obtained from a 300 or 400 MHz NMR spectrometer manufactured by Bruker (Billerica, Mass.). All processing is carried out in glass or glass-lined vessels and contact with metal-containing vessels or equipment is avoided.

| | |
|---|---|
| mPEG-CM | $CH_3O-(CH_2CH_2O)_n-CH_2CH_2-O-CH_2-C(O)-OH)$ |
| anh. | anhydrous |
| Fmoc | 9-fluorenylmethoxycarbonyl |
| HCl | hydrochloric acid |
| HEPES | 4-(2-hydroxyethyl)-1-piperazineethanesulfonic acid |
| NMR | Nuclear Magnetic Resonance |
| DCC | 1,3-dicyclohexylcarbodiimide |
| DMF | dimethylformamide |
| DMSO | dimethyl sulfoxide |
| MW | molecular weight |
| K or kDa | kiloDaltons |
| SEC | Size Exclusion Chromatography |
| HPLC | High Performance Liquid Chromatography |
| SDS-PAGE | Sodium Dodecyl Sulfate-Polyacrylamide Gel Electrophoresis |
| MALDI-TOF | Matrix Assisted Laser Desorption Ionization Time-of-Flight |
| TLC | Thin Layer Chromatography |
| THF | tetrahydrofuran |

Materials:

All precursor polymeric reagents referred to in these examples are commercially available unless otherwise indicated. Glucagon-like Peptide I (7-36, "GLP-1") used in these Examples was purchased from American Peptide Company (Sunnyvale, Calif.).

Example 1
Preparation of 9-hydroxymethyl-2,7-di(mPEG(20,000)-methylamide)fluorene-N-hydroxysuccinimide for Reversible PEGylation
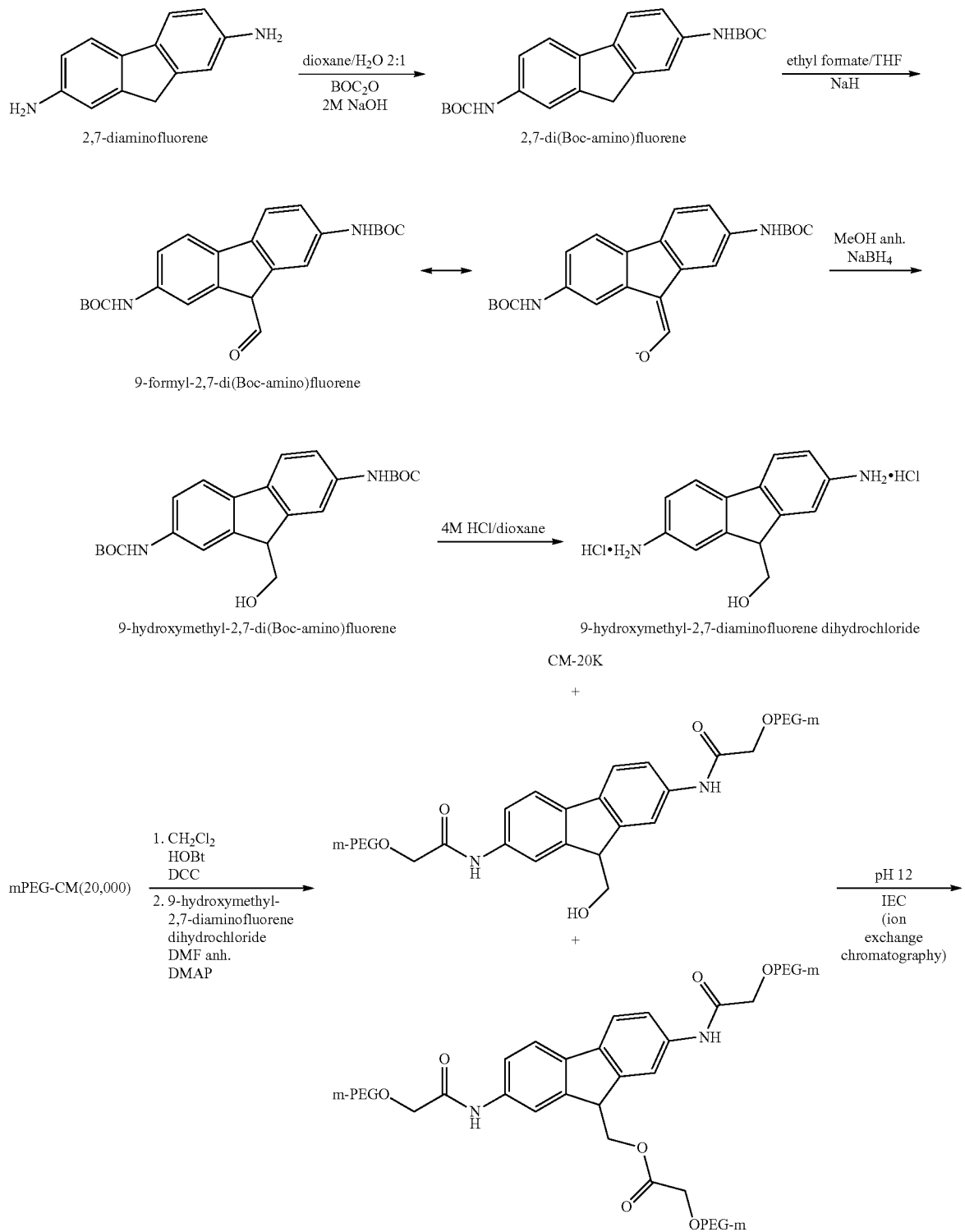
Scheme 1.

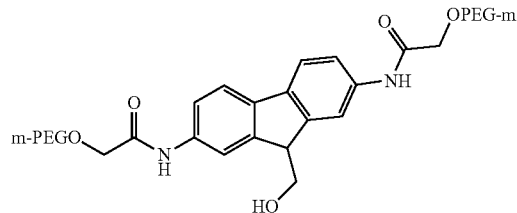 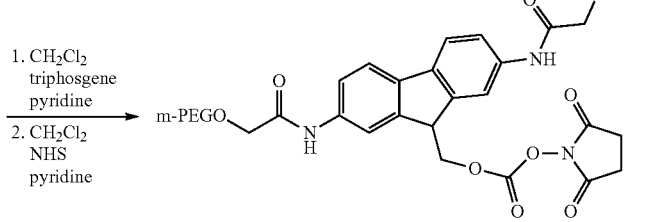

A. Preparation of 2,7-di(Boc-amino)fluorene

Under an argon atmosphere, 2,7-diaminofluorene (2.45 g, 12.5 mmol) was dissolved in 1,4-dioxane (28 mL). Deionized water (14 mL), NaOH 2M (2.2 eq, 27.5 mmol, 13.8 mL) and di-tert-butyldicarbonate ($BOC_2O$) (2.5 eq, 31.3 mmol, 6.82 g) were added successively. The reaction was stirred vigorously for 20 hours at room temperature. Product precipitated as a brown solid. The reaction was quenched by the addition of water and acidification to pH 3 with $KHSO_4$ 1M. Product was extracted with chloroform (3×400 mL) and the combined organic layers were washed with ½ saturated brine, dried over $Na_2SO_4$ and evaporated. Product was purified by flash chromatography: silica gel 60Å eluted with 1% methanol in chloroform. The purified yellow solid (5.1 g, ~99%) was pure by TLC (ninhydrin stain). $^1$H-NMR ($CDCl_3$): δ (ppm) 7.7 (bs, 2H, NH urethane); 7.6 (d, 2H, Ar); 7.2 (d, 2H, Ar); 6.5 (s, 2H, Ar); 3.8 (s, 2H, $CH_2$); 1.5 (s, 18H, Boc).

B. Preparation of 9-formyl-2,7-di(Boc-amino)fluorene

Purified 2,7-di(Boc-amino)fluorene (5 g, 12.5 mmol) (prepared from step A, above), was dissolved in ethyl formate (50 mL) and anhydrous THF (60 mL) with gentle heating. (Note: ethyl formate was stored over $K_2CO_3$ to remove formic acid.) The solution was cooled in an ice bath and sodium hydride 60% in mineral oil was added portion-wise (5.5 eq, 69 mmol, 2.75 g). The reaction was slowly warmed to room temperature and then heated to 50° C. after fitting with a reflux condenser. After two hours, the reaction was cooled in an ice bath and quenched by the slow addition of deionized water (50 mL). The aqueous layer was adjusted to pH 5 with glacial acetic acid and extracted with ethyl acetate (2×400 mL). The combined organic layers were dried with $Na_2SO_4$, filtered and evaporated under reduced pressure. The crude product (dark brown solid) was purified by flash chromatography: silica gel 60 Å step-wise gradient elution 1-5% methanol in chloroform. Yield (4.8 g, ~90%) of a yellow to brown solid, depending on purity. $^1$H-NMR ($d_6$-DMSO): δ (ppm) 11.0 (s, 0.9H, enol); 9.3 (2 s, 1.9H, NH urethane); 7.2-8.3 (m, Ar, $C^{10}$ H enol); 6.5 (2 s, 0.1H, NH urethane); 4.1 (m, 0.3H, CH); 1.5 (s, 18H, Boc).

C. Preparation of 9-hydroxymethyl-2,7-di(Boc-amino)fluorene

9-Formyl-2,7-di(Boc-amino)fluorene (0.47 g, 1.1 mmol) was dissolved in anhydrous methanol (MeOH) (5 mL) under an argon atmosphere. $NaBH_4$ (1.2 eq, 1.3 mmol, 0.05 g) was added and the reaction was stirred at room temperature for five hours. The reaction was diluted with deionized water and acidified to pH 5 with glacial acetic acid. The reaction was extracted with ethyl acetate (2×100 mL) and the organic layers were washed with saturated $NaHCO_3$ (4×20 mL) and brine (3×20 mL). The organic layers were dried over $MgSO_4$, filtered and evaporated. The crude product, orange solid, was purified by flash chromatography: silica gel 60 Å gradient elution 1-5% methanol in chloroform (alternative gradient elution with 15-20% ethyl acetate in dichloromethane, "DCM"). Product was a yellow solid (0.39, 83%). $^1$H-NMR ($CD_3OD$): δ (ppm) 7.9 (s, 0.5H, NH urethane); 7.7 (s, 2H, Ar); 7.6 (d, 2H, Ar); 7.4 (d, 2H, Ar); 4.0 (m, 1H, CH); 3.9 (m, 2H, $CH_2$); 1.6 (s, 18H, Boc).

D. Preparation of 9-hydroxymethyl-2,7-diaminofluorene dihydrochloride

9-Hydroxymethyl-2,7-di(Boc-amino)fluorene (0.39 g, 0.9 mmol) was dissolved in 1,4-dioxane. At 0° C. concentrated HCl (2.5 mL) was added and the reaction was stirred for two hours at 0° C. and for one hour at room temperature. The reaction solvents were removed at reduced pressure (45° C.). The product was dissolved in methanol and evaporated (2 times). The product was dissolved in methanol (8 mL) and precipitated by the slow addition of diethyl ether and cooling (repeat). The product was a red-orange solid (0.25 g, 91%) that showed a single spot by TLC (chloroform/methanol/acetic acid 85:15:3, ninhydrin stain). $^1$H-NMR ($CD_3OD$): δ (ppm) 8.1 (d, 2H, Ar); 7.8 (s, 2H, Ar); 7.5 (d, 2H, Ar); 4.3 (t, 1H, CH); 4.0 (d, 2H, $CH_2$)

E. Preparation of 9-hydroxymethyl-2,7-di(mPEG(20,000)-methylamide)fluorene mPEG-CM(20,000) (mPEG-CM having MW=19,458; 20 g, 1.03 mmol, 3.5 eq), in anhydrous toluene (80 mL) was azeotropically distilled under reduced pressure at 60° C. on a rotary evaporator. The solids were dissolved in anhydrous dichloromethane (40 mL) under an argon atmosphere followed by addition of N-hydroxybenzotriazole (HOBt) anhydrous (3.5 eq, 1.03 mmol, 139 mg) and 1,3-dicyclohexylcarbodiimide (DCC) (3.7 eq, 1.09 mmol, 224 mg). In a separate flask, 9-hydroxymethyl-2,7-diaminofluorene dihydrochloride (1 eq, 0.294 mmol, 88 mg) and 4-dimethylaminopyridine (2.2 eq, 0.65 mmol, 79 mg) were dissolved in anhydrous DMF (2.5 mL). After stirring the DCC reaction for several minutes (5-15 minutes), the DMF solution of 9-hydroxymethyl-2,7-diaminofluorene was quantitatively transferred to the DCC reaction. The reaction was stirred at room temperature for 27 hours before solvent was evaporated at reduced pressure. The thick syrup was dissolved in dry isopropyl alcohol ("IPA," 400 mL, slow addition) with gentle heating. The PEG product precipitated on standing at room temperature. Additional IPA (100 mL) was added while stirring at 0° C. for 30 minutes. The precipitate was filtered and washed with cold IPA/diethyl ether 7:3 (80 mL) and diethyl ether. The crude product (pale yellow powder, 9-(mPEG(20,000)methylester)-methyl-2,7-di(mPEG(20,000)-methylamide)fluorene) was dried under hi-vacuum (yield 18.3 g).

Under an argon atmosphere, the crude product (18.3 g) was dissolved in deionized water and adjusted to pH 12±0.1 with NaOH 1 M. The hydrolysis reaction mixture was stirred at room temperature for three hours. The pH was adjusted to 3.0 with 10% phosphoric acid. (The aqueous solution was filtered through a bed of celite and rinsed with water.) NaCl (60 g) was dissolved into the aqueous solution and then extracted with DCM (2×150 mL). The combined organic layers were dried over $MgSO_4$, filtered and evaporated at reduced pressure. The crude product was dissolved in deionized water and desalted with ion exchange resin. Ion exchange chromatography of the PEG solution was preformed on DEAE sepharose (0.9 L) eluting with water. Fractions containing PEG were collected. The purified product (pale yellow powder) was absent of mPEG-CM(20,000) (HPLC analysis). Yield 7.3 g, 64% (representing the total amount of PEG material recovered), substitution 75% or better (representing the percentage of PEG, of the amount recovered, having the desired functionality). $^1$H-NMR ($CD_2Cl_2$): δ (ppm) 8.9 (s, 2H, NH amide); 7.9 (s, 2H, Ar); 7.7 (m, 4H, Ar); 4.1 (m, 5H, $CH_2C$=O, CH); 4.0 (d, 2H, $CH_2$); 3.6 (s, PEG backbone); 3.3 (s, 3H, —OCH3).

F. Preparation of 9-hydroxymethyl-2,7-di(mPEG(20,000)-methylamide)fluorene-N-hydroxysuccinimide 9-Hydroxymethyl-2,7-di(mPEG(20,000)-methylamide) fluorene (0.5 g, 0.013 mmol) in anhydrous acetonitrile (10 mL) was azeotropically distilled under reduced pressure at 50° C. on a rotary evaporator. The solid was dissolved in anhydrous DCM (2 mL, "$CH_2Cl_2$") followed by addition of triphosgene. (Care was used to trap excess phosgene gas from reaction with base trap) (1.4 eq, 0.018 mmol, 5 mg). After several minutes, anhydrous pyridine (2 eq, 0.026 mmol, 2 μL of pyridine in DCM [2 μL pyridine/50 μL DCM]) was added. At one and one-half hours most of the reaction solvent and excess phosgene (use base trap on vent) was evaporated with gentle warming (40° C.). The syrup was dissolved in anhydrous DCM (2 mL) followed by addition of N-hydroxysuccinimide (5.3 eq, 0.068 mmol, 8 mg, "NHS") and anhydrous pyridine (3.2 eq, 0.041 mmol, 83 μL of the above (2:50) solution in DCM). After four hours, the solvent was evaporated under an argon stream. The syrup was dissolved in anhydrous IPA and precipitated at room temperature. The precipitate was filtered and washed with cold IPA and diethyl ether. Residual solvents were evaporated under vacuum to give a very pale yellow powder. Yield 0.4 g, 80%, substitution 73% NHS carbonate by HPLC. $^1$H-NMR ($CD_2Cl_2$): δ (ppm) 8.9 (s, 2H, NH amide); 7.9 (s, 2H, Ar); 7.7 (m, 4H, Ar); 4.7 (d, 2H, $CH_2$); 4.3 (t, 1H, CH); 4.1 (s, 4H, $CH_2C$=O); 2.8 (s, 4H, $CH_2CH_2$ NHS).

Using this same procedure, polymeric reagents having other molecular weights can be prepared by substituting an mPEG-CM polymeric reagent having a molecular weight other than 20,000.

Example 2

PEGylation of Insulin with FMOC PEG2 40K Carbamate

A. PEGylation

The polymeric reagent prepared in Example 1, 9-hydroxy-2,7-di(mPEG(20,000)-methylamide)fluorene-N-hydroxysuccinimide, was stored at −20° C. and warmed to room temperature in a dessicator. Insulin (8.9 mg) was weighed out and dissolved in 1 mL DMSO. A molar ratio of 3:1 (PEG: insulin) was used. 184.6 mg of 9-hydroxy-2,7-di(mPEG(20,000)-methylamide)fluorene-N-hydroxysuccinimide was weighed and dissolved in 1 mL acetonitrile and then added to insulin. The reaction was stirred under nitrogen for one hour, and then quenched by diluting it 1:5 with 20 mM acetic acid, pH 3.0 to drop the reaction mixture pH to pH 3.1. The low pH stabilizes the degradable conjugate.

B. Purification

Cation exchange was used to purify the 1-mer PEG-insulin conjugate, which is the conjugate having PEGylation at one insulin site, from the 2-mer, which is the conjugate having PEGylation at two insulin sites. A 20 mL SP650 column and an ÄKTA Basic System (Amersham Biosciences, Piscataway N.J.) were used to purify the PEG conjugates. The starting buffer was 20 mM HAc/NaAc (acetic acid/sodium acetate), pH 3.1 and the elution buffer was 20 mM HAc/NaAc, 1 M NaCl, pH 3.1. The flow rate was 10 mL/min, and the sample loading was 9 mg, insulin content. The purification method is listed in Table 1.

TABLE 1

Purification Method for Degradable PEG Insulin Conjugate

| Volume (ml) | PrimeMethod 109 % B |
|---|---|
| 0 | 0 |
| 60 | 0 |
| 220 | 40 |
| 240 | 100 |
| 300 | 100 |
| 301 | 0 |
| 361 | 0 |

C. Characterization and Quantification of Purified Conjugates

Figure 2:
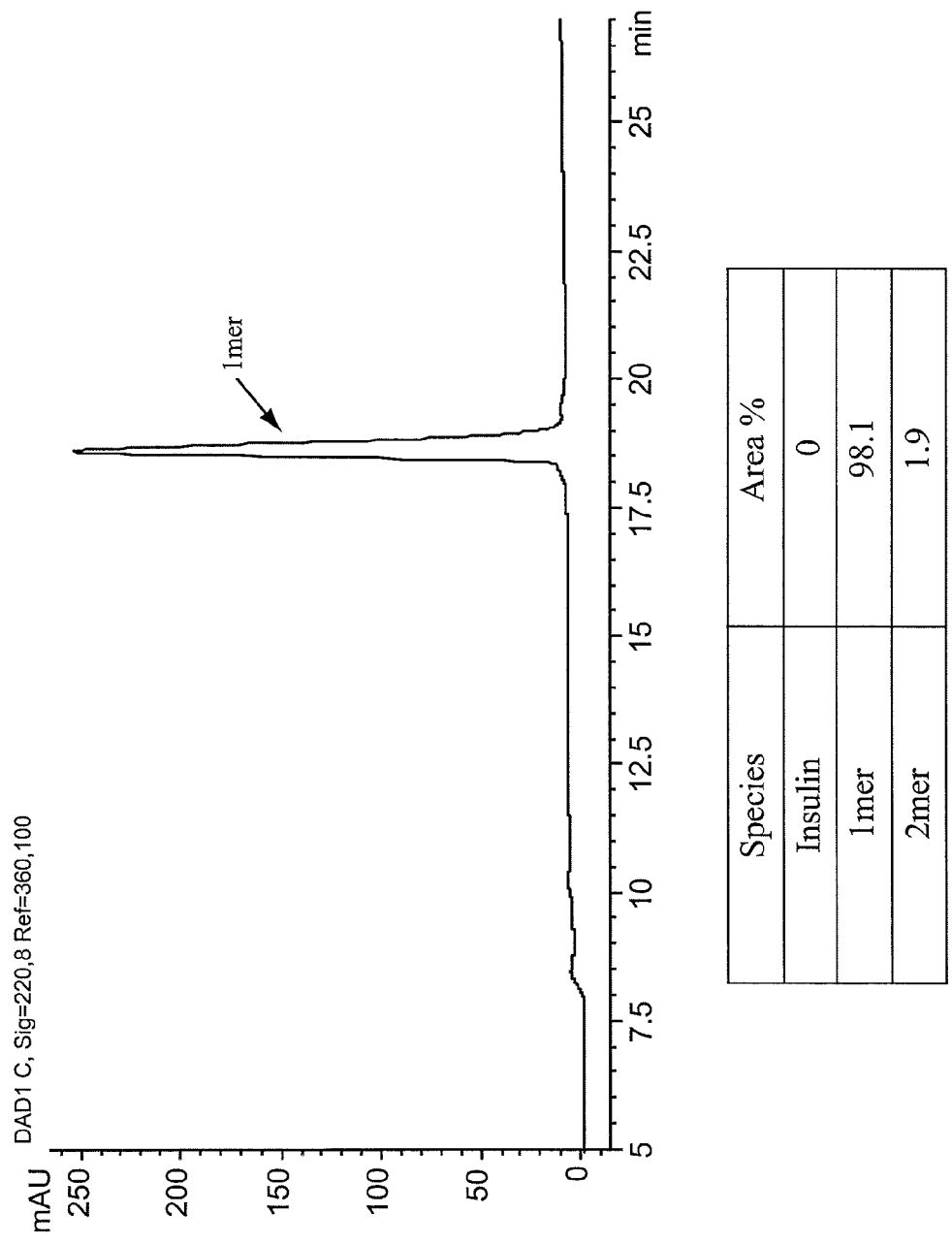
FIG. 2 is an HPLC chromatogram of the PEGylated 1-mer conjugate prepared as described in Example 2.

HPLC analysis of the reaction mixture is shown in FIG. 1. FIG. 2 shows the HPLC analysis of the PEGylated 1-mer conjugate (or monoPEGylated conjugate). The purity of the PEGylated 1-mer conjugate is 98.1% with 1.9% 2-mer.

D. Degradation Study of Purified Conjugate

Figure 3:
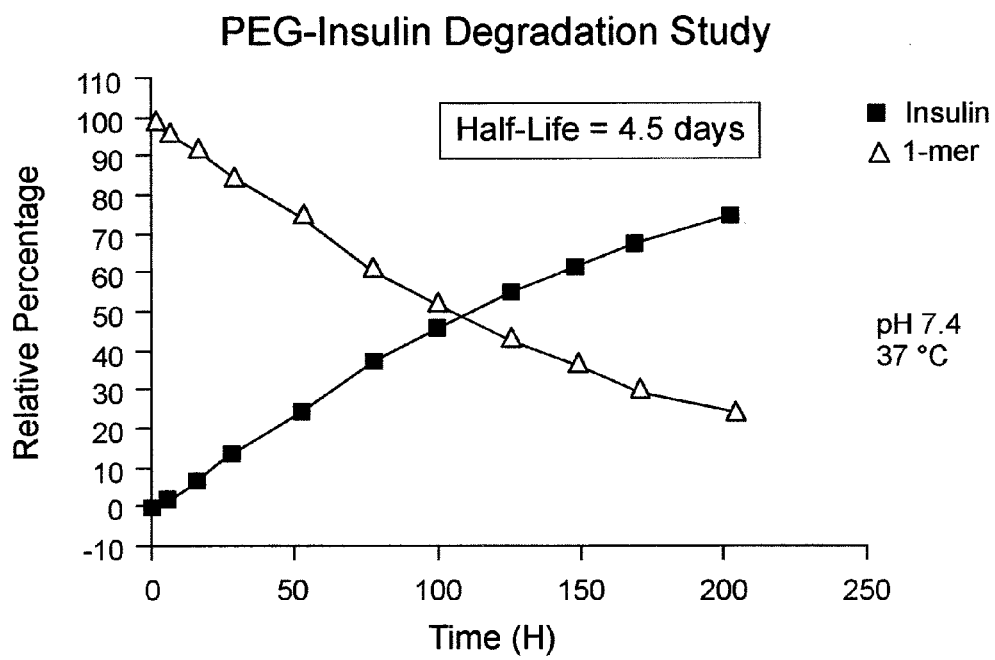
FIG. 3 is a graph showing the results of a degradation study of a degradable PEG-insulin 1-mer conjugate (performed at pH 7.35 and 37° C.) as described in Example 2.

An in vitro release study was performed on the purified conjugate. The test was performed on an Agilent 1100 with a thermostatted autosampler (Agilent Technologies, Inc., Palo Alto, Calif.). An HPLC method was used to analyze the release of the native protein and the reduction of the conjugate. The 1-mer conjugate (or monoPEGylated conjugate) was diluted 10:1 into 10×PBS (phosphate buffered saline) buffer, pH 7.35. It was incubated at 37° C., and aliquots were removed for time points. Time 0 was assumed to be before the dilution with PBS, so the HPLC results from the 1-mer conjugate were used. The time points were taken at 5 hours, 15 hours, and 28 hours, and then once a day for 8 days. The compiled results are shown in FIG. 3.

The relative percentage of each component in the sample at each time point was plotted using Prism analysis software (GraphPad Software, Inc., San Diego Calif.). The data was fitted to a nonlinear equation, and this equation was used to estimate the half-life of 4.5 days for the 1-mer conjugate in buffer.

Example 3

Preparation of 9-hydroxymethyl-2,7-di(mPEG(10,000)-amidoglutaric amide)fluorene-N-hydroxysuccinimide(or "G2PEG2Fmoc$_{20k}$-NHS")

The synthesis of 9-hydroxymethyl-2,7-di(mPEG(10,000)-amidoglutaric amide)fluorene-N-hydroxysuccinimide is represented schematically in Scheme 2, below.

Scheme 2.
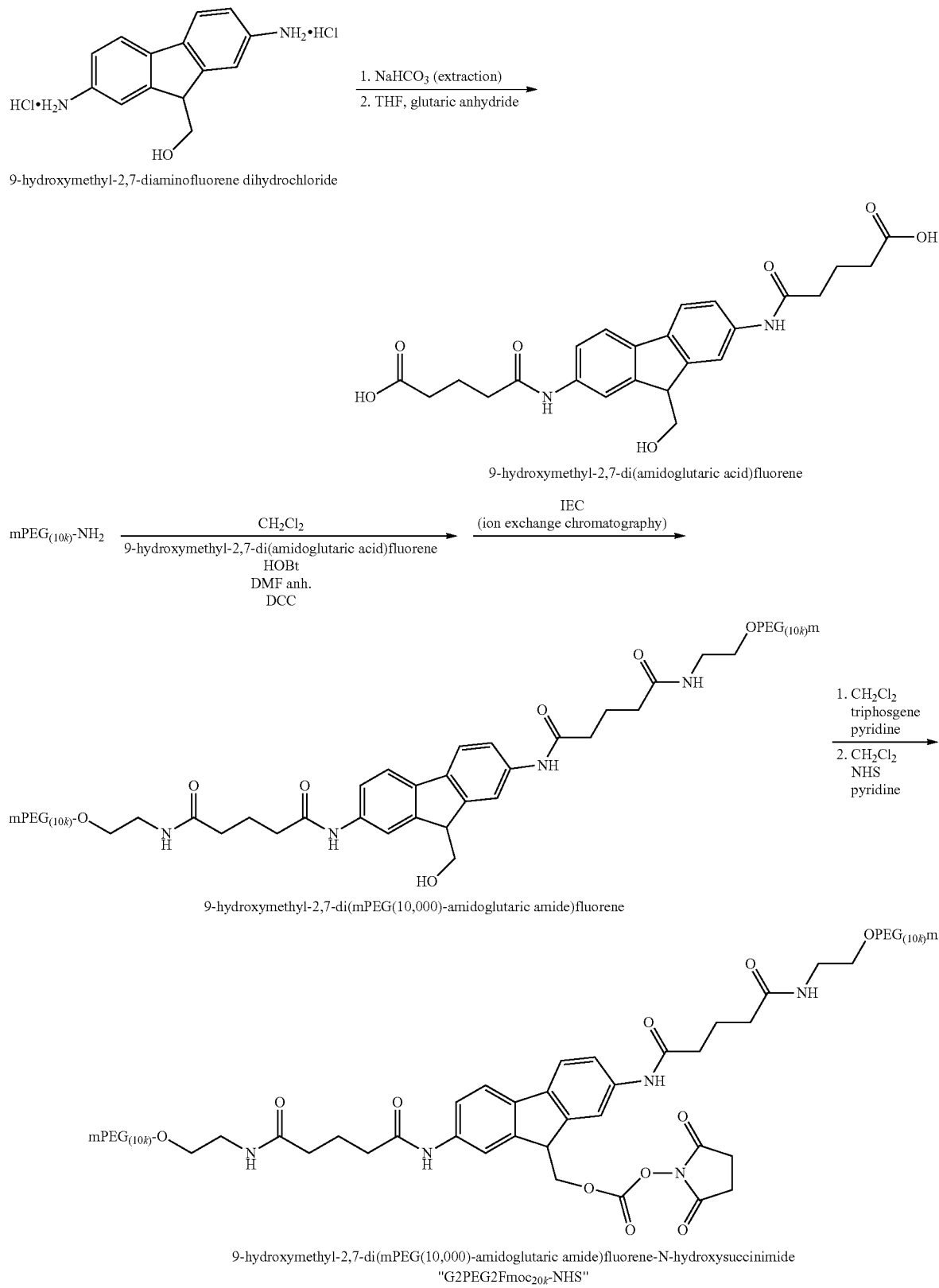

A. Preparation of 9-Hydroxymethyl-2,7-di(amidoglutaric acid)fluorene

Under an argon atmosphere, 9-hydroxymethyl-2,7-diaminofluorene dihydrochloride (preparation described in steps A through D in Example 1) was dissolved in deionized water and adjusted to pH 8 with saturated NaHCO$_3$. The mixture was diluted in half with brine and the precipitate was extracted with ethyl acetate. The ethyl acetate layers were dried over Na$_2$SO$_4$, filtered and evaporated for 9-hydroxymethyl-2,7-diaminofluorene (brown powder, 84% isolated yield).

9-Hydroxymethyl-2,7-diaminofluorene (0.38 g, 1.7 mmol) was dissolved in anhydrous tetrahydrofuran ("THF," 10 mL) and glutaric anhydride (97%, 2.2 eq, 3.7 mmol, 0.435 g) was added. The reaction was stirred for 4.5 hours and absence of amine was confirmed by TLC (ninhydrin stain, 90:10:3 ethyl acetate/methanol/acetic acid). The reaction mixture was diluted with hexanes (10 mL), filtered and washed with 1:1 THF/hexanes then hexanes. The crude product was dissolved in a minimal amount of methanol (1 mL) and THF (10 mL) and precipitated with addition of hexanes (10 mL). The mixture was cooled (4° C.), filtered and washed with 1:1 THF/hexanes then hexanes. Yield was 0.59 g (77%) of yellow-orange powder.

$^1$H-NMR (CD$_3$OD): δ (ppm) 7.9 (s, 2H, Ar); 7.7 (d, 2H, Ar); 7.5 (dd, 2H, Ar); 4.0 (t, 1H, CH); 3.9 (d, 2H, CH$_2$); 2.5 (t, 4H, CH$_2$); 2.4 (t, 4H, CH$_2$); 2.0 (m, 4H, CH$_2$).

B. Preparation of 9-hydroxymethyl-2,7-di(mPEG(10,000)-amidoglutaric amide)fluorene mPEG-NH$_2$(10,000) (M$_n$=10,200; chromatographically purified, 12.75 g, 1.25 mmol) in anhydrous toluene (100 mL) was azeotropically distilled under reduced pressure at 50° C. on a rotary evaporator. The solids were dissolved in anhydrous DCM (50 mL) under an argon atmosphere. A solution of 9-hydroxymethyl-2,7-di(amidoglutaric acid)fluorene (1 eq., 0.5 mmol, 0.225 g) and N-hydroxybenzotriazole (HOBt) anhydrous (2.2 eq, 1.1 mmol, 149 mg) in anhydrous DMF (5 mL) was quantitatively added to the PEG solution (2.5 mL DMF to rinse). 1,3-Dicyclohexylcarbodiimide (DCC) (2.4 eq, 1.2 mmol, 248 mg) was then added to the reaction solution. The reaction was stirred at room temperature for 24 hours before solvent was evaporated at reduced pressure. The thick syrup was dissolved in dry IPA (500 mL, slow addition) with gentle heating. The PEG product precipitated on standing at room temperature. The precipitate was cooled to 10° C. for ten minutes, filtered and washed with cold IPA (200 mL) and then diethyl ether (200 mL). The crude product (off-white powder) was dried under hi-vacuum and then dissolved in deionized water. Ion exchange chromatography of the PEG solution was preformed on POROS media (0.1 L, Boehringer-Mannheim, GmbH, Mannheim Germany) eluting with water. Fractions containing neutral PEG were collected. The purified product contained no mPEG-NH$_2$(10,000) (HPLC analysis). Yield 5.5 g, 53%, substitution 85% or better. $^1$H-NMR (CD$_2$Cl$_2$): δ (ppm) 8.6 (s, 2H, ArNH amide); 7.9 (s, 2H, Ar); 7.6 (m, 4H, Ar); 6.4 (bs, 2H, NH amide); 4.1 (m, 1H, CH); 4.0 (d, 2H, CH$_2$); 3.6 (s, PEG backbone); 3.3 (s, 3H, —OCH$_3$); 2.4 (t, 4H, CH$_2$); 2.3 (t, 4H, CH$_2$); 2.0 (m, 4H, CH$_2$).

C. Preparation of 9-Hydroxymethyl-2,7-di(mPEG(10,000)-amidoglutaric amide)-N-hydroxysuccinimide 9-Hydroxymethyl-2,7-di(mPEG(10,000)-amidoglutaric amide)fluorene (5.3 g, 0.25 mmol) in anhydrous acetonitrile (100 mL) was azeotropically distilled under reduced pressure at 50° C. on a rotary evaporator. The solid was dissolved in anhydrous DCM (27 mL) followed by addition of triphosgene (1.4 eq, 0.36 mmol, 106 mg). (Care was used to trap excess phosgene gas from reaction with base trap.). After several minutes, anhydrous pyridine (2 eq, 0.51 mmol, 41 μL) was added. After one and one-half hours, most of the reaction solvent and excess phosgene (use base trap on vent) was evaporated with gentle warming (40° C.). The syrup was dissolved in anhydrous DCM (15 mL) followed by addition of N-hydroxysuccinimide (5.3 eq, 1.35 mmol, 155 mg, "NHS"). After 15 minutes anhydrous pyridine (3.2 eq, 0.81 mmol, 66 μL) was added. The reaction was stirred for two hours and the solvent was evaporated under reduced pressure. The syrup was dissolved in anhydrous IPA (200 mL) and precipitated at room temperature. The precipitate was filtered and washed with cold IPA and diethyl ether (150 mL containing 10 mg BHT). Residual solvents were evaporated under vacuum to provide an off-white powder. Yield 5.1 g, 95%, substitution ~70% NHS carbonate by HPLC.

Another polymeric reagent was prepared using this same approach except mPEG-NH$_2$ (chromatographically purified) having a weight average molecular weight of about 20,000 was substituted for mPEG-NH$_2$(10,000). The resulting polymeric reagent had a total molecular weight of about 40,000 Daltons. The name of polymeric reagent so prepared is 9-hydroxymethyl-2,7-di(mPEG(20,000)-amidoglutaric amide)fluorene-N-hydroxysuccinimide (or "G2PEG2Fmoc$_{40k}$-NHS").

Another polymeric reagent was prepared using this same approach except mPEG-NH$_2$ (prepared in high purity using conventional methods) having a weight average molecular weight of about 30,000 was substituted for mPEG-NH$_2$(10,000). The resulting polymeric reagent had a total molecular weight of about 60,000 Daltons. The name of polymeric reagent so prepared is 9-hydroxymethyl-2,7-di(mPEG(30,000)-amidoglutaric amide)fluorene-N-hydroxysuccinimide (or "G2PEG2Fmoc$_{60k}$-NHS").

Example 4

Preparation of 9-hydroxymethyl-4-(mPEG(10,000)-carboxyamide)-7-(mPEG(10,000)amidoglutaric amide)fluorene-N-hydroxysuccinimide The synthesis of 9-hydroxymethyl-4-(mPEG(10,000)-carboxyamide)-7-(mPEG(10,000)-amidoglutaric amide)fluorene-N-hydroxysuccinimide is represented schematically in Scheme 4, below.

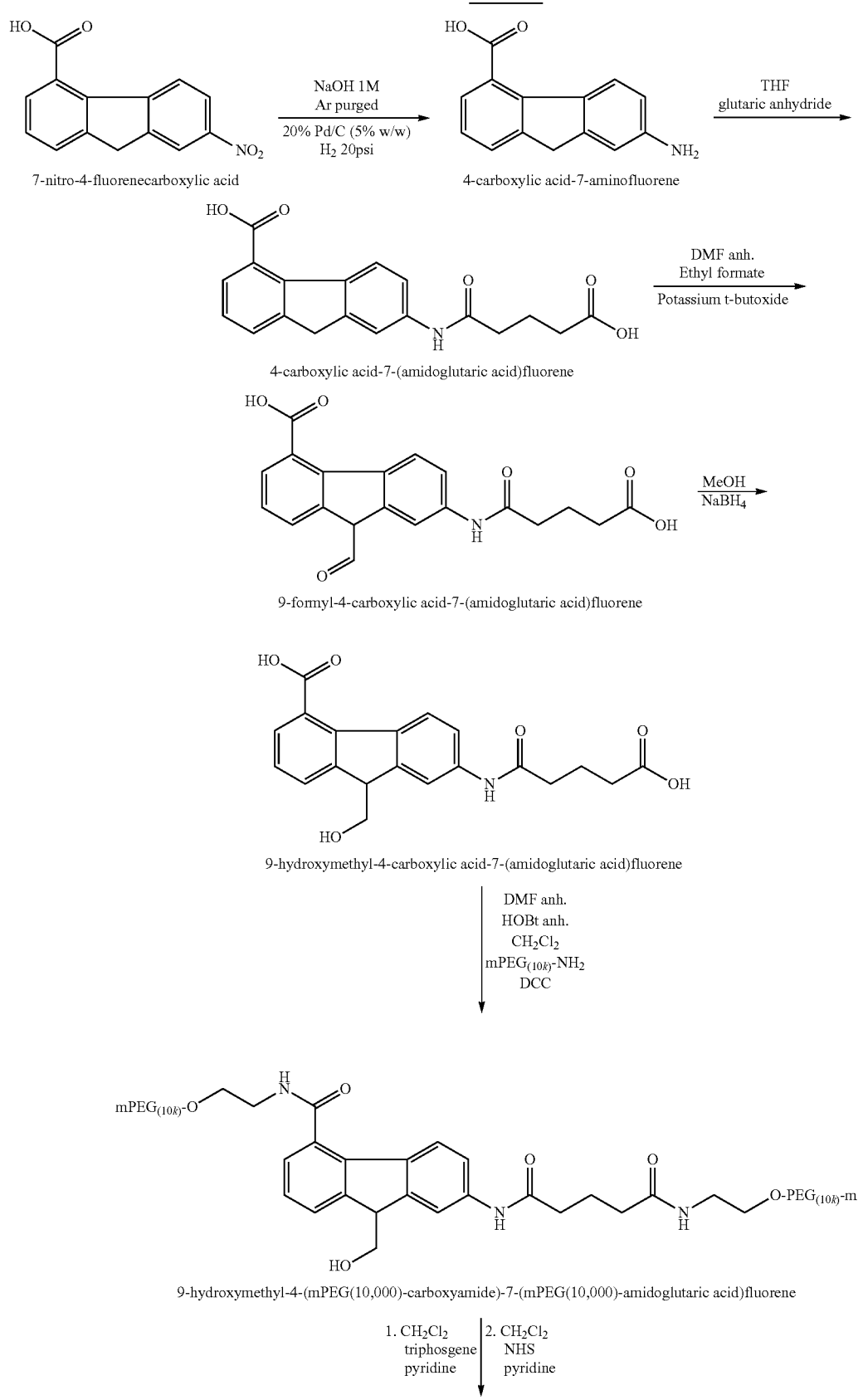

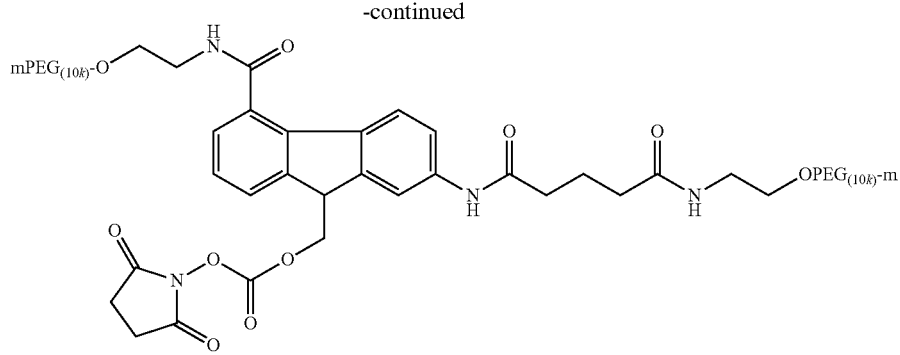

9-hydroxymethyl-4-(mPEG(10,000)-carboxyamide)-7-(mPEG(10,000)-amidoglutaric acid)fluorene-N-hydroxysuccinimide

A. Preparation of 4-carboxylic acid-7-aminofluorene

In a Parr hydrogenation bottle (Parr Instrument Company, Moline Ill.) was dissolved 7-nitro-4-fluorenecarboxylic acid (8.0 g, 0.031 mol) [prepared from diphenic acid as described in Helvetica Chimica Acta (1984) 67, 2009-2016, and also available commercially from Sigma-Aldrich, St. Louis, Mo.] in argon (Ar) purged 1M NaOH (250 mL, slightly warmed if needed). After careful addition of 20% Pd/C (wet with 50% water) 5% by weight (400 mg), the Parr bottle was evacuated/filled 3 times on a Parr apparatus to ensure hydrogen atmosphere. The suspension was shaken under 20 psi hydrogen gas for 18 hours and then the remaining hydrogen was removed at reduced pressure. The suspension was filtered over a bed of celite, rinsed with additional water and then adjusted to pH 4 with acetic acid. The product was extracted with brine and ethyl acetate (3×800 mL). Each organic layer was washed with a small amount of brine. The combined organic layers were dried over $Na_2SO_4$, filtered and evaporated to dryness. Toluene was added and evaporated at reduced pressure to aid in removal of acetic acid (repeated 2-3 times if necessary). Final evaporation was under hi-vacuum for one or more days. Yield was 6.1 g (86%) $^1$H-NMR ($d_6$-DMSO): δ (ppm) 8.1 (d, 1 H, Ar); 7.62 (d, 1 H, Ar); 7.58 (d, 1 H, Ar); 7.2 (t, 1 H, Ar); 6.8 (s, 1 H, Ar); 6.5 (d, 1 H, Ar); 3.8 (s, 2 H, $CH_2$); 1.9 (s, <0.25 H, HOAc).

B. Preparation of 4-carboxylic acid-7-(amidoglutaric acid)fluorene

4-Carboxylic acid-7-aminofluorene (8.6 g, 0.038 mol) was dissolved in anhydrous THF (150 mL) and glutaric anhydride (97%, 4.94 g, 0.042 mol) was added. The reaction was stirred for 4.5 hours and absence of amine was confirmed by TLC (ninhydrin stain, 90:10:3 ethyl acetate/methanol/acetic acid, or similar). The reaction mixture was diluted with hexanes (150 mL), cooled, filtered and washed with 1:1 cold THF/hexanes then hexanes. Residual solvents were evaporated at reduced pressure. Yield was 7.2 g (55%). $^1$H-NMR ($CD_3OD$): δ (ppm) 8.4 (d, 1 H, Ar); 8.0 (s, 1 H, Ar); 7.8 (d, 1 H, Ar); 7.7 (d, 1 H, Ar); 7.5 (d, 1 H, Ar); 7.4 (t, 1 H, Ar); 4.0 (s, 2 H, $CH_2$); 2.5 (t, 2 H, $CH_2$); 2.4 (t, 2 H, $CH_2$); 2.0 (m, 2 H, $CH_2$).

C. Preparation of 9-formyl-4-carboxylic acid-7-(amidoglutaric acid)fluorene

The diacid, 4-carboxylic acid-7-(amidoglutaric acid)fluorene (7.16 g, 0.021 mol), was dissolved in anhydrous DMF (200 mL) and ethyl formate (stored over $K_2CO_3$, 350 mL). Potassium tert-butoxide (95%, 19.9 g, 0.169 mol) was carefully added in several portions. The reaction was gently refluxed at 45° C. for 30 minutes and then stirred at room temperature for 2.5 hours. The solution was cooled in an ice bath then 1M HCl (500 mL) and brine (350 mL) were added. The product was extracted with ethyl acetate (3×700 mL). The organic layers were washed with brine and then dried over $Na_2SO_4$. The desiccant was filtered and the solvent was evaporated at reduced pressure. Yield was >7.8 g (100%) and contained residual DMF. $^1$H-NMR ($d_6$-DMSO): δ (ppm) 11.5 (d, 0.5 H, formyl); 11.4 (d, 0.5 H, formyl); 10.0 (d, 1 H, NH); 8.4-7.3 (m, 7 H, Ar); 2.4 (t, 2 H, $CH_2$); 2.3 (t, 2 H, $CH_2$); 1.8 (m, 2 H, $CH_2$).

D. Preparation of 9-hydroxymethyl-4-carboxylic acid-7-(amidoglutaric acid) fluorene The 9-formyl-4-carboxylic acid-7-(amidoglutaric acid) fluorene (7.8 g, 0.021 mol) was dissolved in anhydrous methanol (MeOH) (150 mL). With the flask in a room temperature bath, sodium borohydride (6.0 g, 0.159 mol) was carefully added in several portions. At two hours and four hours, additional portions of sodium borohydride (2.0 g, 0.053 mol) were carefully added. After seven hours, the solvent was evaporated at reduced pressure, the residue was dissolved in water and then acidified with 1M HCl. The yellow precipitate was extracted with brine and ethyl acetate (4×700 mL). Each ethyl acetate layer was washed with brine (2×), combined and dried over $Na_2SO_4$. The solvent was evaporated and the crude product was recrystallized from methanol/chloroform. Yield 4.9 g (63%) yellow crystals. $^1$H-NMR ($CD_3OD$): δ (ppm) 8.4 (d, 1 H, Ar); 8.0 (s, 1 H, Ar); 7.85 (d, 1 H, Ar); 7.83 (d, 1 H, Ar); 7.5 (dd, 1 H, Ar); 7.4 (t, 1 H, Ar); 4.1-3.9 (m, 2 H, $CH_2$, CH); 2.5 (t, 2 H, $CH_2$); 2.4 (t, 2 H, $CH_2$); 2.0 (m, 2 H, $CH_2$).

E. Preparation of 9-hydroxymethyl-4-(mPEG(10,000)-carboxyamide)-7-(mPEG(10,000) amidoglutaric amide)fluorene mPEG-$NH_2$(10,000) ($M_d$=9,418; chromatographically purified, 75 g, 0.008 mol, also designated as "mPEG$_{(10k)}$-$NH_2$") in anhydrous toluene (750 mL) was azeotropically distilled under reduced pressure at 50° C. on a rotary evaporator. The solids were dissolved in anhydrous DCM ($CH_2Cl_2$) (300 mL) under an argon atmosphere. A solution of 9-hydroxymethyl-4-carboxylic acid-7-(amidoglutaric acid)fluorene (1.3 g, 0.0036 mol) and N-hydroxybenzotriazole (HOBt) anhydrous (1.0 g, 0.0076 mol) in anhydrous DMF (33 mL) was quantitatively added to the PEG solution (20 mL DMF to rinse). 1,3-Dicyclohexylcarbodiimide (DCC) (1.65 g, 0.008 mol) was then added to the reaction solution. The reaction was stirred at room temperature for 16 hours before solvent was evaporated at reduced pressure. The thick syrup was dissolved in dry IPA (3.6 L, slow addition) with gentle heating. The PEG product precipitated on standing at room temperature. The precipitate was cooled to 10° C. for ten minutes, filtered and washed with cold IPA (400 mL) and then diethyl ether (400 mL). The crude product (off-white powder) was dried under hi-vacuum and then dissolved in deionized water. Ion exchange chromatography of the PEG solution was preformed on POROS media (1 L) eluting with water. Fractions containing neutral PEG were collected and further purified with DEAE Sepharose media (0.5 L). The purified product was not found to contain mPEG-$NH_2$ (10,000) or monoPEG acid products (HPLC analysis). Yield 55 g, 79% (substitution 95%). $^1$H-NMR ($CD_2Cl_2$): δ (ppm) 8.7 (s, 1 H, ArNH amide); 8.0 (s, 1 H, Ar); 7.9 (d, 1 H, Ar); 7.7 (d, 1 H, Ar); 7.5 (d, 1 H, Ar); 7.4 (d, 1 H, Ar); 7.3 (t, 1 H, Ar); 6.7 (bs, 1 H, NH amide); 6.4 (bs, 1 H, NH amide); 4.0 (m, 3 H, CH, $CH_2$); 3.6 (s, PEG backbone); 3.3 (s, 6 H, —$OCH_3$); 2.4 (t, 2 H, $CH_2$); 2.3 (t, 2 H, $CH_2$); 2.0 (m, 2 H, $CH_2$).

F. Preparation of 9-hydroxymethyl-4-(mPEG(10,000)-carboxyamide)-7-(mPEG(10,000) amidoglutaric amide)fluorene-N-hydroxysuccinimide The 9-hydroxymethyl-4-(mPEG(10,000)-carboxyamide)-7-(mPEG(10,000) amidoglutaric amide)fluorene (14 g, 0.00072 mol) in anhydrous toluene (140 mL) was azeotropically distilled under reduced pressure at 45° C. on a rotary evaporator. The solid was dissolved in anhydrous DCM (56 mL, plus 7 mL rinse) and transferred by syringe to a solution of freshly prepared triphosgene (excess phosgene gas was trapped from reaction with base trap.) (0.214 g, 0.00072 mol) and anhydrous pyridine (0.057 g, 0.00072 mol, added as solution in $CH_2Cl_2$ (~5 mL)). At one hour, a rapid argon stream was begun (room temperature-maintained) to evaporate excess phosgene (use base trap on vent). After 30 minutes of argon purge, N-hydroxysuccinimide (NHS) (0.43 g, 0.0037 mol) was added and stirred for ten minutes. Anhydrous pyridine (0.285 g, 0.0036 mol, added as solution in $CH_2Cl_2$ (~25 mL)) was added. Argon stream was continued to evaporate most of the reaction solvent after 1.5 hours. The thick syrup was dissolved in anhydrous IPA (700 mL) and precipitated at room temperature. The precipitate was filtered and washed with cold IPA and diethyl ether (100 mL containing 10 mg BHT). Residual solvents were evaporated under vacuum for off-white powder. Yield 13.5 g, 96%, substitution 87% NHS carbonate by HPLC. $^1$H-NMR ($CD_3OD$): δ (ppm) 8.7 (s, 1 H, NH Ar amide); 7.9 (m, 2 H, Ar); 7.6 (m, 2 H, Ar); 7.5 (d, 1 H, Ar); 7.3 (t, 1 H, Ar); 6.8 (bs, 1 H, NH); 6.4 (bs, 1 H, NH); 4.7 (m, 2 H, $CH_2$); 4.3 (t, 1 H, CH); 3.6 (s, PEG backbone); 3.3 (s, 6 H, —$OCH_3$); 2.8 (s, 4 H, $CH_2CH_2$); 2.5 (t, 2 H, $CH_2$); 2.3 (t, 2 H, $CH_2$); 2.0 (m, 2 H, $CH_2$).

Another polymeric reagent was prepared using this same approach except mPEG-$NH_2$ (chromatographically purified) having a weight average molecular weight of 20,000 was substituted for mPEG-$NH_2$(10,000). The resulting polymeric reagent had a total molecular weight of about 40,000 Daltons.

Another polymeric reagent was prepared using this same approach except mPEG-$NH_2$ (prepared in high purity using conventional methods) having a weight average molecular weight of 30,000 was substituted for mPEG-$NH_2$(10,000). The resulting polymeric reagent had a total molecular weight of about 60,000 Daltons.

Example 5

Preparation of Glycine Conjugates with Exemplary Polymeric Reagents and Release Data 9-Hydroxymethyl-2,7-di(mPEG(20,000)-methylamide) fluorene-N-hydroxysuccinimide (10 mg, ~70% active NHS), prepared as described in Example 1, was dissolved in a buffer solution of 1% glycine+25 mM HEPES pH 7.4 (25 μL), mixed by vortex and reacted at room temperature for 30 minutes to form a conjugate solution. Thereafter, two aliquots of the conjugate solution were treated as follows: one aliquot was diluted with 25 mM HEPES pH 7.4 (1.25 mL), incubated at 37° C. and injected on a HPLC system at various intervals; another aliquot was diluted with 25 mM HEPES pH 8.2 (buffer), incubated at 37° C. and injected on a HPLC system at various intervals.

G2PEG2Fmoc$_{20K}$-NHS, prepared as described in Example 3, was dissolved in a buffer solution of 1% glycine+25 mM HEPES pH 7.4 (25 μL), mixed by vortex and reacted at room temperature for 30 minutes to form a conjugate solution. Thereafter, two aliquots of the conjugate solution were treated as follows: one aliquot was diluted with 25 mM HEPES pH 7.4 (1.25 mL), incubated at 37° C. and injected on a HPLC system at various intervals; another aliquot was diluted with 25 mM HEPES pH 8.2 (buffer), incubated at 37° C. and injected on a HPLC system at various intervals.

G2PEG2Fmoc$_{40K}$-NHS, prepared as described in Example 3 was dissolved in a buffer solution of 1% glycine+25 mM HEPES pH 7.4 (25 μL), mixed by vortex and reacted at room temperature for 30 minutes to form a conjugate solution. Thereafter, two aliquots of the conjugate solution were treated as follows: one aliquot was diluted with 25 mM HEPES pH 7.4 (1.25 mL), incubated at 37° C. and injected on a HPLC system at various intervals; another aliquot was diluted with 25 mM HEPES pH 8.2 (buffer), incubated at 37° C. and injected on a HPLC system at various intervals.

9-Hydroxymethyl-4-(mPEG(10,000)-carboxyamide)-7-(mPEG(10,000)amidoglutaric amide)fluorene-N-hydroxysuccinimide, prepared as described in Example 4, was dissolved in a buffer solution of 1% glycine+25 mM HEPES pH 7.4 (25 μL), mixed by vortex and reacted at room temperature for 30 minutes to form a conjugate solution. Thereafter, two aliquots of the conjugate solution were treated as follows: one aliquot was diluted with 25 mM HEPES pH 7.4 (1.25 mL), incubated at 37° C. and injected on a HPLC system at various intervals; another aliquot was diluted with 25 mM HEPES pH 8.2 (buffer), incubated at 37° C. and injected on a HPLC system at various intervals.

4,7-CAC-PEG2-Fmoc$_{20K}$-NHS, prepared as described in Example 12, was dissolved in a buffer solution of 1% glycine+25 mM HEPES pH 7.4 (25 μL), mixed by vortex and reacted at room temperature for 30 minutes to form a conjugate solution. Thereafter, two aliquots of the conjugate solution were treated as follows: one aliquot was diluted with 25 mM HEPES pH 7.4 (1.25 mL), incubated at 37° C. and injected on a HPLC system at various intervals; another aliquot was diluted with 25 mM HEPES pH 8.2 (buffer), incubated at 37° C. and injected on a HPLC system at various intervals.

Release data for the $t_{1/2}$ values were obtained from the slope of the linear fit to a plot of ln([conjugate]) vs. time, according to the first order rate law.

Release data for the 9-hydroxymethyl-2,7-di(mPEG(10,000)-methylamide)fluorene-glycine carbamate conjugate at 37° C.: pH 7.4, $t_{1/2}$=9.9 days; pH 8.2, $t_{1/2}$=5.5 days (for one experiment).

Release data for the G2PEG2Fmoc$_{20k}$-glycine carbamate conjugate at 37° C.: pH 7.52±0.13, $t_{1/2}$=14.8±2.8 days; pH 8.14±0.04, $t_{1/2}$=7.0±1 days (wherein the ±ranges accounts for two experiments).

Release data for the G2PEG2Fmoc$_{40k}$-glycine carbamate conjugate at 37° C.: pH 7.52±0.13, $t_{1/2}$=12.2±2.6 days; pH 8.14±0.04, $t_{1/2}$=6.7±0.1 days (wherein the ±ranges account for 2 experiments).

Release data for the 9-hydroxymethyl-4-(carboxamido mPEG(10,000)-7-(amidoglutaric amide mPEG(10,000)) fluorene-glycine carbamate conjugate at 37° C.: pH 7.52±0.13, $t_{1/2}$=4.0±1 days; pH 8.14±0.04, $t_{1/2}$=1.95±0.15 days (wherein the ranges accounts for two experiments).

Release data for the 4,7-CAC-PEG2-Fmoc$_{20k}$-glycine carbamate conjugate at 37° C.: pH 7.4, $t_{1/2}$=18.0±0.1 days; pH 8.2, $t_{1/2}$=7.5±0.1 days (wherein the ±ranges accounts for two experiments).

Example 6

Preparation of an Exemplary Polymer-Protein Conjugate: Preparation of G2PEG2Fmoc$_{20k}$-N$^{ter}$-GLP-1

An illustrative polymeric reagent, G2PEG2Fmoc$_{20k}$-NHS, was covalently attached to the N-terminus of an illustrative polypeptide, GLP-1, to provide a prodrug form of the protein wherein a releasable PEG-moiety is attached. The two-arm nature of the polymeric reagent provides increased stability to the GLP-1 moiety subsequent to administration, to thereby provide a sustained release formulation whereby GLP-1 is released from the conjugate via hydrolysis to provide the native or unmodified GLP-1 precursor. The structure of G2PEG2Fmoc$_{20k}$-N$^{ter}$-GLP-1 is provided below (in the structure, "GLP-1" represents a residue of GLP-1). Other polypeptides and proteins can be substituted for GLP-1.

Figures 4, 6:
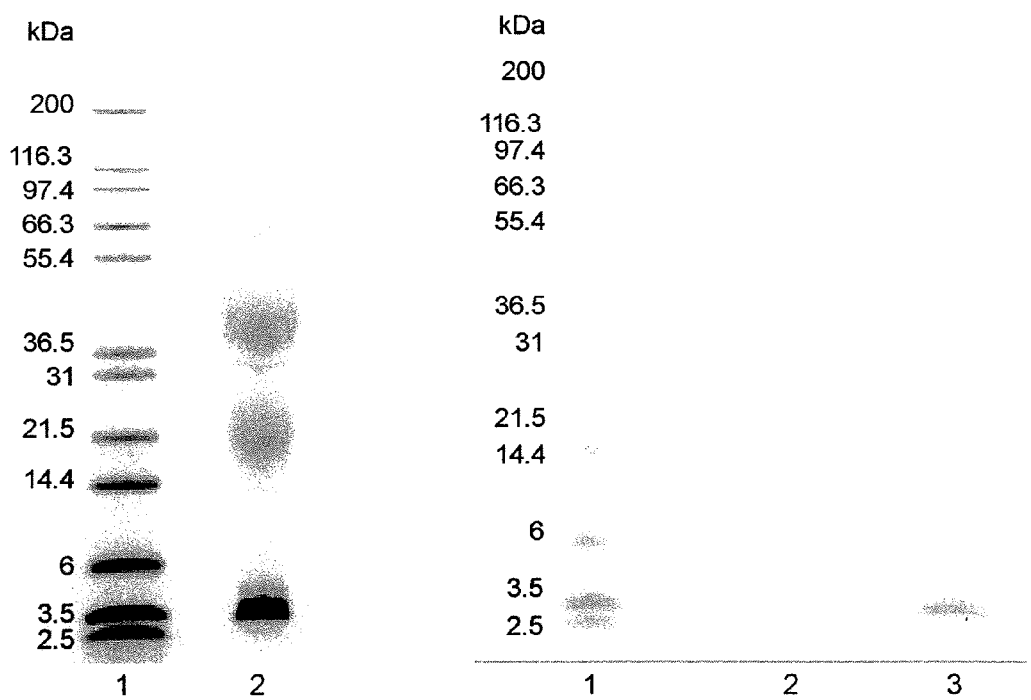
FIG. 4 corresponds to an SDS-PAGE analysis of a G2PEG2Fmoc$_{20K}$-GLP-1 reaction mixture as described in Example 6. Lane 1: Invitrogen Mark 12 unstained standard. Lane 2: G2PEG2Fmoc$_{20K}$-N$^{ter}$-GLP-1 reaction mixture.
FIG. 6 corresponds to an SDS-PAGE analysis of monoPEGylated G2PEG2Fmoc$_{20K}$-N$^{ter}$-GLP-1 before and after the release of GLP-1 (Example 6). Lane 1: Invitrogen Mark 12 unstained standard. Lane 2: MonoPEGylated G2PEG2-Fmoc$_{20k}$-N$^{ter}$-GLP-1 conjugate following purification by ion exchange chromatography. Lane 3: Following complete release of GLP-1 from the G2PEG2Fmoc$_{20k}$-N$^{ter}$-GLP-1 conjugate.

A solution of 50 mg GLP-1 (nominally 1.2276×10$^{-5}$ mol) (actual purity of GLP-1 was 98.5% (by HPLC), and the peptide content was 82.2%) in 25 mL of 20 mM sodium acetate buffer at pH 5.50 was prepared, followed by addition of 876.8 mg of G2PEG2Fmoc$_{20k}$-NHS (3.0692×10$^{-5}$ mol) with stirring. The solution was allowed to for stir 16 hours at room temperature, thereby allowing for the formation of G2PEG2Fmoc$_{20k}$-N$^{ter}$-GLP-1, a PEGylated GLP-1 conjugate. The reaction mixture was then acidified to pH 4.30 by 20 mM HAc. The reaction was monitored by SDS-PAGE analysis (FIG. 4).

Figure 5:
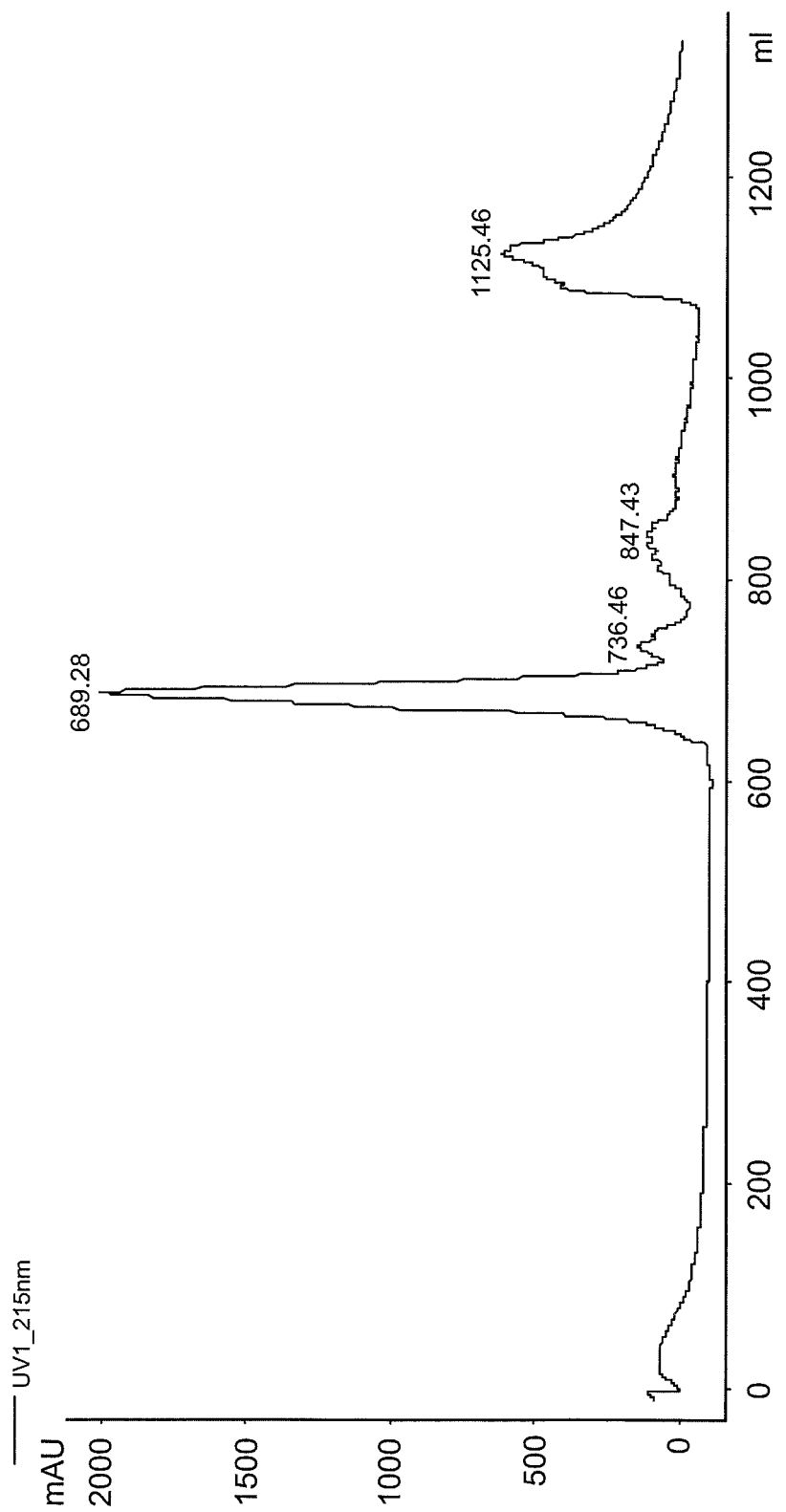
FIG. 5 demonstrates the results of purification of monoPEGylated G2PEG2Fmoc$_{20K}$-N$^{ter}$-GLP-1 by cation exchange chromatography as described in Example 6.

The G2PEG2Fmoc$_{20k}$-N$^{ter}$-GLP-1 was purified to obtain the monoPEGylated conjugate of GLP-1 by cation exchange chromatography on an ÄKTA Basic System (FIG. 5) using a mobile phase of 20 mM sodium acetate buffer at pH 4.30 (solution A) and 20 mM sodium acetate buffer with 1 M NaCl at pH 4.30 (solution B). The column was a 75 mL resin-packed HiTrap™ SP HP, available from Amersham Biosciences, packed with SP Sepharose High Performance ion exchange media, also available from Amersham Biosciences, and the flow rate in the column was 14 mL/min. The solution to be purified was first loaded onto the column. The loaded product was then eluted by the mobile phase using a gradient. The following gradient was used: for retention volumes 0 mL to 550 mL, 0% of the mobile phase contained solution B; for retention volumes 550 mL to 1041 mL, 0% of the mobile phase contained solution B; for retention volumes 1041 mL to 1093 mL, 10% of the mobile phase contained solution B; for retention volumes 1093 mL to 1338 mL, 100% of the mobile phase contained solution B; for retention volumes 1338 mL to 1486 mL, 100% of the mobile phase contained solution B; for retention volumes 1486 mL and higher, 0% of the mobile phase contained solution B. The UV absorbance of the eluent was monitored at 215 nm. The fraction corresponding to the G2PEG2Fmoc$_{20k}$-N$^{ter}$-GLP-1 (monoPEGylated form) peak at a retention volume of 689.3 mL was collected (FIG. 5) and lyophilized. The lyophilized powder was dissolved in 25 mL 20 mM sodium acetate buffer at pH 4.3, and the purification process was repeated again under the same cation exchange chromatographic conditions. Yield: 179.4 mg.

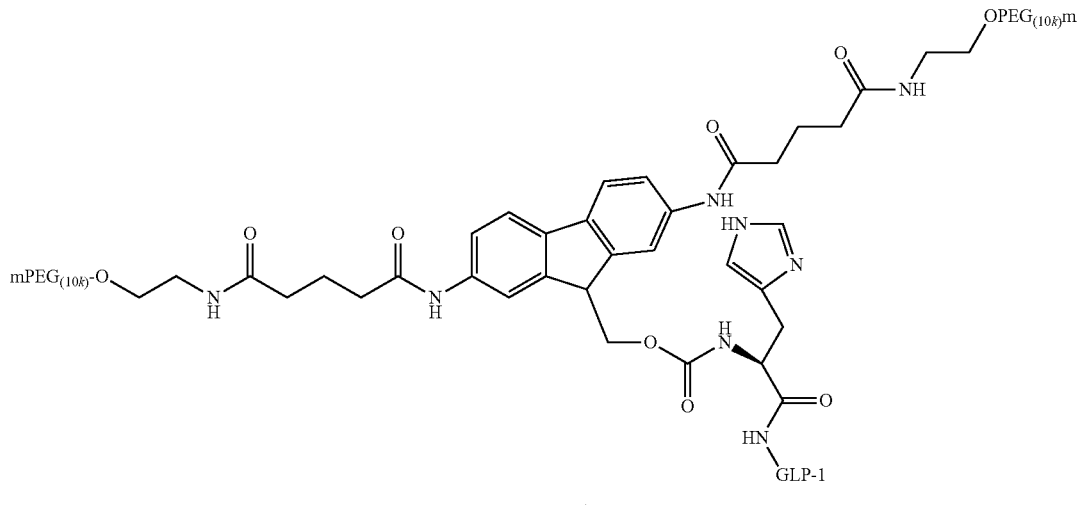

"G2PEG2Fmoc$_{20K}$-N$^{ter}$-GLP-1"

The polymeric reagent, G2PEG2Fmoc$_{20K}$-NHS, was prepared as described above in Example 3.

Figure 7A:
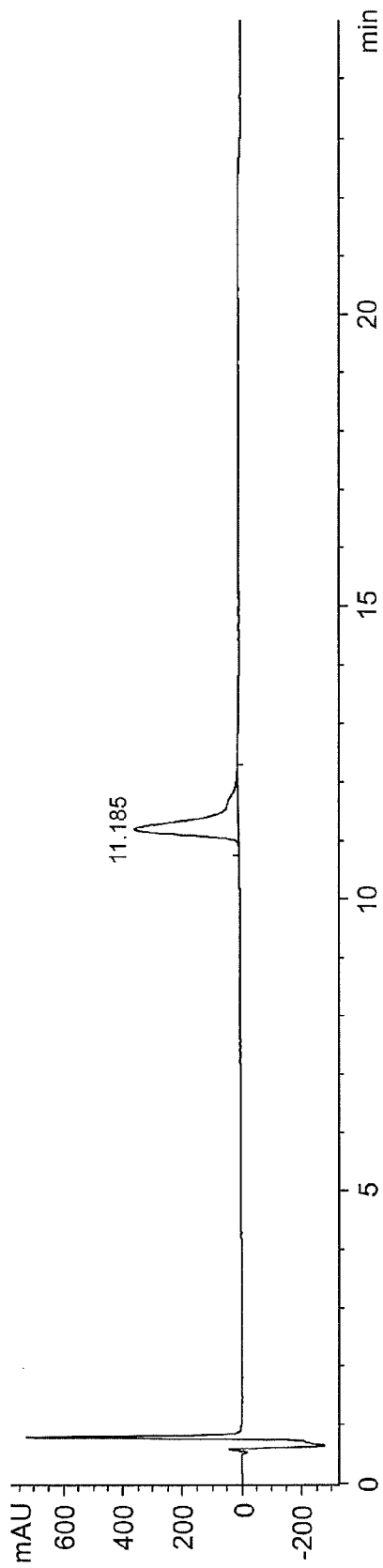
FIGS. 7A, 7B demonstrate a reverse phase HPLC analysis of monoPEGylated G2PEG2Fmoc$_{20k}$-N$^{ter}$-GLP-1 conjugate following purification by ion exchange chromatography (FIG. 7A) and after release of GLP-1 from the G2PEG2Fmoc$_{20k}$-N$^{ter}$-GLP-1 conjugate (FIG. 7B), as described in Example 6.
Figure 7B:
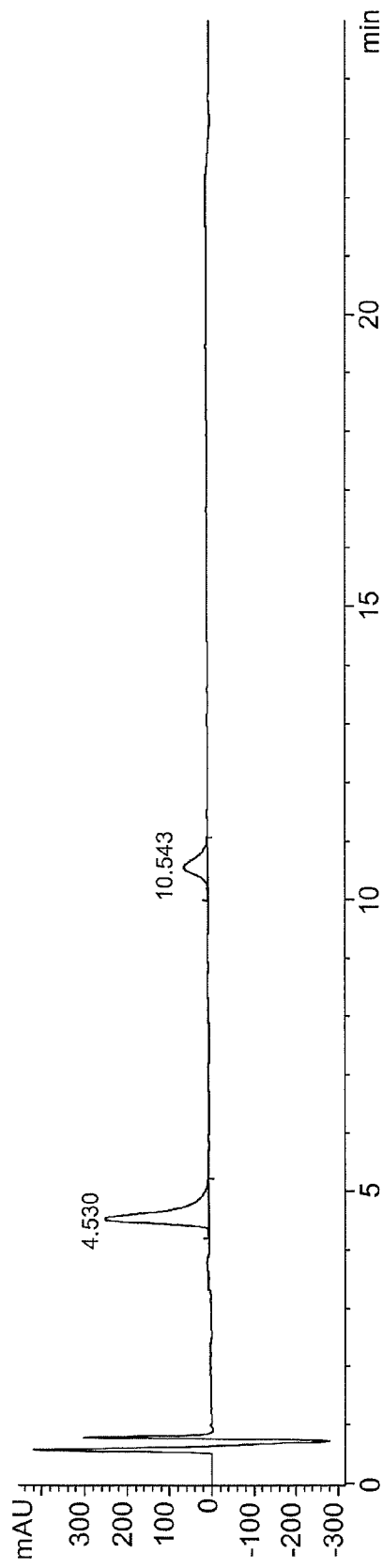

The purified G2PEG2Fmoc$_{20k}$-N$^{ter}$-GLP-1 was analyzed by SDS-PAGE (FIG. 6, Lane 2) and reverse phase HPLC (FIG. 7A). The cleavable nature of the G2PEG2Fmoc$_{20k}$-N$^{ter}$-GLP-1 conjugate in aqueous media [50 mM tris(hydroxymethyl)aminomethane (Tris) solution, pH 10, overnight at 50° C.] was also studied by both SDS-PAGE analysis (FIG. 6, Lane 3) and reverse phase HPLC (FIG. 7B), from which the complete release of GLP-1 from the conjugate was observed. The column was a 100 mm×2.1 mm ID Betasil C18 column with 5 μm particles, available from Thermo Electron Corp. Reverse phase HPLC used a mobile phase of 0.1% TFA in deionized water (solution C) and 0.1% TFA in acetonitrile (solution D) conducted at 37° C. The gradient used for reverse phase HPLC was as follows: for time 0.00 to 20.00 minutes, 35% of the mobile phase contained solution D; for time 20.00 to 21.00 minutes, 55% of the mobile phase contained solution D; for time 21.00 to 23.00 minutes, 80% of the mobile phase contained solution D; for time 23.00 to 24.00 minutes, 80% of the mobile phase contained solution D; for time 24.00 to 25.00 minutes, 35% of the mobile phase contained solution D; for time 25.00 and above, 35% of mobile phase contained solution D.

The N-terminal PEGylation site (H is) of the G2PEG2Fmoc$_{20k}$-N$^{ter}$-GLP-1 conjugate (a monoPEGylated species) was confirmed by MALDI-TOF analysis following protease digestion of the conjugate using endoproteinase Glu-C from *Straphylococcus aureus* V8.

Example 7

Figure 8:
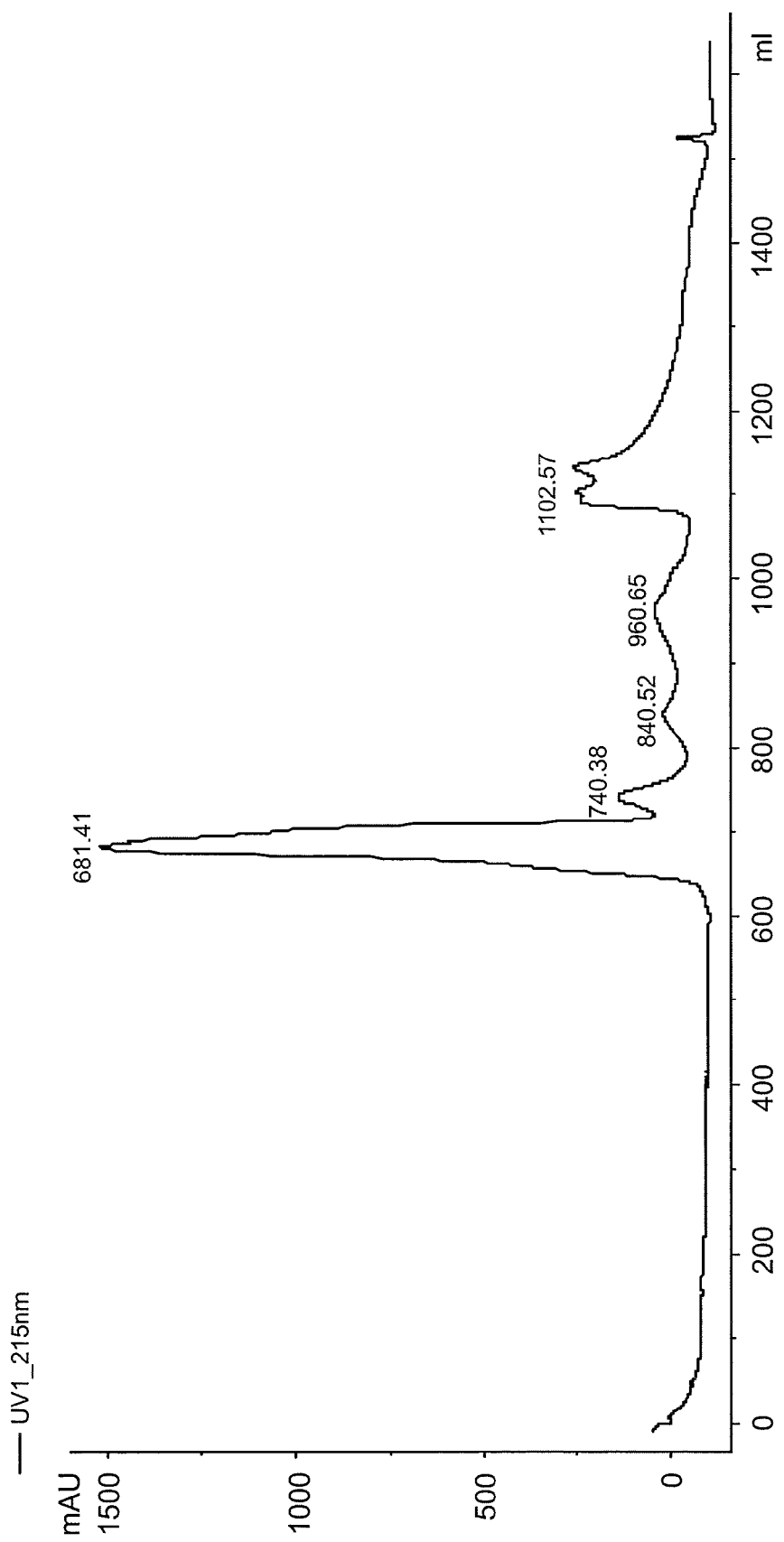
FIG. 8. illustrates the results of purification of monoPEGylated G2PEG2Fmoc$_{40k}$-N$^{ter}$-GLP-1 by cation exchange chromatography as described in Example 7.

Preparation of an Exemplary Polymer-Protein Conjugate: Preparation of G2PEG2Fmoc$_{40k}$-N$^{ter}$-GLP-1 chromatography on an ÄKTA Basic System (FIG. 8). The column was a 75 mL resin-packed HiTrap™ SP HP, available from Amersham Biosciences, packed with SP Sepharose High Performance ion exchange media, also available from Amersham Biosciences, and the flow rate in the column was 14 mL/min. The mobile phase used for the purification consisted 20 mM sodium acetate buffer at pH 4.00 (solution A) and 20 mM sodium acetate buffer with 1 M NaCl at pH 4.00 (solution B). The solution to be purified was first loaded onto the column. The loaded product was then eluted by mobile phase using a gradient. The following gradient was used: for retention volumes 0 mL to 550 mL, 0% of the mobile phase contained solution B; for retention volumes 550 mL to 1041 mL, 0% of the mobile phase contained solution B; for retention volumes 1041 mL to 1093 mL, 10% of the mobile phase contained solution B; for retention volumes 1093 mL to 1338 mL, 100% of the mobile phase contained solution B; for retention volumes 1338 mL to 1486 mL, 100% of the mobile phase contained solution B; for retention volumes 1486 mL and higher, 0% of the mobile phase contained solution B. The UV absorbance of the eluent was monitored at 215 nm. The fraction corresponding to mono G2PEG2Fmoc$_{40k}$-N$^{ter}$-GLP-1 peak at retention volume of 668.4 mL was collected (FIG. 8) and lyophilized. The lyophilized powder was dissolved in 25 mL 20 mM sodium acetate buffer at pH 4.0, and the purification process was repeated again under the same cation exchange chromatographic conditions. The collection fraction at 668 mL was lyophilized.

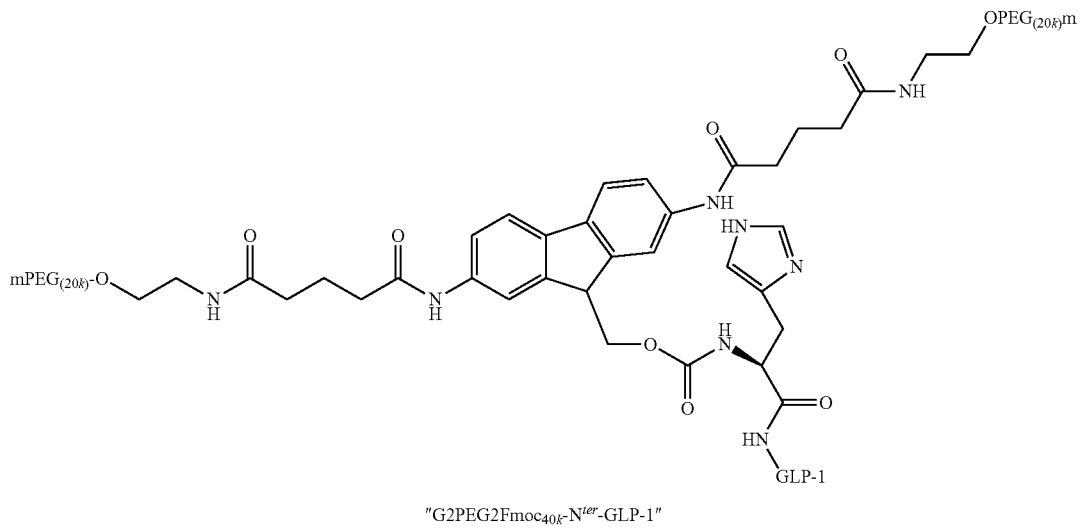

"G2PEG2Fmoc$_{40k}$-N$^{ter}$-GLP-1"

The polymeric reagent, G2PEG2Fmoc$_{40k}$-NHS, was prepared as described above in Example 3.

A solution of 50 mg GLP-1 (nominally 1.2276×10$^{-5}$ mol) (actual purity of GLP-1 was 98.5% (by HPLC), and the peptide content was 82.2%) in 25 mL of 20 mM sodium acetate buffer at pH 5.50 was prepared, followed by addition of 1.4971 gm of G2PEG2Fmoc$_{40k}$-NHS (3.0692×10$^{-5}$ mol) with stirring. The solution was allowed to stir for 15 hours at room temperature, thereby allowing for the formation of G2PEG2Fmoc$_{40k}$-N$^{ter}$-GLP-1, a PEGylated GLP-1 conjugate. The reaction mixture was acidified to pH 4.00 by 2 N HAc, followed by dilution to 50 mL with 20 mM sodium acetate buffer at pH 4.00.

Figure 9:
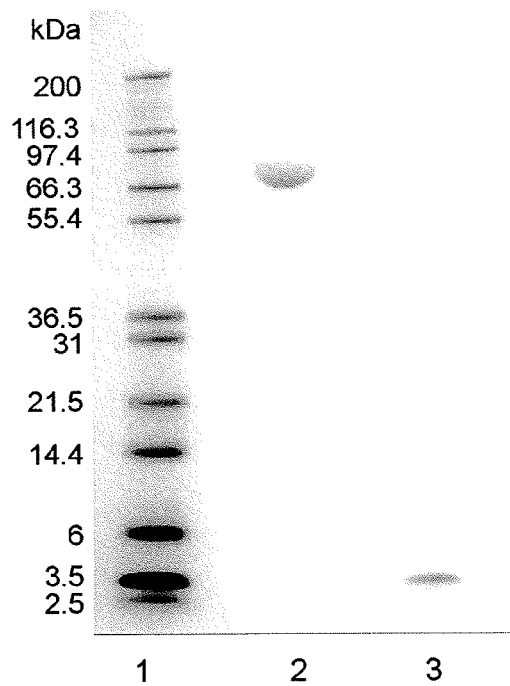
FIG. 9 shows the results of an SDS-PAGE analysis of monoPEGylated G2PEG2Fmoc$_{40k}$-N$^{ter}$-GLP-1 before and after release of GLP-1 (Example 7). Lane 1: Invitrogen Mark 12 unstained standard. Lane 2: MonoPEGylated G2PEG2Fmoc$_{40k}$-N$^{ter}$-GLP-1 conjugate following purification by ion exchange chromatography. Lane 3: Following release of GLP-1 from the G2PEG2-Fmoc$_{40k}$-N$^{ter}$-GLP-1 conjugate.

The G2PEG2Fmoc$_{40k}$-N$^{ter}$-GLP-1 was purified to obtain the monoPEGylated conjugate of GLP-1 by cation exchange The purified G2PEG2Fmoc$_{40k}$-N$^{ter}$-GLP-1 was analyzed by SDS-PAGE (FIG. 9, Lane 2). The cleavable nature of the G2PEG2Fmoc$_{40k}$-N$^{ter}$-GLP-1 conjugate in aqueous media [50 mM tris(hydroxymethyl)aminomethane (Tris) solution, pH 10, overnight at 50° C.] was also studied by SDS-PAGE analysis (FIG. 9, Lane 3), from which the complete release of GLP-1 from the conjugate was observed.

Example 8

Preparation of an Exemplary Polymer-Protein Conjugate: Preparation of G2PEG2Fmoc$_{20k}$-Lys-GLP-1

The exemplary releasable polymeric reagent, G2PEG2Fmoc$_{20k}$-NHS, was covalently and releasably attached to a lysine position of GLP-1, referred to herein as "internal" PEGylation of GLP-1.

A solution of 30 mg GLP-1 (nominally 7.3658×10$^{-6}$ mol) (actual purity of GLP-1 was 98.5% (by HPLC), and the peptide content was 82.2%) in 24.5 mL of 20 mM sodium carbonate-bicarbonate buffer at pH 10.0 was prepared, followed by addition of 276.3 mg of G2PEG2Fmoc$_{20k}$-NHS (1.1049× 10$^{-5}$ mol, prepared as described above in Example 3) with stirring. The solution was allowed to stir for ten minutes at room temperature. The reaction mixture was then acidified to pH 4.30 by 2 N HAc.

Figure 11:
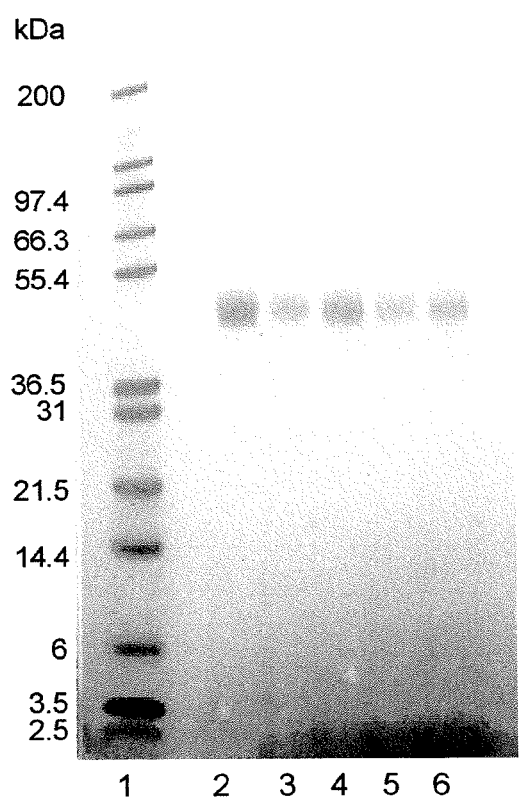
FIG. 11 corresponds to an SDS-PAGE analysis of monoPEGylated G2PEG2Fmoc$_{20k}$-Lys-GLP-1 purified by cation exchange chromatography (Example 8). Lane 1: Invitrogen Mark 12 unstained standard. Lanes 2 through 6: Fractions containing monoPEGylated G2PEG2Fmoc$_{20k}$-Lys-GLP-1 conjugate following five individual purifications by ion exchange chromatography.
Figure 10:
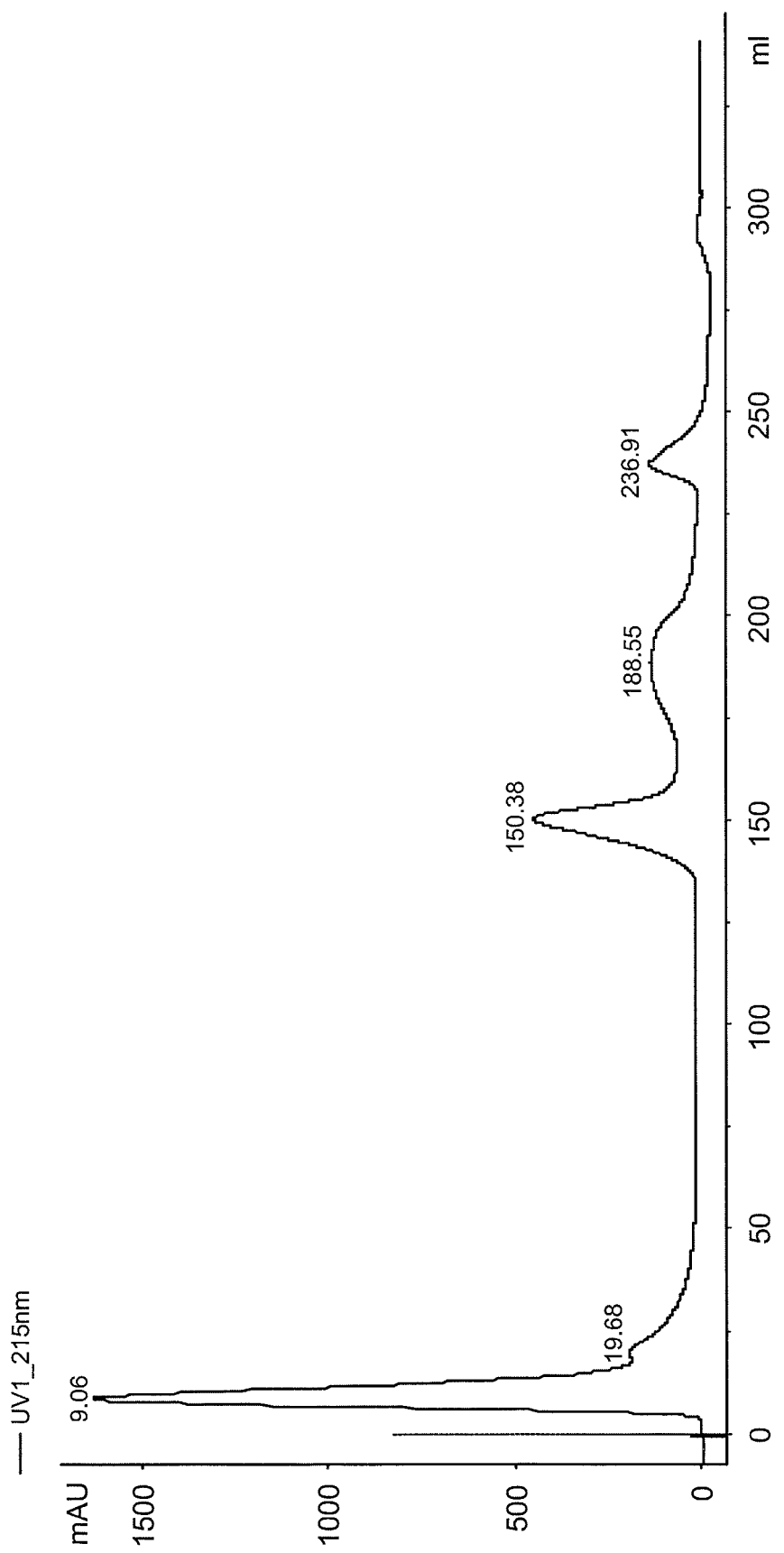
FIG. 10 demonstrates purification of monoPEGylated G2PEG2Fmoc$_{20k}$-Lys-GLP-1 by cation exchange chromatography (Example 8).

To obtain the G2PEG2Fmoc$_{20k}$-Lys-GLP-1 in monoPEGylated form, the reaction mixture was divided into five aliquots, and each aliquot was individually purified by cation exchange chromatography on an ÄKTA Basic System. The column was a 5 mL resin-packed HiTrap™ SP HP, available from Amersham Biosciences, and the flow rate in the column was 5 mL/min. The mobile phase used for the purification was 20 mM sodium acetate buffer at pH 4.30 (solution A) and 20 mM sodium acetate buffer with 1 M NaCl at pH 4.30 (solution B). The mobile phase was run using a gradient. The following gradient was used: 0 mL to 118.6 mL, 0% of the mobile phase contained solution B; for retention volumes 118.6 mL to 219.1 mL, 0% of the mobile phase contained solution B; for retention volumes 219.1 mL to 229.2 mL, 10% of the mobile phase contained solution B; for retention volumes 229.2 mL to 269.4 mL, 100% of the mobile phase contained solution B; for retention volumes 269.4 mL to 279.4 mL, 100% of the mobile phase contained solution B; for retention volumes 279.4 mL and higher, 0% of the mobile phase contained solution B. The UV absorbance of the eluent was monitored at 215 nm. The monoPEGylated GLP-1 fraction corresponding to the G2PEG2Fmoc$_{20k}$-Lys-GLP-1 peak at a retention volume of 150.4 mL was collected (FIG. 10) during each purification run. The purified G2PEG2Fmoc$_{20k}$-Lys-GLP-1 (in the monoPEGylated GLP-1 form) from each purification run was then analyzed by SDS-PAGE (FIG. 11). The collected fractions were combined and lyophilized. Yield: 41 mg.

Example 9

Preparation of an Exemplary Polymer-Protein Conjugate: Preparation of G2PEG2Fmoc$_{40k}$-Lys-GLP-1

The exemplary releasable polymeric reagent, G2PEG2Fmoc$_{40k}$-NHS, was covalently and releasably attached to a lysine position of GLP-1, referred to herein as "internal" PEGylation of GLP-1.

A solution of 50 mg GLP-1 (nominally 1.2276×10$^{-5}$ mol) (actual purity of GLP-1 was 98.5% (by HPLC), and the peptide content was 82.2%) in 45 mL of 20 mM sodium carbonate-bicarbonate buffer at pH 10.0 was prepared, followed by addition of 898.0 mg of G2PEG2Fmoc$_{40k}$-NHS (1.8414× 10$^{-5}$ mol, prepared as described in Example 3) with stirring. The solution was allowed to stir for ten minutes at room temperature. The reaction mixture was then acidified to pH 4.00 by 2 N HAc.

Figure 12:
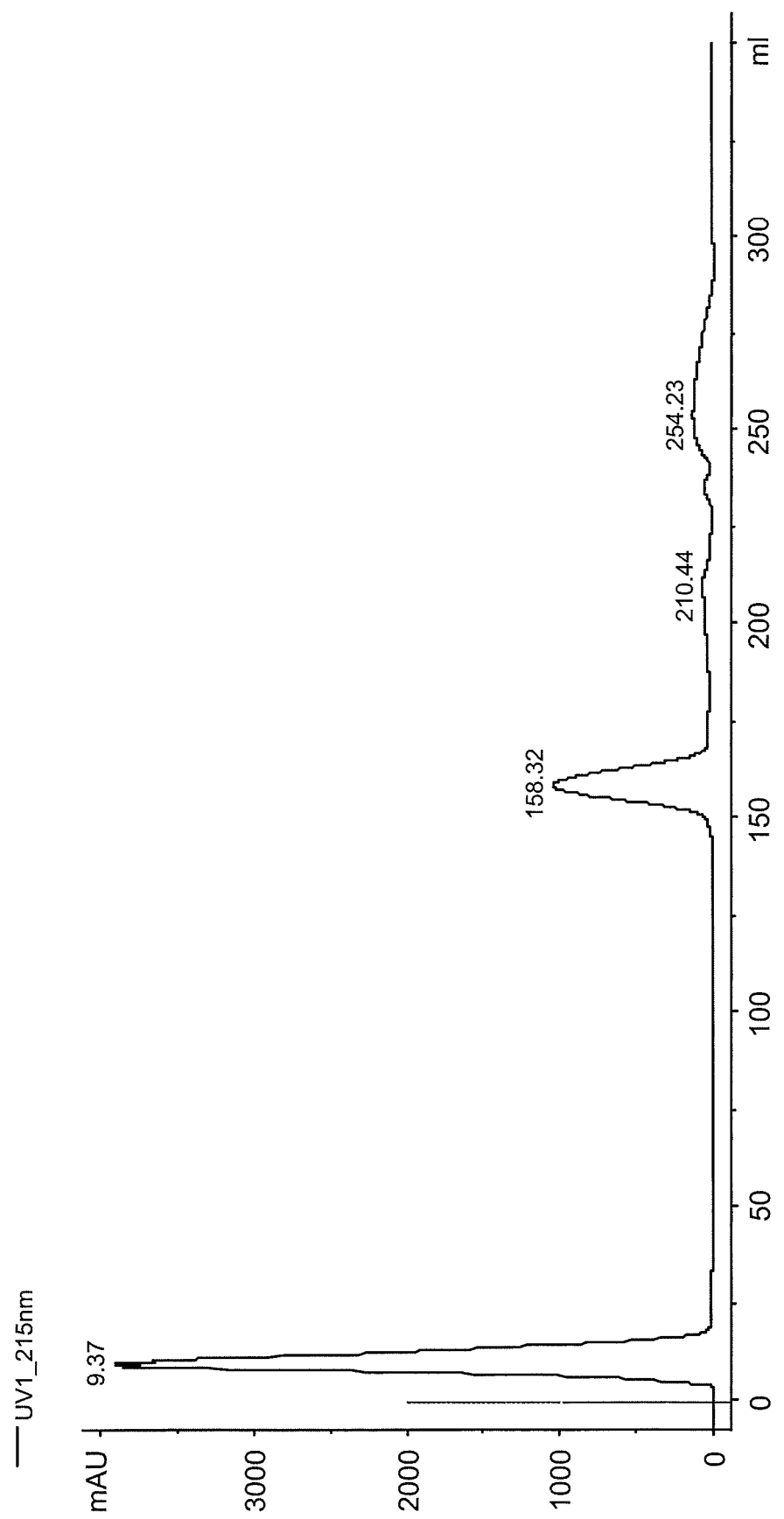
FIG. 12 illustrates the results of purification of monoPEGylated G2PEG2Fmoc$_{40k}$-Lys-GLP-1 by cation exchange chromatography (Example 9).
Figure 13:
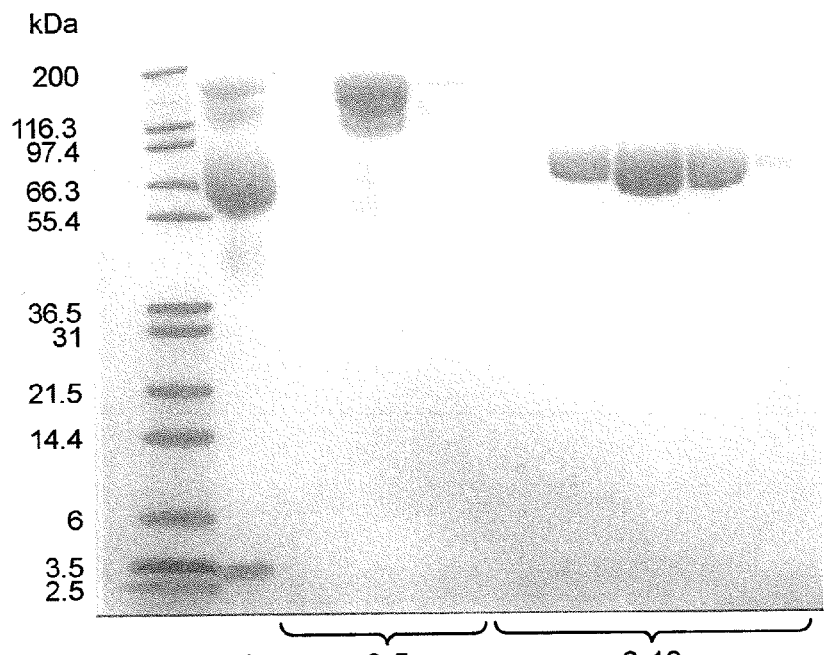
FIG. 13 represents a SDS-PAGE analysis of G2PEG2Fmoc$_{40k}$-Lys-GLP-1 reaction mixture and fractions from one cation exchange chromatographic purification as described in Example 9. Lane 1: Invitrogen Mark 12 unstained standard. Lane 2: Reaction mixture of G2PEG2Fmoc$_{40k}$-Lys-GLP-1. Lanes 3-5: Fractions from the peak at retention volume of 9.37 mL. Lanes 6-10: Fractions of monoPEGylated G2PEG2Fmoc$_{40k}$-Lys-GLP-1 collected from the peak at retention volume of 158.3 mL.

To obtain the G2PEG2Fmoc$_{40k}$-Lys-GLP-1 in monoPEGylated form, the acidified reaction mixture (50 mL), was divided into 10 aliquots, and each 5 mL aliquot was purified by cation exchange chromatography on an ÄKTA Basic System. The column was a 5 mL resin-packed HiTrap™ SP HP, available from Amersham Biosciences, and the flow rate in the column was 5 mL/min. The mobile phase used for the purification was 20 mM sodium acetate buffer at pH 4.00 (solution A) and 20 mM sodium acetate buffer with 1 M NaCl at pH 4.00 (solution B). The mobile phase was run using a gradient. The following gradient was used: 0 mL to 118.6 mL, 0% of the mobile phase contained solution B; for retention volumes 118.6 mL to 219.1 mL, 0% of the mobile phase contained solution B; for retention volumes 219.1 mL to 229.2 mL, 10% of the mobile phase contained solution B; for retention volumes 229.2 mL to 269.4 mL, 100% of the mobile phase contained solution B; for retention volumes 269.4 mL to 279.4 mL, 100% of the mobile phase contained solution B; for retention volumes 279.4 mL and higher, 0% of the mobile phase contained solution B. The UV absorbance of the eluent was monitored at 215 nm. The monoPEGylated GLP-1 fraction corresponding to the G2PEG2-Fmoc$_{40k}$-Lys-GLP-1 peak at a retention volume of 158.3 mL was collected (FIG. 12) during each purification run. The purified G2PEG2Fmoc$_{40k}$-Lys-GLP-1 (in the monoPEGylated GLP-1 form) from each purification run was analyzed by SDS-PAGE (FIG. 13). The collected fractions were combined, concentrated by ultrafiltration and lyophilized. Yield: 187.5 mg.

Example 10

In-Vivo Study in Mice to Examine the Blood-Glucose Lowering Effects of Illustrative GLP-1 Polymer Conjugates Male diabetic mice (BKS.Cg-+Lepr db/+Lepr db/01aHsd) were purchased from Harlan Laboratories, Ltd. (Jerusalem, Israel). The 8-9 week old animals (30-40 gm) were placed in mouse cages (two animals per cage), and allowed at least 48 hours of acclimatization before the start of the study.

Preparation of G2PEG2Fmoc$_{20k}$-N$^{ter}$-GLP-1 (Example 6), G2PEG2Fmoc$_{40k}$-N$^{ter}$-GLP-1 (Example 7), G2PEG2Fmoc$_{20k}$-Lys-GLP-1 (Example 8), and G2PEG2Fmoc$_{40k}$-Lys-GLP-1 (Example 9), were described in the preceding examples. Each compound was accurately weighed into a glass vial and dissolved in normal saline in order to prepare a concentration that would accommodate for the dose (based on GLP-1 equivalents) and the injection volume of 100 µL.

The study was divided into two phases: a feasibility phase and an evaluation phase.

In the feasibility phase, the feasibility of using diabetic db/db mice to test the effectiveness of GLP-1 was first evaluated. In carrying out the feasibility phase, several groups of mice were used wherein four mice were used in each group. Data on the baseline glucose levels were gathered for each mouse for 2-3 days prior to drug dosing. This was performed to identify any outliers in the group of animals. On the day of treatment (Day 0) each animal was weighed. A time 0 day blood sample (5 to 10 µL) was collected from the tail vein. The glucose level (mg/dL) was measured using a glucose analyzer. Each animal was then dosed subcutaneously (SC) below the skin on the back. The amount of test article and the dose (60 and 120 µg/mouse) administered was based on the average body weight of the animal, and the total volume of the dose did not exceed 10 mL/kg. The animals were then allowed to return into their cages. Blood samples of 5 to 10 µL (<0.5% of 2 mL blood volume for a 35 g mouse) were removed through a needle prick/capillary tube at the following time points: −3, −2, −1, 0, 0.04, 0.16, 0.33, 1.0, 1.16 days. Each collected blood sample was tested for its glucose level. At the end of the study, the animals were humanely euthanized by carbon-dioxide asphyxiation.

In the evaluation phase, the results from the feasibility phase were used to select the appropriate doses required to attain a sustained delivery of GLP-1 for a 3-5 day effect. In carrying out the evaluation phase, eight mice were used in each group. Data on the baseline glucose levels were gathered for each mouse three days prior to drug dosing. On the day of treatment (Day 0) each animal was weighed. A time 0 day blood sample (5 to 10 µL) was collected from the tail vein. The glucose level (mg/dL) was measured using a glucose analyzer. Each animal was then dosed subcutaneously (SC) below the skin on the back. The amount of test article administered was based on the average body weight of the animal, and the total volume of the dose did not exceed 10 mL/kg. The animals were then allowed to return into their cages. Blood samples of 5 to 10 µL (<0.5% of 2 mL blood volume for a 35 g mouse) were removed through a needle prick/capillary tube at the following time points: −3, −2, −1, 0, 0.04, 0.16, 0.33, 0.5, 1, 2, 3, 6 days. Each collected blood sample was tested for its glucose level. Food was withdrawn from the animals for the first four hours after dosing. At the end of the study, the animals were humanely euthanized by carbon-dioxide asphyxiation.

Table 2 below describes the test compounds and the dose for each group of animals.

TABLE 2

Test Compounds and Dose for Each Group of Animals

| Treatment | Lot or Reference Nos. | Number of mice per group | Dose (in µg) |
|---|---|---|---|
| Negative control (saline) | Baxter, lot C645028 | 8 | — |
| Positive control 2 (GLP-1) | American Peptide, lot T05128191 | 8 | 60, 120 |
| G2PEG2Fmoc$_{20K}$-Lys$_{(26\ or\ 34)}$-GLP1 | ZH 071805 | 8 | 420 |
| G2PEG2Fmoc$_{40K}$-Lys$_{(26\ or\ 34)}$-GLP1 | ZH 072305 | 8 | 420 |
| G2PEG2Fmoc$_{20K}$-N$^{ter}$-GLP1 | ZH 082405 ZH 092105 | 8 | 420 |
| G2PEG2Fmoc$_{40K}$-N$^{ter}$-GLP1 | ZH 082505 CP2F1 ZH 082505 CP2F2 | 8 | 420 |

Figure 14:
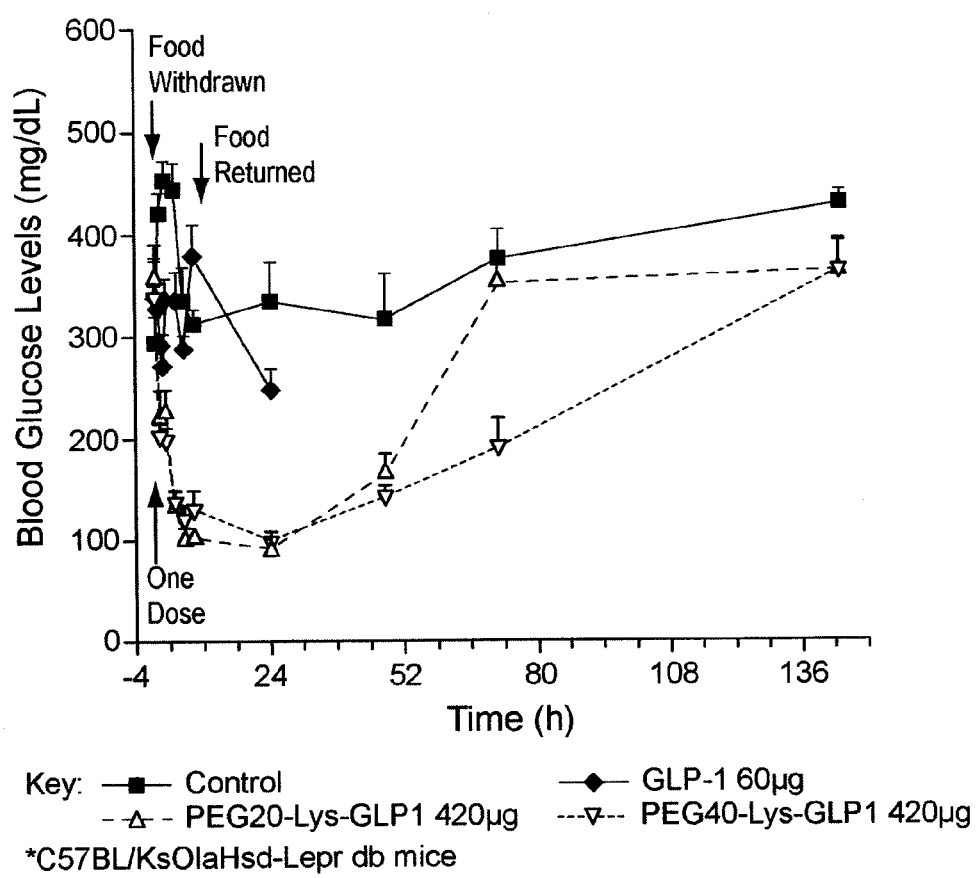
FIG. 14 is a plot demonstrating the comparative blood glucose-lowering effects over time of GLP-1, G2PEG2Fmoc$_{20k}$-Lys-GLP-1 conjugate and G2PEG2Fmoc$_{40k}$-Lys-GLP-1 conjugate when subcutaneously administered to db/db mice as described in Example 10.

The data from the study was collected and analyzed. It was noted that the animals tolerated the single subcutaneous dose. As illustrated in FIG. 14, the blood glucose-lowering effect of GLP-1 and each of the G2PEG2Fmoc$_{20K}$-Lys-GLP-1 (designated as "PEG20-Lys-GLP1" in the figure) and G2PEG2Fmoc$_{40K}$-Lys-GLP-1 (designated as "PEG40-Lys-GLP1" in the figure) conjugates was confirmed. It can be seen from the pharmacodynamic (PD) measurements that GLP-1 was cleared rapidly from the mouse, but that the GLP-1 conjugates released the peptide over a period of 3 to 4 days. That is to say, the exemplary GLP-1 degradable conjugates of the invention function somewhat like a molecular pump, releasing intact GLP-1 over time by in-vivo hydrolysis. The covalently attached hydrophilic polymer (i.e., PEG) functions not only to stabilize the GLP-1 in-vivo (i.e., by protecting the protein from enzymatic degradation), but also to extend its circulating half-life by slowly releasing the protein into the bloodstream over an extended period of 3 to 4 days. The 40 kiloDalton PEG conjugate was also observed to have a small but extended PD effect when compared to the 20 kiloDalton PEG conjugate.

The data from FIG. 14 suggest that: (a) GLP-1 is released into the mouse blood from the site of injection by diffusion and by hydrolysis from the PEGylated conjugate; and (b) the blood glucose-lowering activity of the lysine conjugated PEG-GLP1 may be due to the combination of the activity of the intact conjugates and the apparent in-vivo release of the peptide from the subject conjugates.

Figure 15:
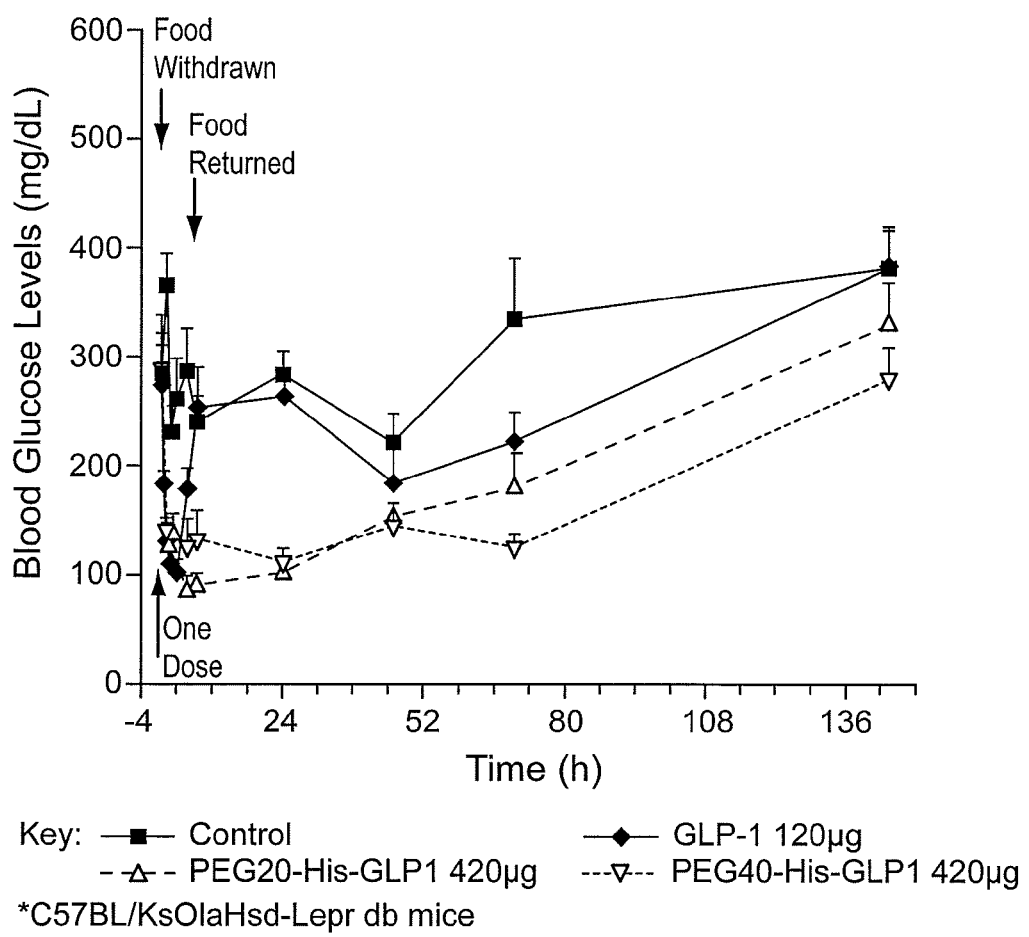
FIG. 15 is a plot demonstrating the comparative blood glucose-lowering effects over time of GLP-1, G2PEG2Fmoc$_{20k}$-N$^{ter}$-GLP-1 conjugate and G2PEG2Fmoc$_{20k}$-N$^{ter}$-GLP-1 conjugate when subcutaneously administered to db/db mice as described in Example 10.

FIG. 15 illustrates the blood glucose-lowering effect of GLP-1 and G2PEG2Fmoc$_{20K}$-N$^{ter}$-GLP-1 (designated as "PEG20-His-GLP1" in the figure) and G2PEG2Fmoc$_{40K}$-N$^{ter}$-GLP-1 (designated as "PEG40-His-GLP1" in the figure). It is evident from the pharmacodynamic (PD) measurements that GLP-1 is cleared rapidly from the mouse, but the PEG GLP-1 conjugates release the peptide over a period of 3 to 4 days. It is also observed that the PEG 40 kilodalton conjugate had a small but extended PD effect when compared to the PEG 20 kilodalton conjugate.

This set of data (FIG. 15) suggest that: (a) GLP-1 is released into the mouse blood from the site of injection by diffusion and by hydrolysis from the PEGylated conjugate; and (b) the histidine-conjugated PEG-GLP1 is not active, and the blood glucose-lowering activity observed is the result of release of the peptide from the conjugate.

This study demonstrates that one injection of PEGylated GLP-1 as described herein can be used to control diabetes over an extended period of more than 48 hours. This study also demonstrates the sustained release property of the G2PEG2Fmoc reagents when conjugated to GLP-1. This study also showed that GLP-1 can be PEGylated at the N-terminus to provide a product for parenteral administration.

Example 11

In Vitro Release Profile of G2PEG2Fmoc$_{20K}$-N$^{ter}$-GLP-1

The in vitro release profile of G2PEG2Fmoc$_{20K}$-N$^{ter}$-GLP-1 was determined. G2PEG2Fmoc$_{20K}$-N$^{ter}$-GLP-1 (in the form of monoPEGylated GLP-1) was prepared as described in Example 6 and was used to evaluate the release of a protein.

The conditions used to determine the in vitro release profile G2PEG2Fmoc$_{20K}$-N$^{ter}$-GLP-1 included: 2 mg/mL G2PEG2Fmoc20K-N$^{ter}$-GLP-1 (monoPEGylated GLP-1 form) in phosphate-buffered saline, pH 7.4, 37° C., with samples taken at various time points and tested for the presence of "free" or unconjugated GLP-1. The release of GLP-1 was monitored by reverse phase HPLC at 215 nm.

Figure 16:
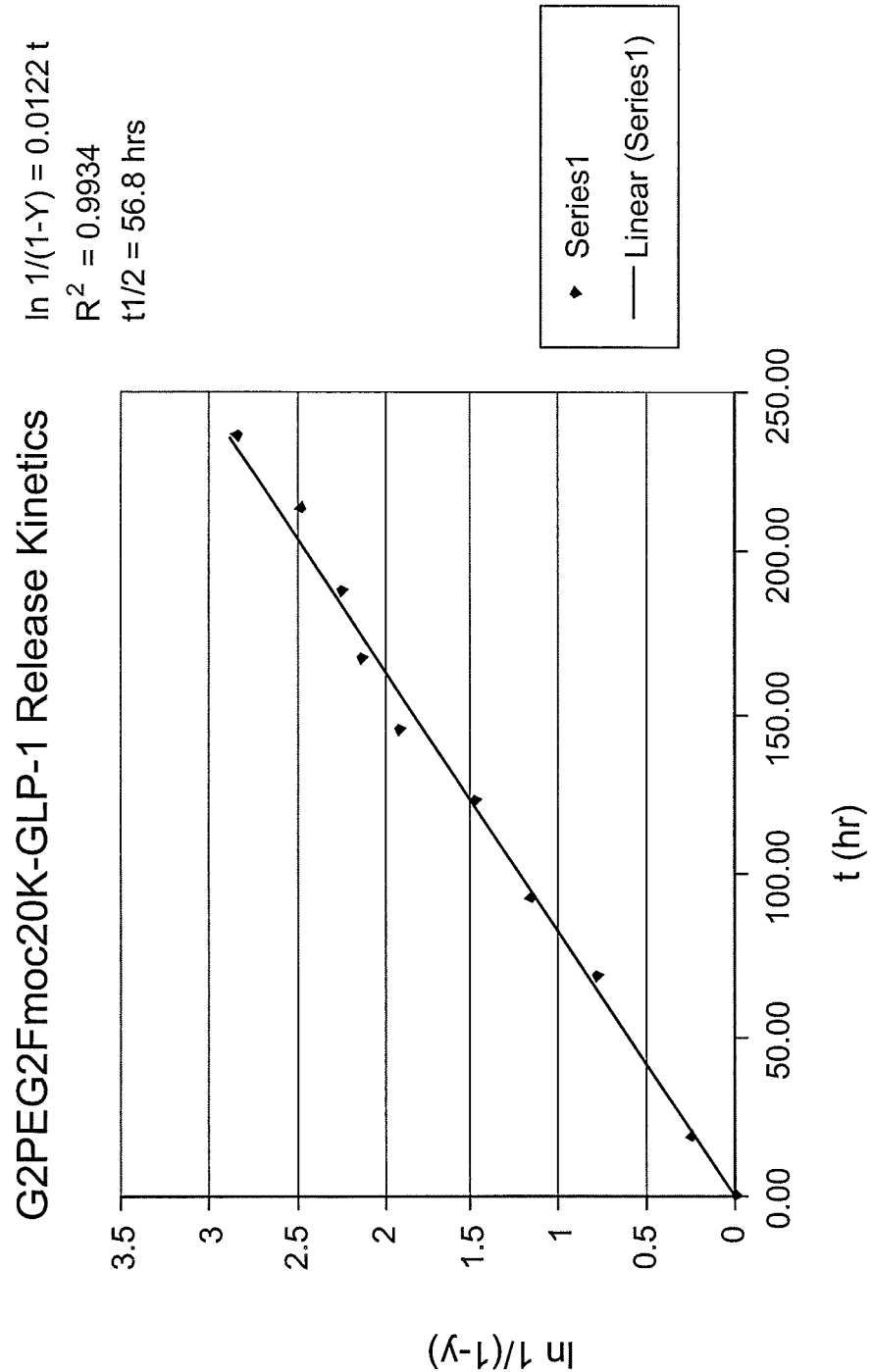
FIG. 16 is a plot of the results obtained from the experiment performed in Example 11.

FIG. 16 sets forth the results of the experiment is graph form, where Y=A$_t$/A$_{max}$ (A$_t$ is HPLC peak area of released GLP-1 at time of t (hr) and A$_{max}$ is HPLC peak area of GLP-1 reached its maximum release). Because the reaction kinetics represent a first order reaction due to the linearity of the plot, it can be concluded that ln 1/(1−Y)=kt, where k is the slope, t$_{1/2}$=ln 2/k.

Example 12

Preparation of 9-hydroxymethyl-4-(mPEG(10,000)-carboxyamide)-7-(3-(mPEG(10,000))carbamoyl-propyl)fluorene-N-hydroxysuccinimide; (or "4,7-CAC-PEG2-Fmoc$_{20K}$-NHS")

The synthesis of 9-hydroxymethyl-4-(mPEG(10,000)-carboxyamide)-7-(3-(mPEG(10,000))carbamoyl-propyl)fluorene-N-hydroxysuccinimide is represented schematically in Scheme 4, below.

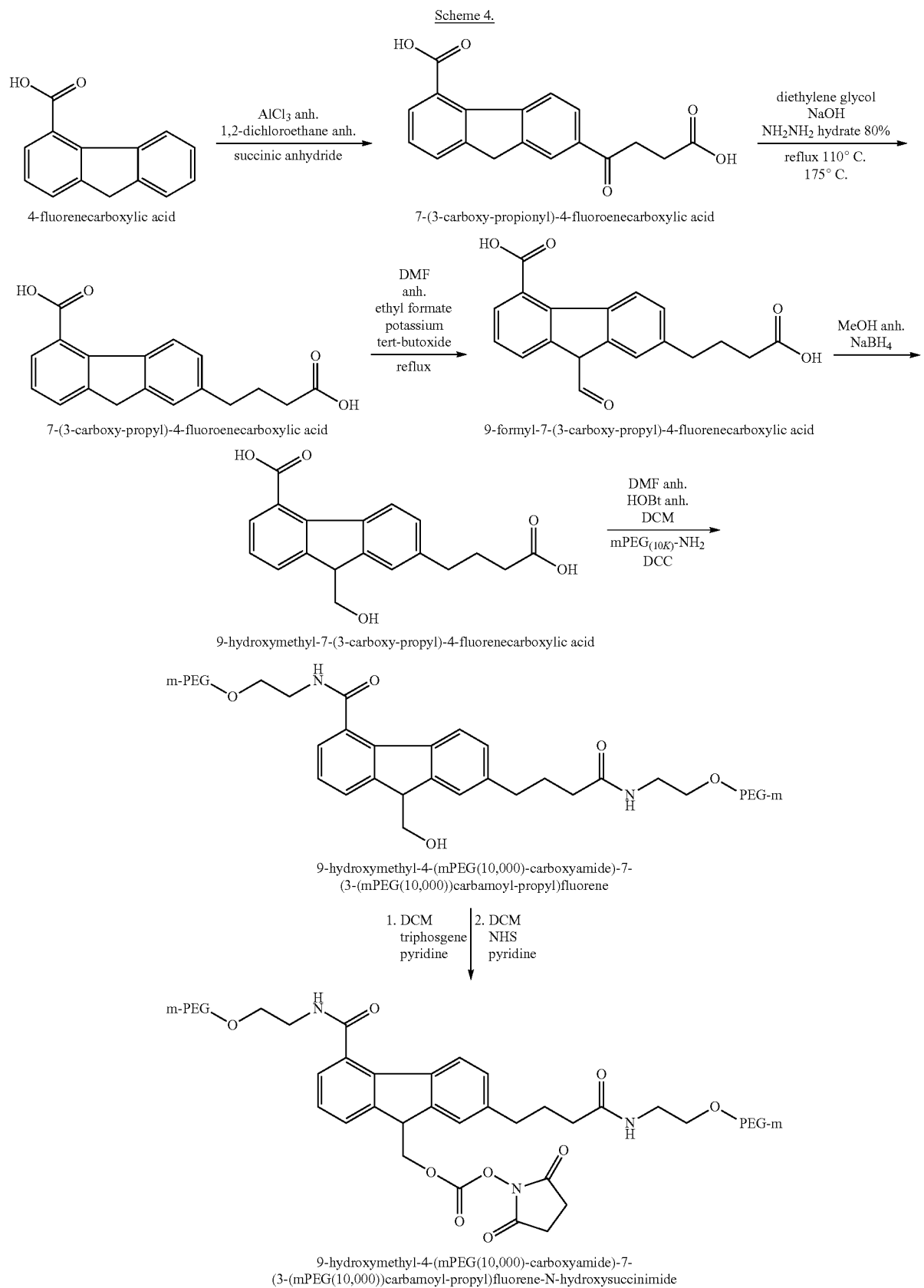

A. Preparation of 7-(3-carboxy-propionyl)-4-fluorenecarboxylic acid

In a dry argon-purged round bottom flask anhydrous $AlCl_3$ (26.9 g, 0.202 mol) was suspended in anhydrous 1,2-dichloroethane (60 mL). 4-Fluorenecarboxylic acid (10.0, g, 0.048 mol) was added to the suspension. The reaction flask was placed in a room temperature bath and succinic anhydride (5.72 g, 0.057 mol) was carefully added. The reaction was stirred for five hours and then cooled to 0° C. The reaction was very carefully quenched by the slow portion-wise addition of 3 M HCl (Caution! The reaction can react violently when HCl is added too rapidly.) The final well mixed suspension was acidic and not reactive to additional HCl solution. The organic solvent was removed at reduced pressure and the product was filtered and washed well with water. The crude product was dissolved in warm NaOH solution (approximately $\leqq 1$ M NaOH), filtered and precipitated with the addition of concentrated HCl. The product was filtered washed with water and then dried at reduced pressure in the presence of $P_2O_5$. The product was a pale yellow solid (14.3 g, 97%). $^1$H-NMR ($d_6$-DMSO): δ (ppm) 8.4 (d, 1H, Ar); 8.2 (s, 1H, Ar); 8.0 (d, 1H, Ar); 7.8 (m, 2H, Ar); 7.5 (t, 1H, Ar); 4.1 (s, 2H, $CH_2$); 2.6 (t, 2H, $CH_2$) 2.5 (under DMSO, $CH_2$).

B. Preparation of 7-(3-carboxy-propyl)-4-fluorenecarboxcylic acid

In an argon-purged flask 7-(3-carboxy-propionyl)-4-fluorenecarboxylic acid (14.0 g, 0.045 mol) was suspended in diethylene glycol (200 mL). The flask was placed in a room temperature oil bath and then NaOH (18 g, 0.450 mol) and an 80% solution of hydrazine hydrate (13.6 mL, 0.223 mol) were added successively. The reaction mixture was slowly heated to 110° C. and refluxed for approximately two hours. The reaction temperature was raised to 200° C. with removal of water during the heating process. After three hours at 200° C. reaction temperature the reaction was cooled to approximately 60° C. The reaction mixture was carefully poured into water (approximately 1 L) and the mixture was acidified to pH 2 with concentrated HCl. The product was filtered and washed with water. The product was dissolved in warm NaOH solution (0.5M) and precipitated by acidification to pH 2 with HCl. The product was filtered and washed with water. Product was an off-white solid (10.9 g, 82%). $^1$H-NMR ($d_6$-DMSO): δ (ppm) 8.3 (d, 1H, Ar); 7.7 (m, 2H, Ar); 7.4 (s, 1H, Ar); 7.4 (t, 1H, Ar); 7.2 (d, 1H, Ar); 3.9 (s, 2H, $CH_2$); 2.7 (t, 2H, $CH_2$); 2.3 (t, 2H, $CH_2$); 1.9 (m, 2H, $CH_2$).

C. Preparation of 9-formyl-7-(3-carboxy-propyl)-4-fluorenecarboxylic acid

In a dry argon-purged flask with a reflux condenser, 7-(3-carboxy-propyl)-4-fluorenecarboxylic acid (4.0 g, 0.0135 mol) was dissolved in anh. DMF (120 mL) at 40° C. Ethyl formate (40 mL, stored over $K_2CO_3$ anh.) was added followed by addition of potassium tert-butoxide 95% (12.8 g, 0.108 mol, added in 2 portions). The reaction was stirred at about 40° C.-50° C. for four hours with the addition of anh. DMF (80 mL), anhydrous THF (5 mL) and ethyl formate (25 mL) at various intervals to aid solubility. The reaction was then stirred another 17 hours at room temperature. The ethyl formate was evaporated at reduced pressure. The reaction was quenched with water (150 mL) and acidified to pH 2 with concentrated HCl. The product was twice extracted with ethyl acetate (600 mL then 200 mL). The combined organic layers were washed 3 times with brine, dried over sodium sulfate, filtered and evaporated to dryness. The crude product (4.7 g, ~100%, purity 80%) contained some unreacted starting material. $^1$H-NMR ($d_6$-DMSO): δ (ppm) 11.4 (s, 1H, formyl); 8.3-7.0 (m, 7H, Ar); 2.7 (m, 2H, $CH_2$); 2.3 (m, 2H, $CH_2$); 1.9 (m, 2H, $CH_2$).

D. Preparation of 9-hydroxymethyl-7-(3-carboxy-propyl)-4-fluorenecarboxylic acid In an argon-purged flask, crude 9-formyl-7-(3-carboxy-propyl)-4-fluorenecarboxylic acid (4.0 g, 0.0123 mol) was dissolved in anhydrous methanol (50 mL). The flask was placed in a room temperature bath and sodium borohydride (2.3 g, 0.0615 mol) was carefully added to the reaction in portions (Caution! Flammable gas evolution.). The reaction was stirred for two hours and another portion of sodium borohydride was added (1.2 g, 0.031 mol). After another six hours the reaction was treated with a small amount of water. The organic solvent was partially removed at reduced pressure and the mixture was acidified with concentrated HCl. Brine was added and the product was twice extracted with ethyl acetate (300 mL and 100 mL). The combined organic layers were washed with brine, dried over sodium sulfate, filtered and evaporated to dryness. The crude product (3.3 g, 83%) was purified by flash chromatography: silica gel 60 Å eluted with 50:50:2 ethyl acetate/chloroform/glacial acetic acid. The purified product was an orange solid (1.7 g, 43%). $^1$H-NMR ($CD_3OD$): δ (ppm) 8.3 (d, 1H, Ar); 7.8 (m, 2H, Ar); 7.6 (s, 1H, Ar); 7.4 (t, 1H, Ar); 7.2 (m, 1H, Ar); 4.0 (m, 2H, $CH_2$); 3.9 (m, 1H, CH); 2.8 (t, 2H, $CH_2$); 2.4 (t, 2H, $CH_2$); 2.0 (m, 2H, $CH_2$).

E. Preparation of 9-hydroxymethyl-4-(mPEG(10, 000)-carboxyamide)-7-(3-(mPEG(10,000))carbamoyl-propyl)fluorene mPEG-$NH_2$(10,000) ($M_n$=9,418; chromatographically purified, 25.8 g, 0.0026 mol, also designated as "mPEG$_{(10k)}$-$NH_2$") in anhydrous toluene (250 mL) was azeotropically distilled under reduced pressure at 45° C. on a rotary evaporator. The solids were dissolved in anhydrous DCM ($CH_2Cl_2$) (130 mL) under an inert atmosphere. A solution of 9-hydroxymethyl-7-(3-carboxy-propyl)-4-fluorenecarboxylic acid (0.38 g, 0.0012 mol) and anhydrous N-hydroxybenzotriazole (HOBt) (0.33 g, 0.0025 mol) in anhydrous DMF (12.5 mL) was quantitatively added to the PEG solution (5 mL DMF to rinse). 1,3-Dicyclohexylcarbodiimide (DCC) (0.54 g, 0.0026 mol) was then added to the reaction solution. The reaction was stirred at room temperature for 21 hours before solvent was evaporated at reduced pressure. The thick syrup was dissolved in dry IPA (900 mL, slow addition) with gentle heating. The PEG product precipitated by addition of diethyl ether (400 mL) at room temperature. The precipitate was cooled to 10° C. for ten minutes, filtered and washed with cold IPA (300 mL) and then diethyl ether (300 mL). The crude product (off-white powder) was dried under hi-vacuum and then dissolved in deionized water. Ion exchange chromatography of the PEG solution was preformed on POROS media (500 mL) eluting with water. Fractions containing neutral PEG were collected and further purified with DEAE Sepharose media (200 mL). The purified product was not found to contain mPEG-$NH_2$ (10,000) or monoPEG acid products (HPLC analysis). Yield 17 g, 71% (substitution 95%). $^1$H-NMR ($CD_2Cl_2$): δ (ppm) 7.9 (d, 1H, Ar); 7.7 (d, 1H, Ar); 7.5 (s, 1H, Ar); 7.4 (m, 1H, Ar); 7.3 (t, 1H, Ar); 7.2 (d, 1H, Ar); 6.7 (bs, 1H, amide); 6.2 (bs, 1H, amide); 4.1 (m, 2H, CH$_2$); 3.8 (m, 1H, CH); 3.6 (s, PEG backbone); 3.3 (s, 6H, —OCH$_3$); 2.7 (m, 2H, CH$_2$); 2.2 (m, 2H, CH$_2$); 1.9 (water+m, 2H, CH$_2$).

F. Preparation of 9-hydroxymethyl-4-(mPEG(10,000)-carboxyamide)-7-(3-(mPEG(10,000))carbamoyl-propyl)fluorene-N-hydroxysuccinimide The 9-hydroxymethyl-4-(mPEG(10,000)-carboxyamide)-7-(3-(mPEG(10,000))carbamoyl-propyl)fluorene (2.9 g, 0.00015 mol) in anhydrous toluene (50 mL) was azeotropically distilled under reduced pressure at 45° C. on a rotary evaporator. The solid was dissolved in anhydrous DCM (15 mL, plus 1 mL rinse) and transferred by syringe to a solution of freshly prepared triphosgene (excess phosgene gas was trapped from reaction with base trap.) (0.047 g, 0.00016 mol) and anhydrous pyridine (0.013 g, 0.00016 mol, added as solution in CH$_2$Cl$_2$ (~0.9 mL)). At one hour, a rapid argon stream was begun (room temperature-maintained) to evaporate excess phosgene (use base trap on vent). After 30 minutes of argon purge, N-hydroxysuccinimide (NHS) (0.09 g, 0.00078 mol) was added and stirred for ten minutes. Anhydrous pyridine (0.059 g, 0.00075 mol, added as solution in CH$_2$Cl$_2$ (~4.5 mL)) was added. The argon stream was continued to evaporate most of the reaction solvent after 1.5 hours. The thick syrup was dissolved in anhydrous IPA (150 mL) and precipitated at room temperature. The precipitate was filtered and washed with cold IPA and diethyl ether (30 mL containing 5 mg BHT). Residual solvents were evaporated under vacuum for off-white powder. Yield 2.7 g, 90%, substitution 76% NHS carbonate by HPLC. $^1$H-NMR (CD$_3$OD): δ (ppm) 7.9 (m, 1H, Ar); 7.7 (m, 1H, Ar); 7.5 (m, 2H, Ar); 7.4 (m, 1H, Ar); 7.2 (m, 1H, Ar); 6.8 (bs, 1H, amide); 6.1 (bs, 1H, amide); 4.7 (m, 2H, CH$_2$); 4.3 (t, 1H, CH); 3.6 (s, PEG backbone); 3.3 (s, 6 H, —OCH$_3$); 2.7 (s, 4H, CH$_2$CH$_2$); 2.7 (m, 2H, CH$_2$); 2.2 (t, 2H, CH$_2$); 2.0 (m, 2H, CH$_2$).

Example 13

Preparation of 9-hydroxymethyl-2,7-fluorenedicarboxylic acid, an intermediate for the preparation of 9-hydroxymethyl-2,7-(bis-mPEG$_{10K}$-carboxyamide)-fluorene-N-hydroxysuccinimide (2,7-C2-PEG2-Fmoc$_{20K}$-NHS)

The synthesis of 9-hydroxymethyl-2,7-fluorenedicarboxylic acid is represented schematically in Scheme 5, below.

Scheme 5.

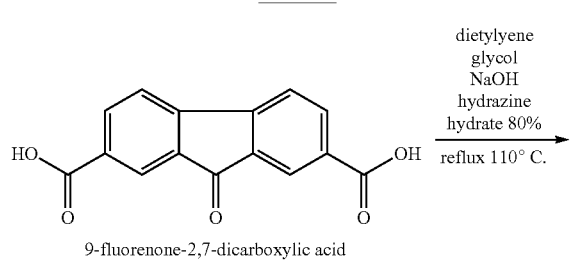

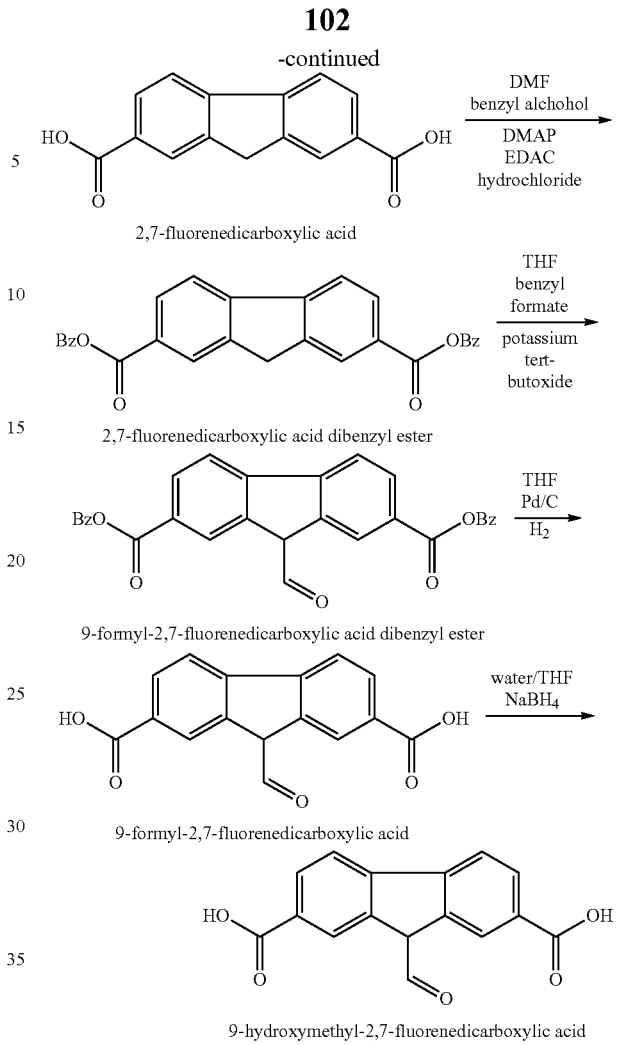

A. Preparation of 2,7-fluorenedicarboxylic acid

In an argon-purged flask, 9-fluorenone-2,7-dicarboxylic acid (10.0 g, 0.037 mol) was suspended in diethylene glycol (75 mL). The flask was placed in a room temperature oil bath then NaOH (6.2 g, 0.155 mol) and an 80% solution of hydrazine hydrate (7.4 mL, 0.12 mol) were added successively. The reaction mixture was slowly heated to 110 C and refluxed for approximately four hours. The reaction mixture was cooled, carefully poured into water and acidified to pH 2 with concentrated HCl. The product was filtered and washed with water. Product was dissolved in warm NaOH solution (0.5M, warm) and precipitated by acidification to pH 2 with HCl. The product was filtered and washed with water. Product was an yellow solid (9.0 g, 96%). $^1$H-NMR (d$_6$-DMSO): δ (ppm) 8.2 (s, 2H, Ar); 8.1 (m, 2H, Ar); 8.0 (m, 2H, Ar); 4.1 (s, 2H, CH$_2$).

B. Preparation of 2,7-fluorenedicarboxylic acid dibenzyl ester

In an nitrogen-purged dry flask, 2,7-fluorenedicarboxylic acid (8.0 g, 0.031 mol) was dissolved in anhydrous DMF (400 mL). Anhydrous benzyl alcohol (82 mL, 0.788 mol), DMAP (0.58 g, 0.0047 mol) and EDAC hydrochloride (16 g, 0.082 mol) were added to the reaction mixture at room temperature. After stirring for 24 hours, the reaction mixture was warmed and quenched by the addition of very dilute HCl (1.5 L). The suspension was cooled, filtered and washed with water. The product was dissolved in warm acetone (800 mL) and filtered while warm. The filtrate was evaporated to dryness at reduced pressure (Yield 5.9 g, 43%) ("Bz" in Scheme 5 represents benzyl). $^1$H-NMR (d$_6$-DMSO): δ (ppm) 8.3 (s, 2H, Ar); 8.2 (m, 2H, Ar); 8.1 (m, 2H, Ar); 7.5-7.4 (m, 10H, Bz); 5.4 (s, 4H CH$_2$); 4.1 (s, 2H, Ar).

C. Preparation of 9-formyl-2,7-fluorenedicarboxylic acid dibenzyl ester

In a dry argon-purged flask, 2,7-fluorenedicarboxylic acid dibenzyl ester (3.0 g, 0.0065 mol) was dissolved in anh. THF (60 mL) at room temperature. Benzyl formate (4.2 mL, 0.035 mol, stored over anhydrous K$_2$CO$_3$) was added followed by addition of potassium tert-butoxide 95% (2.7 g, 0.023 mol). The reaction was stirred for three hours then the reaction was quenched with the addition of water and acidified with HCl to pH 2. The organic solvent was partially evaporated at reduced pressure. The product was twice extracted with ethyl acetate (600 mL then 200 mL). The combined organic layers were washed three times with brine, dried over sodium sulfate, filtered and evaporated to dryness. The crude product was washed with hexanes and methanol (1.9 g, 60%). $^1$H-NMR (d$_6$-DMSO): δ (ppm) 11.9 (s, ~1H, formyl); 8.8 (s, 1H, Ar); 8.5 (s, 1H, Ar); 8.4 (s, 1H, Ar); 8.2 (m, 2H, Ar); 7.9 (m, 2H, Ar); 7.5-7.4 (m, 10H, Bz); 5.4 (s, 4H, Ar).

D. Preparation of 9-formyl-2,7-fluorenedicarboxylic acid

In a Parr hydrogenation bottle (Parr Instrument Company, Moline Ill.) was dissolved 9-formyl-2,7-fluorenedicarboxylic acid dibenzyl ester (3.0 g, 0.0061 mol) in THF anh. (350 mL). After careful addition of 20% Pd/C (wet with 50% water) 20% by weight (600 mg), the Parr bottle was evacuated/filled 3 times on a Parr apparatus to ensure hydrogen atmosphere. The suspension was shaken under 20-30 psi hydrogen gas for approximately 60 hours and then the remaining hydrogen was removed at reduced pressure. The suspension was filtered over a bed of celite, rinsed with additional THF and evaporated. $^1$H-NMR (d$_6$-DMSO): δ (ppm) 9.0 (s, 1H, Ar); 8.5-8.1 (m, 6H, Ar).

E. Preparation of 9-hydroxymethyl-2,7-fluorenedicarboxylic acid

A small sample of 9-formyl-2,7-fluorenedicarboxylic acid (5-10 mg) was dissolved in water with a small amount of THF. An excess amount of sodium borohydride was added and allowed to react for two hours. The reaction was quenched with the careful addition of 1 M HCl until acidic. The product was extracted with ethyl acetate, dried over sodium sulfate, filtered and evaporated to dryness. $^1$H-NMR (CD$_3$OD): δ (ppm) 8.4 (s, 2H, Ar); 8.2 (m, 2H, Ar); 8.0 (m, 2H, Ar); 4.2 (t, 1H, CH); 4.0 (d, 2H, CH$_2$).

Example 14

Preparation of 9-hydroxymethyl-2,7-di(3-carboxypropyl)fluorene, an Intermediate for the Preparation of 9-hydroxymethyl-2,7-bis-(3-(mPEG$_{10K}$ carbamoyl-propyl))fluorene-N-hydroxysuccinimide; (2,7-CA2-PEG2-Fmoc$_{20K}$-NHS)

The synthesis of 9-hydroxymethyl-2,7-di(3-carboxy-propyl)fluorene is represented schematically in Scheme 6, below.

Scheme 6.

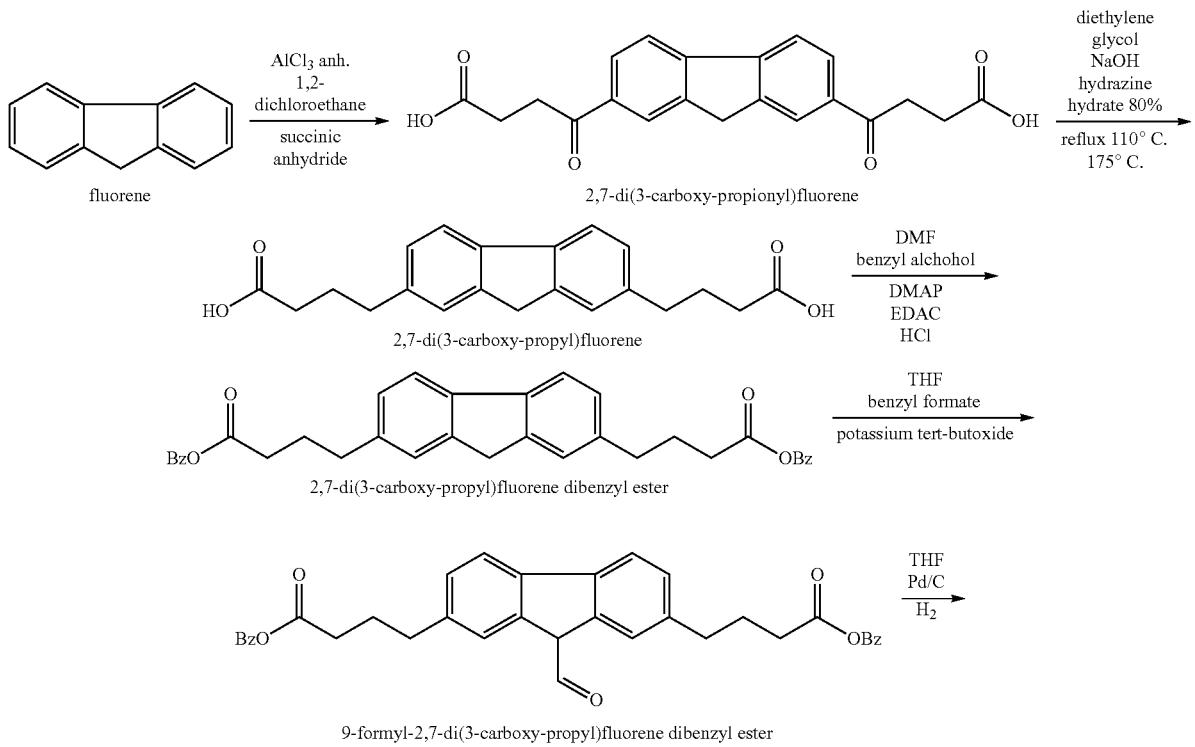

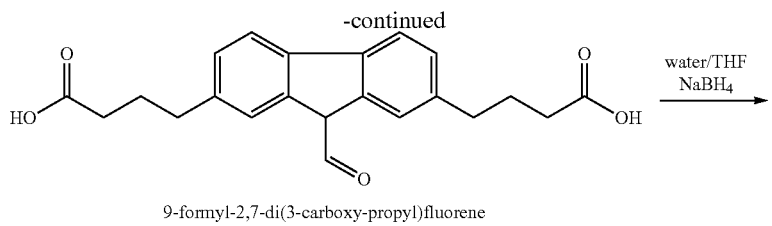

9-formyl-2,7-di(3-carboxy-propyl)fluorene

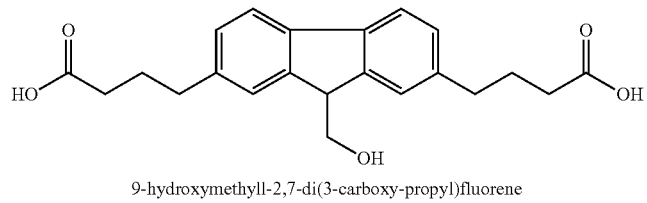

9-hydroxymethyll-2,7-di(3-carboxy-propyl)fluorene

A. Preparation of 2,7-di(3-carboxy-propionyl)fluorene

In a dry agon-purged round bottom flask, anhydrous AlCl₃ (98 g, 0.735 mol) was suspended in anhydrous 1,2-dichloroethane (140 mL). In a separate flask, fluorene (23 g, 0.138 mol) was dissolved in anh. 1,2-dichloroethane (125 mL) then added to the AlCl₃ suspension. The reaction flask was placed in a room temperature bath and succinic anhydride (34.5 g, 0.345 mol) was carefully added. The reaction was stirred for 16 hours and then very carefully quenched by slow addition to cold 3 M HCl (Caution! The reaction can react violently when HCl is added too rapidly.) The final well mixed suspension was acidic and not reactive to additional HCl solution. The organic solvent was removed at reduced pressure then the product was filtered and washed well with water. The crude product was dissolved in warm NaOH solution (approximately <1M NaOH), filtered and precipitated with the addition of concentrated HCl. The product was filtered, washed with water and then dried at reduced pressure in the presence of $P_2O_5$. The product was a pale yellow solid (49.3 g, 97%). $^1$H-NMR (CD₃OD): δ (ppm) 8.3 (s, 2H, Ar); 8.2 (m, 2H, Ar); 8.1 (m, 2H, Ar); 4.1 (s, 2H, CH₂); 3.5 (t, 4H, CH₂); 2.8 (t, 4H, CH₂).

B. Preparation of 2,7-di(3-carboxy-propyl)fluorene

In an argon-purged flask 2,7-di(3-carboxy-propionyl)fluorene (12.8 g, 0.035 mol) was suspended in diethylene glycol (150 mL). The flask was placed in a room temperature oil bath then NaOH (14 g, 0.35 mol) and an 80% solution of hydrazine hydrate (13.1 mL, 0.21 mol) were added successively. The reaction mixture was slowly heated to 110° C. and refluxed for approximately two hours. The reaction temperature was raised to 200° C. with removal of water during the heating process. After three hours at 200° C. reaction temperature the reaction was cooled to approximately 60° C. The reaction mixture was carefully poured into water (500 mL) and the mixture was acidified to pH 2 with concentrated HCl. The product was filtered and washed with water. The product was dissolved in warm NaOH solution (0.5M) and precipitated by acidification to pH 2 with HCl. The product was filtered and washed with water (Yield 10.9 g, 92%). $^1$H-NMR (d₆-DMSO): δ (ppm) 12.0 (s, 2H, COOH); 7.8 (m, 2H, Ar); 7.4 (s, 2H, Ar); 7.2 (m, 2H, Ar); 3.9 (s, 2H, CH₂); 2.7 (t, 4H, CH₂); 2.3 (t, 4H, CH₂); 1.8 (m, 4H, CH₂).

C. Preparation of 2,7-di(3-carboxy-propyl)fluorene dibenzyl ester

In a nitrogen-purged dry flask, 2,7-di(3-carboxy-propyl)fluorene (3.0 g, 0.009 mol) was dissolved in anhydrous DMF (50 mL). Anhydrous benzyl alcohol (23 mL, 0.22 mol), DMAP (0.27 g, 0.0022 mol) and EDAC hydrochloride (4.5 g, 0.023 mol) were added to the reaction mixture at room temperature. After stirring for 21 hours, the reaction mixture was warmed and quenched by the addition of very dilute HCl (400 mL). The suspension was cooled, filtered and washed with water. The product was dissolved in warm acetone and filtered while warm. The filtrate was evaporated to dryness at reduced pressure (Yield 3.8 g, 78%). $^1$H-NMR (d₆-DMSO): δ (ppm) 7.7 (m, 2H, Ar); 7.4 (m, 12H, Ar); 7.1 (m, 2H, Ar); 5.1 (s, 4H, CH₂); 3.8 (s, 2H, CH₂); 2.7 (t, 4H, CH₂); 2.4 (t, 4H, CH₂); 1.9 (m, 4H, CH₂).

D. Preparation of 9-formyl-2,7-di(3-carboxy-propyl)fluorene dibenzyl ester

In a dry argon-purged flask, 2,7-di(3-carboxy-propyl)fluorene dibenzyl ester (2.0 g, 0.0039 mol) was dissolved in anh. THF (40 mL) at room temperature. Benzyl formate (2.3 mL, 0.019 mol, stored over anh. K₂CO₃) was added followed by addition of potassium tert-butoxide 95% (1.5 g, 0.013 mol). The reaction was stirred for four hours then the reaction was quenched with the addition of water and acidified with HCl to pH 2. The organic solvent was partially evaporated at reduced pressure. The product was twice extracted with ethyl acetate. The combined organic layers were washed three times with brine, dried over sodium sulfate, filtered and evaporated to dryness. The crude product was titurated with hexanes (some benzyl formate remains). $^1$H-NMR (d₆-DMSO): δ (ppm) 11.0 (s, ~1H, formyl); 8.0 (s, 1H, Ar); 7.9 (s, 1H, Ar); 7.7 (m, 2H, Ar); 7.6 (s, 1H, Ar); 7.4-7.2 (m, Bz); 7.0 (m, 2H, Ar); 5.0 (s, 4H, CH₂); 2.7 (m, 4H, CH₂); 2.4 (m, 4H, CH₂); 1.9 (m, 4H, CH₂).

Example 15

Preparation of 9-hydroxymethyl-2,7-di(mPEG(20,000)-methylamide)-sulfonic acid-fluorene-N-hydroxysuccinimide

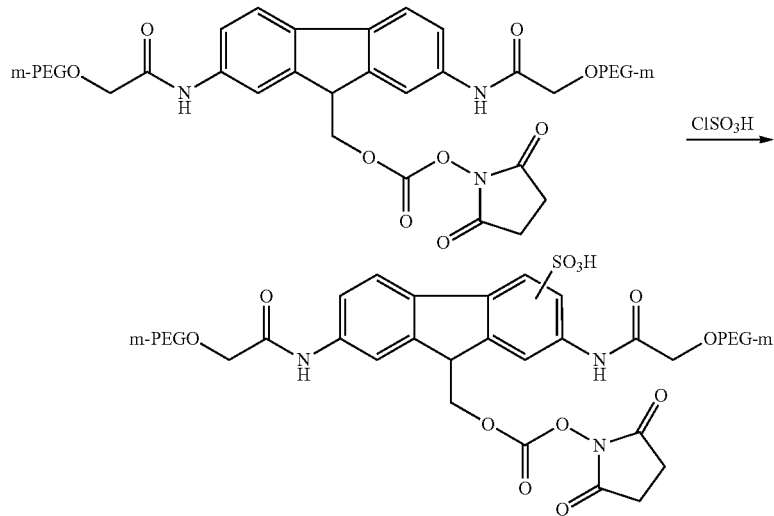

In a dry argon purged flask, 9-hydroxymethyl-2,7-di(mPEG(20,000)-methylamide)fluorene-N-hydroxysuccinimide (1 g, 0.026 mmol) was dissolved in DCM anhydrous (10 mL) A solution of chlorosulfonic acid (0.05 mL in 50 mL trifluoroacetic acid, 2.1 mL) was added to the reaction mixture. Over the next several hours additional chlorosulfonic acid (0.287 mL) was added to the reaction and stirred for more than five hours. The solvent was evaporated at reduced pressure and then dissolved in DCM. The solvent was again evaporated at reduced pressure. The crude product demonstrated the presence of sulfonic acid modified structure by HPLC analysis. $^1$H-NMR ($d_6$-DMSO): δ (ppm) 8.2 (bs, 1H, NH amide); 7.6 (m, 1H, Ar); 7.5 (m, 1H, Ar); 7.2 (t, 1H, Ar); 6.7 (s, 1H, Ar); 6.5 (d, 1H, Ar); 5.3 (bs, 1H, NH amide); 3.8 (s, 2H, $CH_2$); 3.5 (s); 3.3 (bs, PEG backbone); additional contaminate shifts below 2.5 ppm were present in the crude product.

The sulfonic acid electron altering group can be added to polymeric reagents other than 9-hydroxymethyl-2,7-di(mPEG(20,000)-methylamide)fluorene-N-hydroxysuccinimide encompassed by the present invention (including those polymeric reagents described in the Experimental).

What is claimed is:

1. A pharmaceutical composition comprising a pharmaceutically acceptable excipient and a conjugate of the following formula:

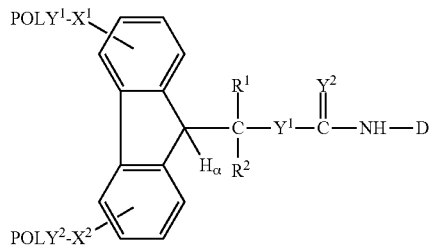

wherein:
 $POLY^1$ is a first water-soluble polymer;
 $POLY^2$ is a second water-soluble polymer;
 $X^1$ is a first spacer moiety;
 $X^2$ is a second spacer moiety;
 $H_\alpha$ is an ionizable hydrogen atom;
 $R^1$ is H or an organic radical;
 $R^2$ is H or an organic radical; and
 $Y^1$ is O or S;
 $Y^2$ is O or S; and
 D is a residue of a biologically active agent.

2. The pharmaceutical composition of claim 1, wherein each of $POLY_1$ and $POLY^2$ is a poly(ethylene glycol).

3. The pharmaceutical composition of claim 2, wherein each poly(ethylene glycol) has a weight-average molecular weight in the range of from about 120 Daltons to about 6,000 Daltons.

4. The pharmaceutical composition of claim 2, wherein each poly(ethylene glycol) has a weight-average molecular weight in the range of from about 6,000 Daltons to about 100,000 Daltons.

5. The pharmaceutical composition of claim 1 wherein the first spacer moiety is selected from the group consisting of —C(O)—NH—$CH_2$—$CH_2$—, —$CH_2$—$CH_2$—NH—C(O)—, —C(O)—NH—$CH_2$—$CH_2$—$CH_2$—, —$CH_2$—$CH_2$—$CH_2$—NH—C(O)—, —C(O)—NH—$CH_2$—$CH_2$—$CH_2$—$CH_2$—, —$CH_2$—$CH_2$—$CH_2$—$CH_2$—NH—C(O)—, —C(O)—NH—, —NH—C(O)—, —C(O)—NH—$CH_2$—$CH_2$—$CH_2$—$CH_2$—, —$CH_2$—$CH_2$—$CH_2$—$CH_2$—$CH_2$—NH—C(O)—, —NH—C(O)—$CH_2$—$CH_2$—, —$CH_2$—$CH_2$—C(O)—NH—, —NH—C(O)—$CH_2$—$CH_2$—, —$CH_2$—$CH_2$—$CH_2$—C(O)—NH—, —NH—C(O)—$CH_2$—$CH_2$—$CH_2$—$CH_2$—, —$CH_2$—$CH_2$—$CH_2$—$CH_2$—C(O)—NH—, —NH—C(O)—$CH_2$—$CH_2$—$CH_2$—$CH_2$—, —$CH_2$—$CH_2$—$CH_2$—$CH_2$—$CH_2$—C(O)—NH—, —NH—C(O)—$CH_2$—$CH_2$—C(O)—, —C(O)—$CH_2$—$CH_2$—C(O)—NH—, —NH—C(O)—$CH_2$—$CH_2$—C(O)—, —C(O)—$CH_2$—$CH_2$—$CH_2$—C(O)—, —C(O)—$CH_2$—$CH_2$—$CH_2$—$CH_2$—C(O)—NH—, —NH—C(O)—$CH_2$—$CH_2$—$CH_2$—

CH₂—C(O)—, —C(O)—CH₂—CH₂—CH₂—CH₂—C(O)—NH—, —NH—C(O)—CH₂—CH₂—CH₂—CH₂—CH₂—C(O)—, —C(O)—CH₂—CH₂—CH₂—CH₂—CH₂—C(O)—NH—, —C(O)—CH₂—CH₂—, —CH₂—CH₂—C(O)—, —C(O)—CH₂—CH₂—CH₂—, —CH₂—CH₂—CH₂—C(O)—, —C(O)—CH₂—CH₂—CH₂—CH₂—, —CH₂—CH₂—CH₂—CH₂—C(O)—, —C(O)—CH₂—CH₂—CH₂—CH₂—CH₂—, —CH₂—CH₂—CH₂—CH₂—CH₂—C(O)—, —NH—CH₂—CH₂—(OCH₂CH₂)₁₋₃—NH—C(O)—, —C(O)—NH—(CH₂CH₂O)₁₋₃—CH₂—CH₂—NH—, —C(O)—NH—CH₂—CH₂—(OCH₂CH₂)₁₋₃—NH—C(O)—, —C(O)—NH—(CH₂CH₂O)₁₋₃—CH₂—CH₂—NH—C(O)—, —NH—C(O)—CH₂—, —CH₂—C(O)—NH—, —NH—C(O)—CH₂—O—, —O—CH₂—C(O)—NH—, —CH₂—CH₂—NH—C(O)—CH₂—CH₂—CH₂—C(O)—NH—, —NH—C(O)—CH₂—CH₂—CH₂—C(O)—NH—CH₂—CH₂—, —O—CH₂—CH₂—NH—C(O)—CH₂—CH₂—CH₂—C(O)—NH—, —NH—C(O)—CH₂—CH₂—CH₂—C(O)—NH—CH₂—CH₂—O—, —C(O)—NH—CH₂—CH₂—, —CH₂—CH₂—NH—C(O)—, —C(O)—NH—CH₂—CH₂—O—, and —O—CH₂—CH₂—NH—C(O)—, and the second spacer moiety is selected from the group consisting of —C(O)—NH—CH₂—CH₂—, —CH₂—CH₂—NH—C(O)—, —C(O)—NH—CH₂—CH₂—CH₂—, —CH₂—CH₂—CH₂—NH—C(O)—, —C(O)—NH—CH₂—CH₂—CH₂—CH₂—, —CH₂—CH₂—CH₂—CH₂—NH—C(O)—, —C(O)—NH—CH₂—CH₂—CH₂—CH₂—CH₂—, —CH₂—CH₂—CH₂—CH₂—CH₂—NH—C(O)—, —NH—C(O)—CH₂—, —CH₂—CH₂—C(O)—NH—, —NH—C(O)—CH₂—CH₂—CH₂—, —CH₂—CH₂—CH₂—C(O)—NH—, —NH—C(O)—CH₂—CH₂—CH₂—CH₂—, —CH₂—

CH₂—CH₂—CH₂—C(O)—NH—, —NH—C(O)—CH₂—CH₂—CH₂—CH₂—, —CH₂—CH₂—CH₂—CH₂—CH₂—C(O)—NH—, —NH—C(O)—CH₂—CH₂—C(O)—, —C(O)—CH₂—CH₂—C(O)—NH—, —NH—C(O)—CH₂—CH₂—CH₂—C(O)—, —C(O)—CH₂—CH₂—CH₂—C(O)—NH—, —NH—C(O)—CH₂—CH₂—CH₂—CH₂—C(O)—, —C(O)—CH₂—CH₂—CH₂—CH₂—C(O)—NH—, —NH—C(O)—CH₂—CH₂—CH₂—CH₂—CH₂—C(O)—, —C(O)—CH₂—CH₂—CH₂—CH₂—CH₂—C(O)—NH—, —C(O)—CH₂—CH₂—, —CH₂—CH₂—C(O)—, —C(O)—CH₂—CH₂—CH₂—, —CH₂—CH₂—CH₂—C(O)—, —C(O)—CH₂—CH₂—CH₂—CH₂—, —CH₂—CH₂—CH₂—CH₂—C(O)—, —C(O)—CH₂—CH₂—CH₂—CH₂—CH₂—, —CH₂—CH₂—CH₂—CH₂—CH₂—C(O)—, —NH—CH₂—CH₂—(OCH₂CH₂)₁₋₃—NH—C(O)—, —C(O)—NH—(CH₂CH₂O)₁₋₃—CH₂—CH₂—NH—, —C(O)—NH—CH₂—CH₂—(OCH₂CH₂)₁₋₃—NH—C(O)—, —C(O)—NH—(CH₂CH₂O)₁₋₃—CH₂—CH₂—NH—C(O)—, —NH—C(O)—CH₂—, —CH₂—C(O)—NH—, —NH—C(O)—CH₂—O—, —O—CH₂—C(O)—NH—, —CH₂—CH₂—NH—C(O)—CH₂—CH₂—CH₂—C(O)—NH—, —NH—C(O)—CH₂—CH₂—CH₂—C(O)—NH—CH₂—CH₂—, —O—CH₂—CH₂—NH—C(O)—CH₂—CH₂—CH₂—C(O)—NH—, —NH—C(O)—CH₂—CH₂—CH₂—C(O)—NH—CH₂—CH₂—O—, —C(O)—NH—CH₂—CH₂—, —CH₂—CH₂—NH—C(O)—, —C(O)—NH—CH₂—CH₂—O—, and —O—CH₂—CH₂—NH—C(O)—.

6. The pharmaceutical composition of claim 1, wherein $R^1$ is H and $R^2$ is H.

7. The pharmaceutical composition of claim 1, wherein $Y^1$ is O and $Y^2$ is O.

8. The pharmaceutical composition of claim 1, wherein the biologically active agent is a polypeptide.

9. The pharmaceutical composition of claim 1, wherein the conjugate corresponds to the following formula:

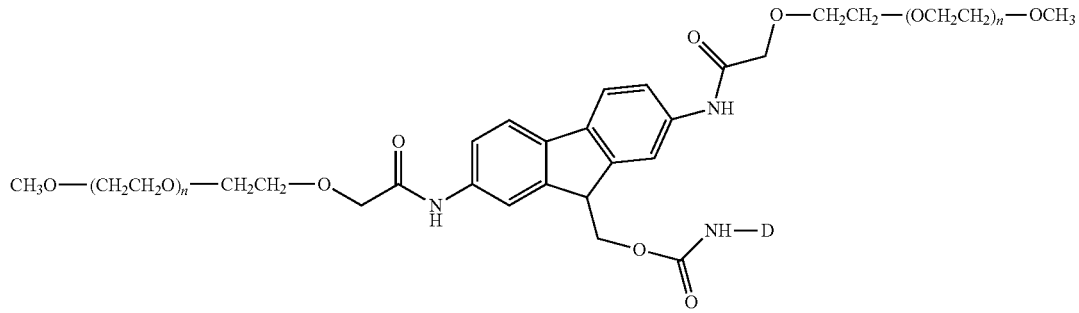

wherein each (n) is from 4 to 1500 and D is a residue of a biologically active agent.

10. The pharmaceutical composition of claim 1, wherein the conjugate corresponds to the following formula:

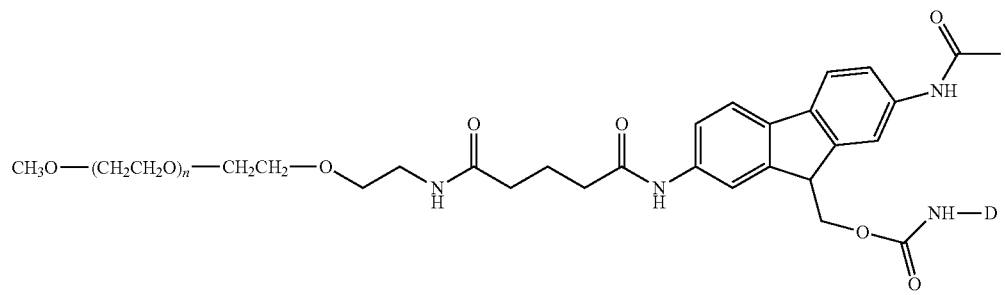

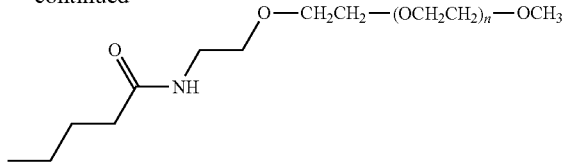

wherein each (n) is from 4 to 1500 and D is a residue of a biologically active agent.

11. The pharmaceutical composition of claim 1, wherein the conjugate corresponds to the following formula:

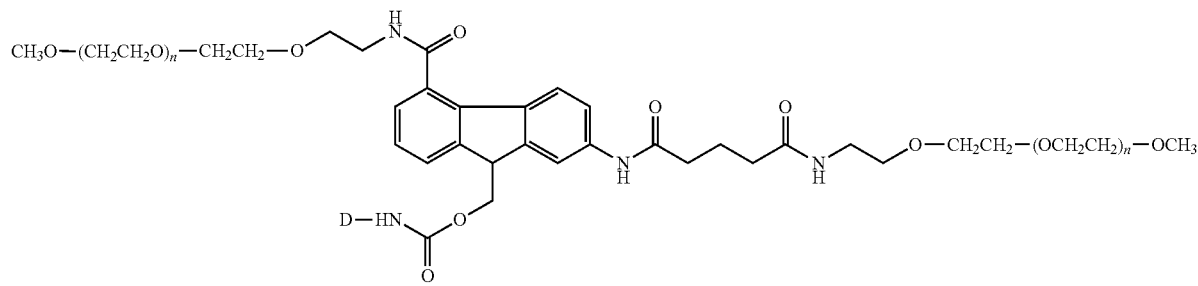

wherein each (n) is from 4 to 1500 and D is a residue of a biologically active agent.

12. The pharmaceutical composition of claim 1, wherein the conjugate corresponds to the following formula:

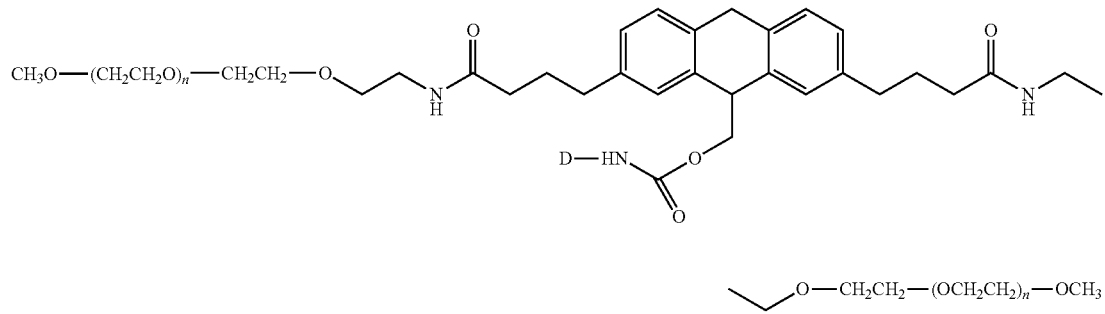

wherein each (n) is from 4 to 1500 and D is a residue of a biologically active agent.

13. The pharmaceutical composition of claim 1, wherein the conjugate corresponds to the following formula:

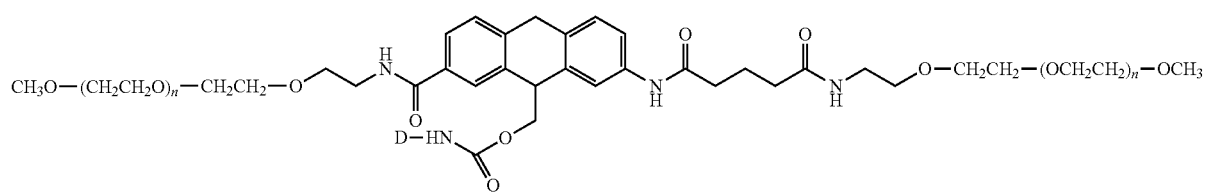

wherein each (n) is from 4 to 1500 and D is a residue of a biologically active agent.

14. The pharmaceutical composition of claim 1, wherein the conjugate corresponds to the following formula:

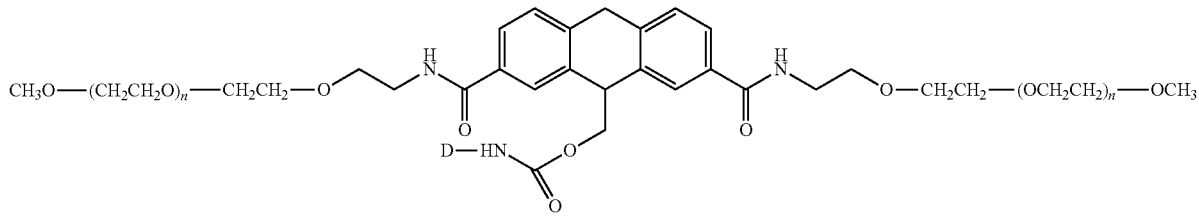

wherein each (n) is from 4 to 1500 and D is a residue of a biologically active agent.

15. The pharmaceutical composition of claim 1, wherein the conjugate corresponds to the following formula:

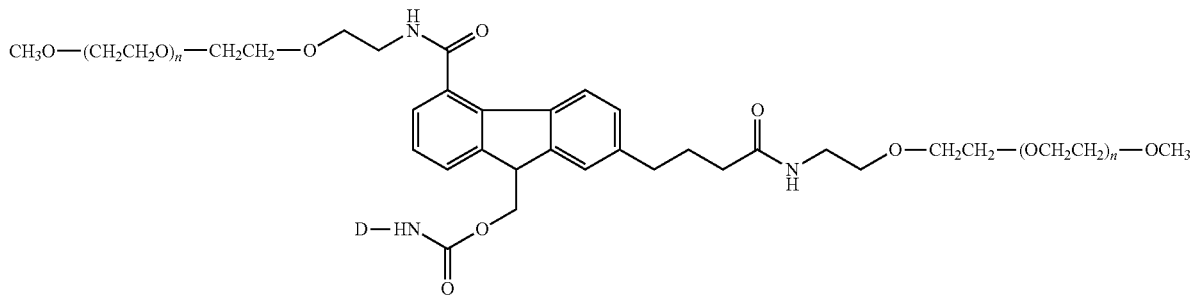

wherein each (n) is from 4 to 1500 and D is a residue of a biologically active agent.

16. The pharmaceutical composition of claim 1, in lyophilized form.

17. The pharmaceutical composition of claim 1, further comprising a liquid diluent.

18. The pharmaceutical composition of claim 17, wherein the liquid diluent is selected from the group consisting of bacteriostatic water for injection, dextrose 5% in water, phosphate-buffered saline, Ringer's solution, saline solution, sterile water, deionized water, and combinations thereof.

19. The pharmaceutical composition of claim 1, in unit dosage form.

20. The pharmaceutical composition of claim 19, housed in a glass vial.

21. A method of delivering a conjugate comprising the step of administering to a patient a therapeutically effective amount of a conjugate according to claim 1.

* * * * *